(12) United States Patent
Allison et al.

(10) Patent No.: US 7,704,701 B2
(45) Date of Patent: Apr. 27, 2010

(54) DIAGNOSIS OF PROSTATE CANCER WITH SPAS-1 CANCER ANTIGEN

(75) Inventors: James P. Allison, Berkeley, CA (US); Marcella Fasso, Oakland, CA (US); Nilabh Shastri, Richmond, CA (US)

(73) Assignee: The Regents of the University of California, Oakland, CA (US)

( * ) Notice: Subject to any disclaimer, the term of this patent is extended or adjusted under 35 U.S.C. 154(b) by 198 days.

(21) Appl. No.: 11/699,879

(22) Filed: Jan. 29, 2007

(65) Prior Publication Data

US 2007/0202121 A1    Aug. 30, 2007

Related U.S. Application Data

(63) Continuation-in-part of application No. 09/952,432, filed on Sep. 13, 2001, now abandoned.

(60) Provisional application No. 60/234,472, filed on Sep. 21, 2000.

(51) Int. Cl.
    *G01N 33/574* (2006.01)
(52) U.S. Cl. .................. 435/7.23; 435/7.21
(58) Field of Classification Search ............ None
    See application file for complete search history.

(56) References Cited

OTHER PUBLICATIONS

Lederman et al. Molecular Immunology 28:1171-1181, 1991.*
Li et al. Proc. Natl. Acad. Sci. USA 77:3211-3214, 1980.*
Fu et al. EMBO Journal, 15:4392-4401, 1996.*
Gygi et al. Molecular and Cellular Biology, 19(3): 1720-1730, Mar. 1999.*
Haynes et al. Electrophoresis 19:1862-1871, 1998.*
Hanash S. Nature Reviews, Applied Proteomics Collection, pp. 9-14, Mar. 2005.*
Winstead I. Genome News Network, "The Evolving Art of Arrays", www.genomenewsnetwork.or.q, pp. 1-4, Sep. 15, 2000.*
Irving et al. Nature Biotechnology, 18:932-933, Sep. 2000.*
Dranoff et al. (1993) "Vaccination with irradiated tumor cells engineered to secrete murine granulocyte-macrophage colony-stimulating factor stimulates potent, specific, and long-lasting anti-tumor immunity" *Proc. Natl. Acad. Sci. USA* 90:3539-3543.
Hurwitz et al. (2000) "Combination immunotherapy of primary prostate cancer in a transgenic mouse model using CTLA-4 blockade" *Cancer Res.* 60:2444-2448.
Karttunen et al. (1992) "Detection of rare antigen-presenting cells by the *lacZ* T-cell activation assay suggests an expression cloning strategy for T-cell antigens" *Proc. Natl. Acad. Sci. USA* 89:6020-6024.
Pierrat et al. (2001) "SH3GLB, a new endophilin-related protein family featuring an SH3 domain" *Genomics* 71:222-234.
Thompson, C. and Allison, J. (1997) "The emerging role of CTLA-4 as an immune attenuator" *Immunity* 7:445-450.
van Elsas et al. (1999) "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation" *J. Exp. Med.* 190(3):355-366.

* cited by examiner

*Primary Examiner*—Sheela J Huff
(74) *Attorney, Agent, or Firm*—Bozicevic, Field & Francis LLP; Pamela J. Sherwood

(57) ABSTRACT

Compounds and methods for inducing protective immunity against cancer are disclosed. The compounds provided include polypeptides that contain at least one immunogenic portion of one or more SPAS-1 proteins and DNA molecules encoding such polypeptides. Such compounds may be formulated into vaccines and pharmaceutical compositions for immunization against cancer, or can be used for the diagnosis of cancer and the monitoring of cancer progression.

3 Claims, 40 Drawing Sheets

```
              10          20          30          40
     *    *    *    *    *    *    *    *    *    *
    CTG  GAA  AGC  AGT  ACT  CAT  GTG  AAC  CAC  CTT  CAC  TGC  CTC  CAT  GAG  TTC
    GAC  CTT  TCG  TCA  TGA  GTA  CAC  TTG  GTG  GAA  GTG  ACG  GAG  GTA  CTC  AAG
    Leu  Glu  Ser  Ser  Thr  His  Val  Asn  His  Leu  His  Cys  Leu  His  Glu  Phe>

50          60          70          80          90
     *    *    *    *    *    *    *    *    *    *    *
    GTC  AAG  TCT  CAG  ACA  ACC  TAC  TAT  GCA  CAG  TGC  TAC  CGC  CAC  ATG  CTG
    CAG  TTC  AGA  GTC  TGT  TGG  ATG  ATA  CGT  GTC  ACG  ATG  GCG  GTG  TAC  GAC
    Val  Lys  Ser  Gln  Thr  Thr  Tyr  Tyr  Ala  Gln  Cys  Tyr  Arg  His  Met  Leu>

100         110         120         130         140
     *    *    *    *    *    *    *    *    *    *
    GAT  CTG  CAG  AAA  CAG  CTA  GGC  AGA  TTT  CCA  GGC  ACC  TTC  GTG  GGC  ACC
    CTA  GAC  GTC  TTT  GTC  GAT  CCG  TCT  AAA  GGT  CCG  TGG  AAG  CAC  CCG  TGG
    Asp  Leu  Gln  Lys  Gln  Leu  Gly  Arg  Phe  Pro  Gly  Thr  Phe  Val  Gly  Thr>

150         160         170         180         190
     *    *    *    *    *    *    *    *    *    *
    ACA  GAG  CCT  GCC  TCC  CCA  CCC  CTG  AGC  AGC  ACC  TCA  CCT  ACC  ACC  ACT
    TGT  CTC  GGA  CGG  AGG  GGT  GGG  GAC  TCG  TCG  TGG  AGT  GGA  TGG  TGG  TGA
    Thr  Glu  Pro  Ala  Ser  Pro  Pro  Leu  Ser  Ser  Thr  Ser  Pro  Thr  Thr  Thr>

200         210         220         230         240
     *    *    *    *    *    *    *    *    *    *
    GCG  GCC  ACC  ATG  CCT  GTG  GTA  CCT  ACT  GGG  GCT  GTC  TTG  GCC  CCT  CCA
    CGC  CGG  TGG  TAC  GGA  CAC  CAT  GGA  TGA  CCC  CGA  CAG  AAC  CGG  GGA  GGT
    Ala  Ala  Thr  Met  Pro  Val  Val  Pro  Thr  Gly  Ala  Val  Leu  Ala  Pro  Pro>

250         260         270         280
     *    *    *    *    *    *    *    *    *
    GAA  GAG  GCA  GCC  CTC  TGC  CTG  GAG  GAG  GTG  GCT  CCC  CCA  GCC  AGT  GGG
    CTT  CTC  CGT  CGG  GAG  ACG  GAC  CTC  CTC  CAC  CGA  GGG  GGT  CGG  TCA  CCC
    Glu  Glu  Ala  Ala  Leu  Cys  Leu  Glu  Glu  Val  Ala  Pro  Pro  Ala  Ser  Gly>

290         300         310         320         330
     *    *    *    *    *    *    *    *    *    *
    ACT  CGA  AAG  GCC  CGG  GTG  CTC  TAC  GAC  TAC  GAG  GCA  GCT  GAC  AGC  AGT
    TGA  GCT  TTC  CGG  GCC  CAC  GAG  ATG  CTG  ATG  CTC  CGT  CGA  CTG  TCG  TCA
    Thr  Arg  Lys  Ala  Arg  Val  Leu  Tyr  Asp  Tyr  Glu  Ala  Ala  Asp  Ser  Ser>

340         350         360         370         380
     *    *    *    *    *    *    *    *    *    *
    GAG  CTG  GCC  CTG  CTG  GCT  GAT  GAG  CTC  ATC  ACT  GTC  TAC  AGC  CTG  CCA
    CTC  GAC  CGG  GAC  GAC  CGA  CTA  CTC  GAG  TAG  TGA  CAG  ATG  TCG  GAC  GGT
    Glu  Leu  Ala  Leu  Leu  Ala  Asp  Glu  Leu  Ile  Thr  Val  Tyr  Ser  Leu  Pro>

390         400         410         420         430
     *    *    *    *    *    *    *    *    *    *
    GGC  ATG  GAT  CCC  GAC  TGG  CTC  ATT  GGT  GAG  AGA  GGC  AAC  AAG  AAG  GGC
    CCG  TAC  CTA  GGG  CTG  ACC  GAG  TAA  CCA  CTC  TCT  CCG  TTG  TTC  TTC  CCG
    Gly  Met  Asp  Pro  Asp  Trp  Leu  Ile  Gly  Glu  Arg  Gly  Asn  Lys  Lys  Gly>
```

FIG. 1A (1 of 3)

```
            440         450         460         470         480
    *         *    *    *         *    *    *         *    *    *
AAG GTT CCT GTC ACC TAC CTG GAA CTT CTC AGC TAA GCA GCC CCT TCC
TTC CAA GGA CAG TGG ATG GAC CTT GAA GAG TCG ATT CGT CGG GGA AGG
Lys Val Pro Val Thr Tyr Leu Glu Leu Leu Ser *** Ala Ala Pro Ser>

490         500         510         520
         *    *    *    *         *    *    *    *    *
CAG GCT CTG CCA CTT AGA GTC GTC TGC TGG CCA CAG AGC TGC TTA GGA
GTC CGA GAC GGT GAA TCT CAG CAG ACG ACC GGT GTC TCG ACG AAT CCT
Gln Ala Leu Pro Leu Arg Val Val Cys Trp Pro Gln Ser Cys Leu Gly>

530         540         550         560         570
    *         *    *    *         *    *    *         *    *    *
TAA GGG ACC TAA CCC TTT TCT GGC TGT GCC CGT CAT TCA GCT ATT AAA
ATT CCC TGG ATT GGG AAA AGA CCG ACA CGG GCA GTA AGT CGA TAA TTT
*** Gly Thr *** Pro Phe Ser Gly Cys Ala Arg His Ser Ala Ile Lys>

580         590         600         610         620
    *    *    *    *         *    *    *         *    *    *
GAG CCC ACA AGA CAG AAT GGC CCC AGG CCC CTC TGC TAG TCC TGC TTC
CTC GGG TGT TCT GTC TTA CCG GGG TCC GGG GAG ACG ATC AGG ACG AAG
Glu Pro Thr Arg Gln Asn Gly Pro Arg Pro Leu Cys *** Ser Cys Phe>

630         640         650         660         670
    *    *    *    *    *         *    *    *         *    *    *
TGA CCT GCA ACC CTG CAC ACC CCA GGC TTC CCA GCT CCC TTA AGG CAG
ACT GGA CGT TGG GAC GTG TGG GGT CCG AAG GGT CGA GGG AAT TCC GTC
*** Pro Ala Thr Leu His Thr Pro Gly Phe Pro Ala Pro Leu Arg Gln>

680         690         700         710         720
    *    *    *    *         *    *    *         *    *    *
AAG GGT CAC TAC ATT TGA CAC CAC CAT GGG CCC AGG ATA TGC TGG GGA
TTC CCA GTG ATG TAA ACT GTG GTG GTA CCC GGG TCC TAT ACG ACC CCT
Lys Gly His Tyr Ile *** His His His Gly Pro Arg Ile Cys Trp Gly>

730         740         750         760
         *    *    *    *         *    *    *    *    *
TGG ATG CTC TTG GCA TGA AAG AAC ATC TGC CTT CTG GCT GTG GAA GGT
ACC TAC GAG AAC CGT ACT TTC TTG TAG ACG GAA GAC CGA CAC CTT CCA
Trp Met Leu Leu Ala *** Lys Asn Ile Cys Leu Leu Ala Val Glu Gly>

770         780         790         800         810
    *         *    *    *         *    *    *         *    *    *
TGA GGG GGA CAG CAG CAC ACA GGC AGG GCT AGG AGT GTG GCA GGA AAC
ACT CCC CCT GTC GTC GTG TGT CCG TCC CGA TCC TCA CAC CGT CCT TTG
*** Gly Gly Gln Gln His Thr Gly Arg Ala Arg Ser Val Ala Gly Asn>

820         830         840         850         860
    *         *    *    *    *         *    *    *         *    *    *
CAG AAG GGT CAG CCA GAG CAG CAG CAC CAA GTG CTG CCT CCC ACT TCC
GTC TTC CCA GTC GGT CTC GTC GTC GTG GTT CAC GAC GGA GGG TGA AGG
Gln Lys Gly Gln Pro Glu Gln Gln His Gln Val Leu Pro Pro Thr Ser>
```

```
        870         880         890         900         910
  *      *     *     *     *     *     *     *     *     *
CTC ATG GCT CTG GCT GGG CAC AGT GGC TAC AGC AGT CAT TCC TTC AGT
GAG TAC CGA GAC CGA CCC GTG TCA CCG ATG TCG TCA GTA AGG AAG TCA
Leu Met Ala Leu Ala Gly His Ser Gly Tyr Ser Ser His Ser Phe Ser>

920         930         940         950         960
  *      *     *     *     *     *     *     *     *     *
TTC TAA CTA ACA TTC TGA CCT CTG CCT GTC TGC TTG CTC TCT GGC AAA
AAG ATT GAT TGT AAG ACT GGA GAC GGA CAG ACG AAC GAG AGA CCG TTT
Phe *** Leu Thr Phe *** Pro Leu Pro Val Cys Leu Leu Ser Gly Lys>

970         980         990
  *      *     *     *     *     *     *
TAA ATC CTT TGT GTG CGA AAA AAA AAA AAA AA
ATT TAG GAA ACA CAC GCT TTT TTT TTT TTT TT
*** Ile Leu Cys Val Arg Lys Lys Lys Lys Lys Xxx>
```

FIG. 1A (3 of 3)

Figure 1B:
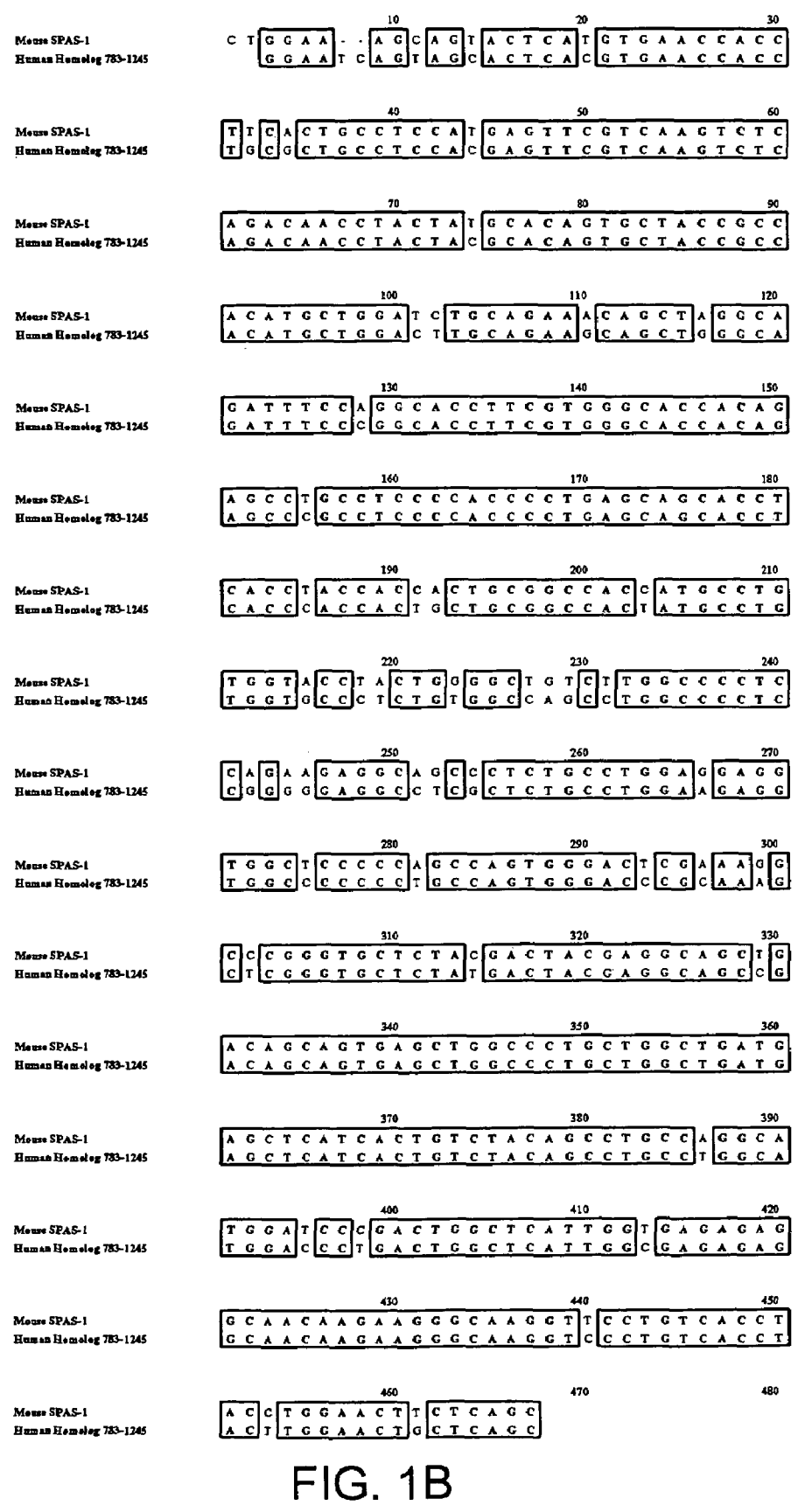

| | | |
|---|---|---|
| Mouse SPAS-1 | | C T [GGAA]‑‑[AG]C[AGT]ACTCA[T]GTGAACCACC |
| Human Homolog 783-1245 | | [GGAA]T C[AGT]AG[C]ACTCA[C]GTGAACCACC |

Alignment of Mouse SPAS-1 with Human Homolog 783-1245 (nucleotides 1–480).

```
         10                  20                  30                  40
ATG GAC TTC AAC ATG AAG AAG CTG GCG TCG GAC GCG GGC ATC TTC TTC
Met Asp Phe Asn Met Lys Lys Leu Ala Ser Asp Ala Gly Ile Phe Phe>

50                  60                  70                  80                  90
ACT CGG GCG GTG CAG TTC ACA GAG GAG AAG TTT GGC CAG GCT GAG AAG
Thr Arg Ala Val Gln Phe Thr Glu Glu Lys Phe Gly Gln Ala Glu Lys>

100                 110                 120                 130                 140
ACG GAG CTT GAC GCC CAC TTT GAA AAC CTC CTA GCT CGG GCA GAC AGC
Thr Glu Leu Asp Ala His Phe Glu Asn Leu Leu Ala Arg Ala Asp Ser>

150                 160                 170                 180                 190
ACC AAG AAC TGG ACA GAG CGG ATC CTG AGG CAG ACC GAG GTG CTG CTG
Thr Lys Asn Trp Thr Glu Arg Ile Leu Arg Gln Thr Glu Val Leu Leu>

200                 210                 220                 230                 240
CAG CCC AAC CCC AGT GCT CGA GTG GAG GAG TTC CTA TAT GAG AAG CTG
Gln Pro Asn Pro Ser Ala Arg Val Glu Glu Phe Leu Tyr Glu Lys Leu>

250                 260                 270                 280
GAC AGA AAG GTG CCC TCG AGA GTC ACC AAT GGG GAG CTG CTG GCT CAG
Asp Arg Lys Val Pro Ser Arg Val Thr Asn Gly Glu Leu Leu Ala Gln>

290                 300                 310                 320                 330
TAC ATG GCG GAG GCA GCC AGC GAG CTG GGC CCC AGC ACT CCC TAC GGG
Tyr Met Ala Glu Ala Ala Ser Glu Leu Gly Pro Ser Thr Pro Tyr Gly>

340                 350                 360                 370                 380
AAG ACG CTG ATC AAG GTG TCA GAA GCT GAG AAG CGC CTC GGA GCA GCA
Lys Thr Leu Ile Lys Val Ser Glu Ala Glu Lys Arg Leu Gly Ala Ala>

390                 400                 410                 420                 430
GAG CGG GAT TTC ATT CAC ACT GCC TCC CTC AGC TTC CTC ACA CCC CTG
Glu Arg Asp Phe Ile His Thr Ala Ser Leu Ser Phe Leu Thr Pro Leu>

440                 450                 460                 470                 480
CGG AAC TTC CTA GAG GGG GAC TGG AAA ACG ATT TCG AAG GAG AGG CGG
Arg Asn Phe Leu Glu Gly Asp Trp Lys Thr Ile Ser Lys Glu Arg Arg>

490                 500                 510                 520
CTC CTG CAG AAC CGG CGT CTT GAC CTG GAT GCC TGC AAA GCC CGG CTA
Leu Leu Gln Asn Arg Arg Leu Asp Leu Asp Ala Cys Lys Ala Arg Leu>
```

FIG. 1D (1 of 3)

```
530             540             550             560             570
AAG AAG GCC AAG GCA GCC GAA GCC AAA GCC ACG ACG GTG CCT GAC TTT
Lys Lys Ala Lys Ala Ala Glu Ala Lys Ala Thr Thr Val Pro Asp Phe>

580             590             600             610             620
CAG GAG ACT AGA CCT CGT AAT TAC ATT CTA TCG GCC AGC GCC TCC GCG
Gln Glu Thr Arg Pro Arg Asn Tyr Ile Leu Ser Ala Ser Ala Ser Ala>

630             640             650             660             670
CTT TGG AAC GAT GAA GTC GAC AAG GCT GAG CAG GAG CTT CGA GTG GCG
Leu Trp Asn Asp Glu Val Asp Lys Ala Glu Gln Glu Leu Arg Val Ala>

680             690             700             710             720
CAG ACA GAG TTT GAC CGG CAG GCA GAA GTG ACC CGT CTC CTG CTG GAG
Gln Thr Glu Phe Asp Arg Gln Ala Glu Val Thr Arg Leu Leu Leu Glu>

730             740             750             760
GGG ATC AGC AGT ACT CAT GTG AAC CAC CTT CAC TGC CTC CAT GAG TTC
Gly Ile Ser Ser Thr His Val Asn His Leu His Cys Leu His Glu Phe>

770             780             790             800             810
GTC AAG TCT CAG ACA ACC TAC TAT GCA CAG TGC TAC CGC CAC ATG CTG
Val Lys Ser Gln Thr Thr Tyr Tyr Ala Gln Cys Tyr Arg His Met Leu>

820             830             840             850             860
GAT CTG CAG AAA CAG CTA GGC AGA TTT CCA GGC ACC TTC GTG GGC ACC
Asp Leu Gln Lys Gln Leu Gly Arg Phe Pro Gly Thr Phe Val Gly Thr>

870             880             890             900             910
ACA GAG CCT GCC TCC CCA CCC CTG AGC AGC ACC TCA CCT ACC ACC ACT
Thr Glu Pro Ala Ser Pro Pro Leu Ser Ser Thr Ser Pro Thr Thr Thr>

920             930             940             950             960
GCG GCC ACC ATG CCT GTG GTA CCT ACT GGG GCT GTC TTG GCC CCT CCA
Ala Ala Thr Met Pro Val Val Pro Thr Gly Ala Val Leu Ala Pro Pro>

970             980             990             1000
GAA GAG GCA GCC CTC TGC CTG GAG GAG GTG GCT CCC CCA GCC AGT GGG
Glu Glu Ala Ala Leu Cys Leu Glu Glu Val Ala Pro Pro Ala Ser Gly>

1010            1020            1030            1040            1050
ACT CGA AAG GCC CGG GTG CTC TAC GAC TAC GAG GCA GCT GAC AGC AGT
Thr Arg Lys Ala Arg Val Leu Tyr Asp Tyr Glu Ala Ala Asp Ser Ser>

1060            1070            1080            1090            1100
GAG CTG GCC CTG CTG GCT GAT GAG CTC ATC ACT GTC TAC AGC CTG CCA
Glu Leu Ala Leu Leu Ala Asp Glu Leu Ile Thr Val Tyr Ser Leu Pro>
```

```
      1110            1120            1130            1140            1150
GGC ATG GAT CCC GAC TGG CTC ATT GGT GAG AGA GGC AAC AAG AAG GGC
Gly Met Asp Pro Asp Trp Leu Ile Gly Glu Arg Gly Asn Lys Lys Gly>

1160            1170            1180
AAG GTT CCT GTC ACC TAC CTG GAA CTT CTC AGC
Lys Val Pro Val Thr Tyr Leu Glu Leu Leu Ser>
```

FIG. 1D (3 of 3)

```
        10          20          30          40
ATG GAC TTC AAC ATG AAG AAG CTG GCG TCG GAC GCG GGC ATC TTC TTC
Met Asp Phe Asn Met Lys Lys Leu Ala Ser Asp Ala Gly Ile Phe Phe>

50          60          70          80          90
ACT CGG GCG GTG CAG TTC ACA GAG GAG AAG TTT GGC CAG GCT GAG AAG
Thr Arg Ala Val Gln Phe Thr Glu Glu Lys Phe Gly Gln Ala Glu Lys>

100         110         120         130         140
ACG GAG CTT GAC GCC CAC TTT GAA AAC CTC CTA GCT CGG GCA GAC AGC
Thr Glu Leu Asp Ala His Phe Glu Asn Leu Leu Ala Arg Ala Asp Ser>

150         160         170         180         190
ACC AAG AAC TGG ACA GAG CGG ATC CTG AGG CAG ACC GAG GTG CTG CTG
Thr Lys Asn Trp Thr Glu Arg Ile Leu Arg Gln Thr Glu Val Leu Leu>

200         210         220         230         240
CAG CCC AAC CCC AGT GCT CGA GTG GAG GAG TTC CTA TAT GAG AAG CTG
Gln Pro Asn Pro Ser Ala Arg Val Glu Glu Phe Leu Tyr Glu Lys Leu>

250         260         270         280
GAC AGA AAG GTG CCC TCG AGA GTC ACC AAT GGG GAG CTG CTG GCT CAG
Asp Arg Lys Val Pro Ser Arg Val Thr Asn Gly Glu Leu Leu Ala Gln>

290         300         310         320         330
TAC ATG GCG GAG GCA GCC AGC GAG CTG GGC CCC AGC ACT CCC TAC GGG
Tyr Met Ala Glu Ala Ala Ser Glu Leu Gly Pro Ser Thr Pro Tyr Gly>

340         350         360         370         380
AAG ACG CTG ATC AAG GTG TCA GAA GCT GAG AAG CGC CTC GGA GCA GCA
Lys Thr Leu Ile Lys Val Ser Glu Ala Glu Lys Arg Leu Gly Ala Ala>

390         400         410         420         430
GAG CGG GAT TTC ATT CAC ACT GCC TCC CTC AGC TTC CTC ACA CCC CTG
Glu Arg Asp Phe Ile His Thr Ala Ser Leu Ser Phe Leu Thr Pro Leu>

440         450         460         470         480
CGG AAC TTC CTA GAG GGG GAC TGG AAA ACG ATT TCG AAG GAG AGG CGG
Arg Asn Phe Leu Glu Gly Asp Trp Lys Thr Ile Ser Lys Glu Arg Arg>

490         500         510         520
CTC CTG CAG AAC CGG CGT CTT GAC CTG GAT GCC TGC AAA GCC CGG CTA
Leu Leu Gln Asn Arg Arg Leu Asp Leu Asp Ala Cys Lys Ala Arg Leu>
```

FIG. 1E (1 of 3)

```
530             540             550             560             570
AAG AAG GCC AAG GCA GCC GAA GCC AAA GCC ACG ACG GTG CCT GAC TTT
Lys Lys Ala Lys Ala Ala Glu Ala Lys Ala Thr Thr Val Pro Asp Phe>

580             590             600             610             620
CAG GAG ACT AGA CCT CGT AAT TAC ATT CTA TCG GCC AGC GCC TCC GCG
Gln Glu Thr Arg Pro Arg Asn Tyr Ile Leu Ser Ala Ser Ala Ser Ala>

630             640             650             660             670
CTT TGG AAC GAT GAA GTC GAC AAG GCT GAG CAG GAG CTT CGA GTG GCG
Leu Trp Asn Asp Glu Val Asp Lys Ala Glu Gln Glu Leu Arg Val Ala>

680             690             700             710             720
CAG ACA GAG TTT GAC CGG CAG GCA GAA GTG ACC CGT CTC CTG CTG GAG
Gln Thr Glu Phe Asp Arg Gln Ala Glu Val Thr Arg Leu Leu Leu Glu>

730             740             750             760
GGG ATC AGC AGT ACT CAT GTG AAC CAC CTT CGC TGC CTC CAT GAG TTC
Gly Ile Ser Ser Thr His Val Asn His Leu Arg Cys Leu His Glu Phe>

770             780             790             800             810
GTC AAG TCT CAG ACA ACC TAC TAT GCA CAG TGC TAC CGC CAC ATG CTG
Val Lys Ser Gln Thr Thr Tyr Tyr Ala Gln Cys Tyr Arg His Met Leu>

820             830             840             850             860
GAT CTG CAG AAA CAG CTA GGC AGA TTT CCA GGC ACC TTC GTG GGC ACC
Asp Leu Gln Lys Gln Leu Gly Arg Phe Pro Gly Thr Phe Val Gly Thr>

870             880             890             900             910
ACA GAG CCT GCC TCC CCA CCC CTG AGC AGC ACC TCA CCT ACC ACC ACT
Thr Glu Pro Ala Ser Pro Pro Leu Ser Ser Thr Ser Pro Thr Thr Thr>

920             930             940             950             960
GCG GCC ACC ATG CCT GTG GTA CCT ACT GGG GCT GTC TTG GCC CCT CCA
Ala Ala Thr Met Pro Val Val Pro Thr Gly Ala Val Leu Ala Pro Pro>

970             980             990            1000
GAA GAG GCA GCC CTC TGC CTG GAG GAG GTG GCT CCC CCA GCC AGT GGG
Glu Glu Ala Ala Leu Cys Leu Glu Glu Val Ala Pro Pro Ala Ser Gly>

1010            1020            1030            1040            1050
ACT CGA AAG GCC CGG GTG CTC TAC GAC TAC GAG GCA GCT GAC AGC AGT
Thr Arg Lys Ala Arg Val Leu Tyr Asp Tyr Glu Ala Ala Asp Ser Ser>

1060            1070            1080            1090            1100
GAG CTG GCC CTG CTG GCT GAT GAG CTC ATC ACT GTC TAC AGC CTG CCA
Glu Leu Ala Leu Leu Ala Asp Glu Leu Ile Thr Val Tyr Ser Leu Pro>
```

```
      1110          1120          1130          1140          1150
GGC ATG GAT CCC GAC TGG CTC ATT GGT GAG AGA GGC AAC AAG AAG GGC
Gly Met Asp Pro Asp Trp Leu Ile Gly Glu Arg Gly Asn Lys Lys Gly>

1160          1170          1180
AAG GTT CCT GTC ACC TAC CTG GAA CTT CTC AGC
Lys Val Pro Val Thr Tyr Leu Glu Leu Leu Ser>
```

FIG. 1E (3 of 3)

| | | 10 | 20 | 30 | 40 |
|---|---|---|---|---|---|
| SPAS-1 (T) | | A T G G A C T T C A A C A T G A A G A A G C T G G C G T C G G A C G C G G G C A |
| SPAS-1 (N) | | A T G G A C T T C A A C A T G A A G A A G C T G G C G T C G G A C G C G G G C A |

| | | 50 | 60 | 70 | 80 |
|---|---|---|---|---|---|
| SPAS-1 (T) | | T C T T C T T C A C T C G G G C G G T G C A G T T C A C A G A G G A G A A G T T |
| SPAS-1 (N) | | T C T T C T T C A C T C G G G C G G T G C A G T T C A C A G A G G A G A A G T T |

| | | 90 | 100 | 110 | 120 |
|---|---|---|---|---|---|
| SPAS-1 (T) | | T G G C C A G G C T G A G A A G A C G G A G C T T G A C G C C C A C T T T G A A |
| SPAS-1 (N) | | T G G C C A G G C T G A G A A G A C G G A G C T T G A C G C C C A C T T T G A A |

| | | 130 | 140 | 150 | 160 |
|---|---|---|---|---|---|
| SPAS-1 (T) | | A A C C T C C T A G C T C G G G C A G A C A G C A C C A A G A A C T G G A C A G |
| SPAS-1 (N) | | A A C C T C C T A G C T C G G G C A G A C A G C A C C A A G A A C T G G A C A G |

| | | 170 | 180 | 190 | 200 |
|---|---|---|---|---|---|
| SPAS-1 (T) | | A G C G G A T C C T G A G G C A G A C C G A G G T G C T G C T G C A G C C C A A |
| SPAS-1 (N) | | A G C G G A T C C T G A G G C A G A C C G A G G T G C T G C T G C A G C C C A A |

| | | 210 | 220 | 230 | 240 |
|---|---|---|---|---|---|
| SPAS-1 (T) | | C C C C A G T G C T C G A G T G G A G G A G T T C C T A T A T G A G A A G C T G |
| SPAS-1 (N) | | C C C C A G T G C T C G A G T G G A G G A G T T C C T A T A T G A G A A G C T G |

| | | 250 | 260 | 270 | 280 |
|---|---|---|---|---|---|
| SPAS-1 (T) | | G A C A G A A A G G T G C C C T C G A G A G T C A C C A A T G G G G A G C T G C |
| SPAS-1 (N) | | G A C A G A A A G G T G C C C T C G A G A G T C A C C A A T G G G G A G C T G C |

| | | 290 | 300 | 310 | 320 |
|---|---|---|---|---|---|
| SPAS-1 (T) | | T G G C T C A G T A C A T G G C G G A G G C A G C C A G C G A G C T G G G C C C |
| SPAS-1 (N) | | T G G C T C A G T A C A T G G C G G A G G C A G C C A G C G A G C T G G G C C C |

| | | 330 | 340 | 350 | 360 |
|---|---|---|---|---|---|
| SPAS-1 (T) | | C A G C A C T C C C T A C G G G A A G A C G C T G A T C A A G G T G T C A G A A |
| SPAS-1 (N) | | C A G C A C T C C C T A C G G G A A G A C G C T G A T C A A G G T G T C A G A A |

| | | 370 | 380 | 390 | 400 |
|---|---|---|---|---|---|
| SPAS-1 (T) | | G C T G A G A A G C G C C T C G G A G C A G C A G A G C G G G A T T T C A T T C |
| SPAS-1 (N) | | G C T G A G A A G C G C C T C G G A G C A G C A G A G C G G G A T T T C A T T C |

| | | 410 | 420 | 430 | 440 |
|---|---|---|---|---|---|
| SPAS-1 (T) | | A C A C T G C C T C C C T C A G C T T C C T C A C A C C C C T G C G G A A C T T |
| SPAS-1 (N) | | A C A C T G C C T C C C T C A G C T T C C T C A C A C C C C T G C G G A A C T T |

FIG. 1F (1 of 3)

|  | 450 | 460 | 470 | 480 |
|---|---|---|---|---|
| SPAS-1 (T) | C C T A G A G G | G G G A C T G G A A A A | C G A T T T C G A A | G G A G A G G C G G |
| SPAS-1 (N) | C C T A G A G G | G G G A C T G G A A A A | C G A T T T C G A A | G G A G A G G C G G |

|  | 490 | 500 | 510 | 520 |
|---|---|---|---|---|
| SPAS-1 (T) | C T C C T G C A G | A A C C G G C G T C T T | G A C C T G G A T G | C C T G C A A A G |
| SPAS-1 (N) | C T C C T G C A G | A A C C G G C G T C T T | G A C C T G G A T G | C C T G C A A A G |

|  | 530 | 540 | 550 | 560 |
|---|---|---|---|---|
| SPAS-1 (T) | C C C G G C T A A A G A A G G C C A A G G C A G C C G A A G C C A A A G C C A C |
| SPAS-1 (N) | C C C G G C T A A A G A A G G C C A A G G C A G C C G A A G C C A A A G C C A C |

|  | 570 | 580 | 590 | 600 |
|---|---|---|---|---|
| SPAS-1 (T) | G A C G G T G C C T G A C T T T C A G G A G A C T A G A C C T C G T A A T T A C |
| SPAS-1 (N) | G A C G G T G C C T G A C T T T C A G G A G A C T A G A C C T C G T A A T T A C |

|  | 610 | 620 | 630 | 640 |
|---|---|---|---|---|
| SPAS-1 (T) | A T T C T A T C G G C C A G C G C C T C C G C G C T T T G G A A C G A T G A A G |
| SPAS-1 (N) | A T T C T A T C G G C C A G C G C C T C C G C G C T T T G G A A C G A T G A A G |

|  | 650 | 660 | 670 | 680 |
|---|---|---|---|---|
| SPAS-1 (T) | T C G A C A A G G C T G A G C A G G A G C T T C G A G T G G C G C A G A C A G A |
| SPAS-1 (N) | T C G A C A A G G C T G A G C A G G A G C T T C G A G T G G C G C A G A C A G A |

|  | 690 | 700 | 710 | 720 |
|---|---|---|---|---|
| SPAS-1 (T) | G T T T G A C C G G C A G G C A G A A G T G A C C C G T C T C C T G C T G G A G |
| SPAS-1 (N) | G T T T G A C C G G C A G G C A G A A G T G A C C C G T C T C C T G C T G G A G |

|  | 730 | 740 | 750 | 760 |
|---|---|---|---|---|
| SPAS-1 (T) | G G G A T C A G C A G T A C T C A T G T G A A C C A C C T T C | A | C T G C C T C C |
| SPAS-1 (N) | G G G A T C A G C A G T A C T C A T G T G A A C C A C C T T C | G | C T G C C T C C |

|  | 770 | 780 | 790 | 800 |
|---|---|---|---|---|
| SPAS-1 (T) | A T G A G T T C G T C A A G T C T C A G A C A A C C T A C T A T G C A C A G T G |
| SPAS-1 (N) | A T G A G T T C G T C A A G T C T C A G A C A A C C T A C T A T G C A C A G T G |

|  | 810 | 820 | 830 | 840 |
|---|---|---|---|---|
| SPAS-1 (T) | C T A C C G C C A C A T G C T G G A T C T G C A G A A A C A G C T A G G C A G A |
| SPAS-1 (N) | C T A C C G C C A C A T G C T G G A T C T G C A G A A A C A G C T A G G C A G A |

|  | 850 | 860 | 870 | 880 |
|---|---|---|---|---|
| SPAS-1 (T) | T T T C C A G G C A C C T T C G T G G G C A C C A C A G A G C C T G C C T C C C |
| SPAS-1 (N) | T T T C C A G G C A C C T T C G T G G G C A C C A C A G A G C C T G C C T C C C |

|  | 890 | 900 | 910 | 920 |
|---|---|---|---|---|
| SPAS-1 (T) | C A C C C C T G A G C A G C A C C T C A C C T A C C A C C A C T G C G G C C A C |
| SPAS-1 (N) | C A C C C C T G A G C A G C A C C T C A C C T A C C A C C A C T G C G G C C A C |

FIG. 1F (2 of 3)

|          | 930 | 940 | 950 | 960 |
|---|---|---|---|---|
| SPAS-1 (T) | C A T G C C T G T G G T A C C T A C T G G G G C T G T C T T G G C C C C T C C A |
| SPAS-1 (N) | C A T G C C T G T G G T A C C T A C T G G G G C T G T C T T G G C C C C T C C A |

|          | 970 | 980 | 990 | 1000 |
|---|---|---|---|---|
| SPAS-1 (T) | G A A G A G G C A G C C C T C T G C C T G G A G G A G G T G G C T C C C C C A G |
| SPAS-1 (N) | G A A G A G G C A G C C C T C T G C C T G G A G G A G G T G G C T C C C C C A G |

|          | 1010 | 1020 | 1030 | 1040 |
|---|---|---|---|---|
| SPAS-1 (T) | C C A G T G G G A C T C G A A A G G C C C G G G T G C T C T A C G A C T A C G A |
| SPAS-1 (N) | C C A G T G G G A C T C G A A A G G C C C G G G T G C T C T A C G A C T A C G A |

|          | 1050 | 1060 | 1070 | 1080 |
|---|---|---|---|---|
| SPAS-1 (T) | G G C A G C T G A C A G C A G T G A G C T G G C C C T G C T G G C T G A T G A G |
| SPAS-1 (N) | G G C A G C T G A C A G C A G T G A G C T G G C C C T G C T G G C T G A T G A G |

|          | 1090 | 1100 | 1110 | 1120 |
|---|---|---|---|---|
| SPAS-1 (T) | C T C A T C A C T G T C T A C A G C C T G C C A G G C A T G G A T C C C G A C T |
| SPAS-1 (N) | C T C A T C A C T G T C T A C A G C C T G C C A G G C A T G G A T C C C G A C T |

|          | 1130 | 1140 | 1150 | 1160 |
|---|---|---|---|---|
| SPAS-1 (T) | G G C T C A T T G G T G A G A G A G G C A A C A A G A A G G G C A A G G T T C C |
| SPAS-1 (N) | G G C T C A T T G G T G A G A G A G G C A A C A A G A A G G G C A A G G T T C C |

|          | 1170 | 1180 | 1190 | 1200 |
|---|---|---|---|---|
| SPAS-1 (T) | T G T C A C C T A C C T G G A A C T T C T C A G C |
| SPAS-1 (N) | T G T C A C C T A C C T G G A A C T T C T C A G C |

FIG. 1F (3 of 3)

| | | 10 | 20 | 30 | 40 |
|---|---|---|---|---|---|
| mu SPAS-1 (T) | | A T G G A C T T C A A C A T G A A G A A G C T G G C G T C G G A C G C G G G C A | | | |
| hu SPAS-1 | | A T G G A C T T C A A C A T G A A G A A G C T G G C G T C G G A C G C G G G C A | | | |

| | | | 50 | 60 | 70 | 80 |
|---|---|---|---|---|---|---|
| mu SPAS-1 (T) | T C T T C T T C A C | T | C G G G C G G T G C A G T T C A C | A | G A G G A G A A | G | T T |
| hu SPAS-1 | T C T T C T T C A C | C | C G G G C G G T G C A G T T C A C | G | G A G G A G A A | A | T T |

| | | 90 | 100 | 110 | 120 |
|---|---|---|---|---|---|
| mu SPAS-1 (T) | T G G C C A G G C T G A G A A G A C | G | G A G C T T G A | C | G C C C A C T T T G A A |
| hu SPAS-1 | T G G C C A G G C T G A G A A G A C | T | G A G C T T G A | T | G C C C A C T T T G A A |

| | | 130 | | 140 | 150 | 160 |
|---|---|---|---|---|---|---|
| mu SPAS-1 (T) | A A C C T | C | C T | A | G C T | C G G G C A G A C A G C A C C A A G A A C T G G A C A G |
| hu SPAS-1 | A A C C T | T | C T | G | G C C | C G G G C A G A C A G C A C C A A G A A C T G G A C A G |

| | | | 170 | 180 | 190 | 200 |
|---|---|---|---|---|---|---|
| mu SPAS-1 (T) | A G | C G | G A T C | C | T G A G G C A G A C | C | G A G G T G C T G C T G C A G C C C A A |
| hu SPAS-1 | A G | A A | G A T C | T | T G A G G C A G A C | A | G A G G T G C T G C T G C A G C C C A A |

| | | 210 | 220 | 230 | 240 |
|---|---|---|---|---|---|
| mu SPAS-1 (T) | C C C C A G T G C | T | C G A G T G G A G G A G T T C C T | A | T A T G A G A A G C T G |
| hu SPAS-1 | C C C C A G T G C | C | C G A G T G G A G G A G T T C C T | G | T A T G A G A A G C T G |

| | | 250 | | 260 | 270 | 280 |
|---|---|---|---|---|---|---|
| mu SPAS-1 (T) | G A C A G | A | A A G G T | G | C C C T C G | A G | A G T C A C C A A | T | G G G A G C T G C |
| hu SPAS-1 | G A C A G | G | A A G G T | C | C C C T C A | A G | G G T C A C C A A | C | G G G A G C T G C |

| | | 290 | 300 | | 310 | 320 |
|---|---|---|---|---|---|---|
| mu SPAS-1 (T) | T G G C T C A G T A C A T G G C | G | G A | G | C A | G C C A G | C | G A G C T G G G | C | C C |
| hu SPAS-1 | T G G C T C A G T A C A T G G C | A | G A | C | G C | G C C A G T | T | G A G C T G G G | G | C C |

| | | 330 | 340 | 350 | 360 |
|---|---|---|---|---|---|
| mu SPAS-1 (T) | C | A | G | C A C | T | C C C T A | C | G G G A A G A C | G | C T G A T C A A G G T G | T | C A G A A |
| hu SPAS-1 | G | A | C | C A C | C | C C C T A | T | G G G A A G A C | A | C T G A T C A A G G T G | C | C A G A A |

| | | 370 | | 380 | 390 | 400 |
|---|---|---|---|---|---|---|
| mu SPAS-1 (T) | G C T G A | G | A A G C | G | C | C T C | G G A G C | A | G C | A G A G | C | G G A T T T | C | A T | C |
| hu SPAS-1 | G C T G A | A | A A G C | A | A | C T G | G G A G C | C | G C | G G A G | A | G G A T T T | T | A T | C C |

| | | 410 | 420 | 430 | 440 |
|---|---|---|---|---|---|
| mu SPAS-1 (T) | A C A C | T | G C C T C C | C | T C A G C T T C C T C A C A C C C | C | T G C G | G | A A C T T |
| hu SPAS-1 | A C A C | G | G C C T C C | A | T C A G C T T C C T C A C A C C C | T | T G C G | C | A A C T T |

Sequence alignment of mu SPAS-1 (T) and hu SPAS-1, positions 450–920.

| | | | | |
|---|---|---|---|---|
| | 930 | 940 | 950 | 960 |
mu SPAS-1 (T)  C A T G C C T G T G G T A C C T A C T G G G C T G T C T T G G C C C C T C C A
hu SPAS-1     T A T G C C T G T G G T G C C C T C T G T G G C C A G C C T G G C C C C T C C G

| | 970 | 980 | 990 | 1000 |
mu SPAS-1 (T)  G A A G A G G C A G C C C T C T G C C T G G A G G A G G T G G C T C C C C A G
hu SPAS-1     G G G G A G G C C T G C T C T G C C T G G A A G A G G T G G C C C C C C T G

| | 1010 | 1020 | 1030 | 1040 |
mu SPAS-1 (T)  C C A G T G G G A C T C G A A G G C C C G G G T G C T C T A C G A C T A C G A
hu SPAS-1     C C A G T G G G A C C C G C A A A G C T C G G G T G C T C T A T G A C T A C G A

| | 1050 | 1060 | 1070 | 1080 |
mu SPAS-1 (T)  G G C A G C T G A C A G C A G T G A G C T G G C C C T G C T G G C T G A T G A G
hu SPAS-1     G G C A G C C G A C A G C A G T G A G C T G G C C C T G C T G G C T G A T G A G

| | 1090 | 1100 | 1110 | 1120 |
mu SPAS-1 (T)  C T C A T C A C T G T C T A C A G C C T G C C A G G C A T G G A T C C C G A C T
hu SPAS-1     C T C A T C A C T G T C T A C A G C C T G C C T G G C A T G G A C C C T G A C T

| | 1130 | 1140 | 1150 | 1160 |
mu SPAS-1 (T)  G G C T C A T T G G T G A G A G A G G C A A C A A G A A G G G C A A G G T T C C
hu SPAS-1     G G C T C A T T G G C G A G A G A G G C A A C A A G A A G G G C A A G G T C C C

| | 1170 | 1180 | 1190 | 1200 |
mu SPAS-1 (T)  T G T C A C C T A C C T G G A A C T T C T C A G C
hu SPAS-1     T G T C A C C T A C T T G G A A C T G C T C A G C

| | | Tags per million | | Tag counts | Total tags |
|---|---|---|---|---|---|
| | Library name | | | | |
| Brain, Anaplastic | SAGE Duke H1020 | 19 | ○ | 1 | 52371 |
| Prostate Tumor Tissue | SAGE Chen Tumor Pr | 14 | ○ | 1 | 68384 |
| Brain, Glioblastoma (cell line) | SAGE Duke H392 | 17 | ○ | 1 | 57529 |
| Brain, Glioblastoma (primary) | SAGE Duke GBM H1110 | 14 | ○ | 1 | 70061 |
| Colon, Cancer Cell Line | SAGE RKO | 19 | ○ | 1 | 52064 |
| Prostate Tumor Tissue | SAGE PR317 prostate tumor | 15 | ○ | 1 | 65109 |
| Advanced Prostate Tumor | SAGE LN-1 | 131 | ● | 3 | 22835 |

Prediction of HLA-A2-binding human SPAS-1 peptides aa: 1      97    140      201   237              356   395

1 - LLADELITV (LV-9)
2 - YMADAASEL (YL-9)
3 - LLLEGISST (LT-9)
4 - FLTPLRNFL (FL-9)
5 - ILSASASAL (IL-9)

SPAS-1 Derived Epitope P4 (FL-9) is Immunogenic in Humans

SEQUENCE LISTING

```
<160> NUMBER OF SEQ ID NOS: 39

<210> SEQ ID NO 1
<211> LENGTH: 995
<212> TYPE: DNA
<213> ORGANISM: Artificial Sequence
<220> FEATURE:
<223> OTHER INFORMATION: SPAS-1 cDNA
<220> FEATURE:
<221> NAME/KEY: CDS
<222> LOCATION: (1)...(993)

<400> SEQUENCE: 1 ctg gaa agc agt act cat gtg aac cac ctt cac tgc ctc cat gag ttc      48
Leu Glu Ser Ser Thr His Val Asn His Leu His Cys Leu His Glu Phe
 1               5                  10                  15 gtc aag tct cag aca acc tac tat gca cag tgc tac cgc cac atg ctg      96
Val Lys Ser Gln Thr Thr Tyr Tyr Ala Gln Cys Tyr Arg His Met Leu
             20                  25                  30
```

-continued

```
gat ctg cag aaa cag cta ggc aga ttt cca ggc acc ttc gtg ggc acc         144
Asp Leu Gln Lys Gln Leu Gly Arg Phe Pro Gly Thr Phe Val Gly Thr
         35                  40                  45 aca gag cct gcc tcc cca ccc ctg agc agc acc tca cct acc acc act         192
Thr Glu Pro Ala Ser Pro Pro Leu Ser Ser Thr Ser Pro Thr Thr Thr
     50                  55                  60 gcg gcc acc atg cct gtg gta cct act ggg gct gtc ttg gcc cct cca         240
Ala Ala Thr Met Pro Val Val Pro Thr Gly Ala Val Leu Ala Pro Pro
 65                  70                  75                  80 gaa gag gca gcc ctc tgc ctg gag gag gtg gct ccc cca gcc agt ggg         288
Glu Glu Ala Ala Leu Cys Leu Glu Glu Val Ala Pro Pro Ala Ser Gly
                 85                  90                  95 act cga aag gcc cgg gtg ctc tac gac tac gag gca gct gac agc agt         336
Thr Arg Lys Ala Arg Val Leu Tyr Asp Tyr Glu Ala Ala Asp Ser Ser
            100                 105                 110 gag ctg gcc ctg ctg gct gat gag ctc atc act gtc tac agc ctg cca         384
Glu Leu Ala Leu Leu Ala Asp Glu Leu Ile Thr Val Tyr Ser Leu Pro
        115                 120                 125 ggc atg gat ccc gac tgg ctc att ggt gag aga ggc aac aag aag ggc         432
Gly Met Asp Pro Asp Trp Leu Ile Gly Glu Arg Gly Asn Lys Lys Gly
    130                 135                 140 aag gtt cct gtc acc tac ctg gaa ctt ctc agc taa gca gcc cct tcc         480
Lys Val Pro Val Thr Tyr Leu Glu Leu Leu Ser  *  Ala Ala Pro Ser
145                 150                 155 cag gct ctg cca ctt aga gtc gtc tgc tgg cca cag agc tgc tta gga         528
Gln Ala Leu Pro Leu Arg Val Val Cys Trp Pro Gln Ser Cys Leu Gly
160                 165                 170                 175 taa ggg acc taa ccc ttt tct ggc tgt gcc cgt cat tca gct att aaa         576
 *  Gly Thr  *  Pro Phe Ser Gly Cys Ala Arg His Ser Ala Ile Lys
                            180                 185 gag ccc aca aga cag aat ggc ccc agg ccc ctc tgc tag tcc tgc ttc         624
Glu Pro Thr Arg Gln Asn Gly Pro Arg Pro Leu Cys  *  Ser Cys Phe
190                 195                 200 tga cct gca acc ctg cac acc cca ggc ttc cca gct ccc tta agg cag         672
 *  Pro Ala Thr Leu His Thr Pro Gly Phe Pro Ala Pro Leu Arg Gln
        205                 210                 215 aag ggt cac tac att tga cac cac cat ggg ccc agg ata tgc tgg gga         720
Lys Gly His Tyr Ile  *  His His His Gly Pro Arg Ile Cys Trp Gly
220                 225                 230 tgg atg ctc ttg gca tga aag aac atc tgc ctt ctg gct gtg gaa ggt         768
Trp Met Leu Leu Ala  *  Lys Asn Ile Cys Leu Leu Ala Val Glu Gly
235                 240                 245 tga ggg gga cag cag cac aca ggc agg gct agg agt gtg gca gga aac         816
 *  Gly Gly Gln Gln His Thr Gly Arg Ala Arg Ser Val Ala Gly Asn
        250                 255                 260 cag aag ggt cag cca gag cag cag cac caa gtg ctg cct ccc act tcc         864
Gln Lys Gly Gln Pro Glu Gln Gln His Gln Val Leu Pro Pro Thr Ser
265                 270                 275                 280 ctc atg gct ctg gct ggg cac agt ggc tac agc agt cat tcc ttc agt         912
Leu Met Ala Leu Ala Gly His Ser Gly Tyr Ser Ser His Ser Phe Ser
                285                 290                 295 ttc taa cta aca ttc tga cct ctg cct gtc tgc ttg ctc tct ggc aaa         960
Phe  *  Leu Thr Phe  *  Pro Leu Pro Val Cys Leu Leu Ser Gly Lys
            300                 305                 310 taa atc ctt tgt gtg cga aaa aaa aaa aaa aa                              995
 *  Ile Leu Cys Val Arg Lys Lys Lys Lys Lys
                315                 320
```

<210> SEQ ID NO 2
<211> LENGTH: 155

```
<212> TYPE: PRT
<213> ORGANISM: M. musculus

<400> SEQUENCE: 2

Leu Glu Ser Ser Thr His Val Asn His Leu His Cys Leu His Glu Phe
 1               5                  10                  15

Val Lys Ser Gln Thr Thr Tyr Tyr Ala Gln Cys Tyr Arg His Met Leu
                20                  25                  30

Asp Leu Gln Lys Gln Leu Gly Arg Phe Pro Gly Thr Phe Val Gly Thr
            35                  40                  45

Thr Glu Pro Ala Ser Pro Pro Leu Ser Ser Ser Pro Thr Thr Thr
        50                  55                  60

Ala Ala Thr Met Pro Val Val Pro Thr Gly Ala Val Leu Ala Pro Pro
 65                  70                  75                  80

Glu Glu Ala Ala Leu Cys Leu Glu Glu Val Ala Pro Pro Ala Ser Gly
                85                  90                  95

Thr Arg Lys Ala Arg Val Leu Tyr Asp Tyr Glu Ala Ala Asp Ser Ser
            100                 105                 110

Glu Leu Ala Leu Leu Ala Asp Glu Leu Ile Thr Val Tyr Ser Leu Pro
        115                 120                 125

Gly Met Asp Pro Asp Trp Leu Ile Gly Glu Arg Gly Asn Lys Lys Gly
    130                 135                 140

Lys Val Pro Val Thr Tyr Leu Glu Leu Leu Ser
145                 150                 155

<210> SEQ ID NO 3
<211> LENGTH: 20
<212> TYPE: PRT
<213> ORGANISM: Artificial Sequence
<220> FEATURE:
<223> OTHER INFORMATION: SPAS-1 peptides

<400> SEQUENCE: 3

Ala Ala Pro Ser Gln Ala Leu Pro Leu Arg Val Val Cys Trp Pro Gln
 1               5                  10                  15

Ser Cys Leu Gly
            20

<210> SEQ ID NO 4
<211> LENGTH: 2
<212> TYPE: PRT
<213> ORGANISM: Artificial Sequence
<220> FEATURE:
<223> OTHER INFORMATION: SPAS-1 peptides

<400> SEQUENCE: 4

Gly Thr
 1

<210> SEQ ID NO 5
<211> LENGTH: 24
<212> TYPE: PRT
<213> ORGANISM: Artificial Sequence
<220> FEATURE:
<223> OTHER INFORMATION: SPAS-1 peptides

<400> SEQUENCE: 5

Pro Phe Ser Gly Cys Ala Arg His Ser Ala Ile Lys Glu Pro Thr Arg
 1               5                  10                  15

Gln Asn Gly Pro Arg Pro Leu Cys
            20
```

-continued

```
<210> SEQ ID NO 6
<211> LENGTH: 3
<212> TYPE: PRT
<213> ORGANISM: Artificial Sequence
<220> FEATURE:
<223> OTHER INFORMATION: SPAS-1 peptides

<400> SEQUENCE: 6

Ser Cys Phe
 1

<210> SEQ ID NO 7
<211> LENGTH: 20
<212> TYPE: PRT
<213> ORGANISM: Artificial Sequence
<220> FEATURE:
<223> OTHER INFORMATION: SPAS-1 peptides

<400> SEQUENCE: 7

Pro Ala Thr Leu His Thr Pro Gly Phe Pro Ala Pro Leu Arg Gln Lys
 1               5                  10                  15

Gly His Tyr Ile
            20

<210> SEQ ID NO 8
<211> LENGTH: 15
<212> TYPE: PRT
<213> ORGANISM: Artificial Sequence
<220> FEATURE:
<223> OTHER INFORMATION: SPAS-1 peptides

<400> SEQUENCE: 8

His His His Gly Pro Arg Ile Cys Trp Gly Trp Met Leu Leu Ala
 1               5                  10                  15

<210> SEQ ID NO 9
<211> LENGTH: 10
<212> TYPE: PRT
<213> ORGANISM: Artificial Sequence
<220> FEATURE:
<223> OTHER INFORMATION: SPAS-1 peptides

<400> SEQUENCE: 9

Lys Asn Ile Cys Leu Leu Ala Val Glu Gly
 1               5                  10

<210> SEQ ID NO 10
<211> LENGTH: 48
<212> TYPE: PRT
<213> ORGANISM: Artificial Sequence
<220> FEATURE:
<223> OTHER INFORMATION: SPAS-1 peptides

<400> SEQUENCE: 10

Gly Gly Gln Gln His Thr Gly Arg Ala Arg Ser Val Ala Gly Asn Gln
 1               5                  10                  15

Lys Gly Gln Pro Glu Gln Gln His Gln Val Leu Pro Pro Thr Ser Leu
                20                  25                  30

Met Ala Leu Ala Gly His Ser Gly Tyr Ser Ser His Ser Phe Ser Phe
            35                  40                  45

<210> SEQ ID NO 11
<211> LENGTH: 3
<212> TYPE: PRT
```

<213> ORGANISM: Artificial Sequence
<220> FEATURE:
<223> OTHER INFORMATION: SPAS-1 peptides

<400> SEQUENCE: 11

Leu Thr Phe
 1

<210> SEQ ID NO 12
<211> LENGTH: 10
<212> TYPE: PRT
<213> ORGANISM: Artificial Sequence
<220> FEATURE:
<223> OTHER INFORMATION: SPAS-1 peptides

<400> SEQUENCE: 12

Pro Leu Pro Val Cys Leu Leu Ser Gly Lys
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: SPAS-1 peptides

<400> SEQUENCE: 13

Ile Leu Cys Val Arg Lys Lys Lys Lys Lys
 1               5                  10

<210> SEQ ID NO 14
<211> LENGTH: 465
<212> TYPE: DNA
<213> ORGANISM: M. musculus

<400> SEQUENCE: 14
ctggaaagca gtactcatgt gaaccacctt cactgcctcc atgagttcgt caagtctcag    60
acaacctact atgcacagtg ctaccgccac atgctggatc tgcagaaaca gctaggcaga   120
tttccaggca ccttcgtggg caccacagag cctgcctccc acccctgag cagcacctca    180
cctaccacca ctgcggccac catgcctgtg gtacctactg gggctgtctt ggcccctcca   240
gaagaggcag ccctctgcct ggaggaggtg gctcccccag ccagtgggac tcgaaaggcc   300
cgggtgctct acgactacga ggcagctgac agcagtgagc tggccctgct ggctgatgag   360
ctcatcactg tctacagcct gccaggcatg gatcccgact ggctcattgg tgagagaggc   420
aacaagaagg gcaaggttcc tgtcacctac ctggaacttc tcagc                  465

<210> SEQ ID NO 15
<211> LENGTH: 465
<212> TYPE: DNA
<213> ORGANISM: H. sapiens

<400> SEQUENCE: 15
ggaatcagta gcactcacgt gaaccacctg cgctgcctcc acgagttcgt caagtctcag    60
acaacctact acgcacagtg ctaccgccac atgctggact tgcagaagca gctgggcaga   120
tttcccggca ccttcgtggg caccacagag cccgcctccc acccctgag cagcacctca    180
cccaccactg ctgcggccac tatgcctgtg gtgccctctg gccagcct ggcccctccg     240
ggggaggcct cgctctgcct ggaagaggtg gccccccctg ccagtgggac ccgcaaagct   300
cgggtgctct atgactacga ggcagccgac agcagtgagc tggccctgct ggctgatgag   360

```
ctcatcactg tctacagcct gcctggcatg gaccctgact ggctcattgg cgagagaggc    420
aacaagaagg gcaaggtccc tgtcacctac ttggaactgc tcagc                   465
```

<210> SEQ ID NO 16
<211> LENGTH: 155
<212> TYPE: PRT
<213> ORGANISM: M. musculus

<400> SEQUENCE: 16

```
Leu Glu Ser Ser Thr His Val Asn His Leu His Cys Leu His Glu Phe
  1               5                  10                  15

Val Lys Ser Gln Thr Thr Tyr Tyr Ala Gln Cys Tyr Arg His Met Leu
             20                  25                  30

Asp Leu Gln Lys Gln Leu Gly Arg Phe Pro Gly Thr Phe Val Gly Thr
         35                  40                  45

Thr Glu Pro Ala Ser Pro Pro Leu Ser Ser Thr Ser Pro Thr Thr Thr
 50                  55                  60

Ala Ala Thr Met Pro Val Val Pro Thr Gly Ala Val Leu Ala Pro Pro
 65                  70                  75                  80

Glu Glu Ala Ala Leu Cys Leu Glu Glu Val Ala Pro Pro Ala Ser Gly
                 85                  90                  95

Thr Arg Lys Ala Arg Val Leu Tyr Asp Tyr Glu Ala Ala Asp Ser Ser
            100                 105                 110

Glu Leu Ala Leu Leu Ala Asp Glu Leu Ile Thr Val Tyr Ser Leu Pro
        115                 120                 125

Gly Met Asp Pro Asp Trp Leu Ile Gly Glu Arg Gly Asn Lys Lys Gly
    130                 135                 140

Lys Val Pro Val Thr Tyr Leu Glu Leu Leu Ser
145                 150                 155
```

<210> SEQ ID NO 17
<211> LENGTH: 155
<212> TYPE: PRT
<213> ORGANISM: H. sapiens

<400> SEQUENCE: 17

```
Gly Ile Ser Ser Thr His Val Asn His Leu Arg Cys Leu His Glu Phe
  1               5                  10                  15

Val Lys Ser Gln Thr Thr Tyr Tyr Ala Gln Cys Tyr Arg His Met Leu
             20                  25                  30

Asp Leu Gln Lys Gln Leu Gly Arg Phe Pro Gly Thr Phe Val Gly Thr
         35                  40                  45

Thr Glu Pro Ala Ser Pro Pro Leu Ser Ser Thr Ser Pro Thr Thr Ala
 50                  55                  60

Ala Ala Thr Met Pro Val Val Pro Ser Val Ala Ser Leu Ala Pro Pro
 65                  70                  75                  80

Gly Glu Ala Ser Leu Cys Leu Glu Glu Val Ala Pro Pro Ala Ser Gly
                 85                  90                  95

Thr Arg Lys Ala Arg Val Leu Tyr Asp Tyr Glu Ala Ala Asp Ser Ser
            100                 105                 110

Glu Leu Ala Leu Leu Ala Asp Glu Leu Ile Thr Val Tyr Ser Leu Pro
        115                 120                 125

Gly Met Asp Pro Asp Trp Leu Ile Gly Glu Arg Gly Asn Lys Lys Gly
    130                 135                 140

Lys Val Pro Val Thr Tyr Leu Glu Leu Leu Ser
145                 150                 155
```

<210> SEQ ID NO 18
<211> LENGTH: 1185
<212> TYPE: DNA
<213> ORGANISM: Artificial Sequence
<220> FEATURE:
<223> OTHER INFORMATION: TRAMP-C2 Tumor cell cDNA
<220> FEATURE:
<221> NAME/KEY: CDS
<222> LOCATION: (1)...(1185)

<400> SEQUENCE: 18

```
atg gac ttc aac atg aag aag ctg gcg tcg gac gcg ggc atc ttc ttc        48
Met Asp Phe Asn Met Lys Lys Leu Ala Ser Asp Ala Gly Ile Phe Phe
 1               5                  10                  15 act cgg gcg gtg cag ttc aca gag gag aag ttt ggc cag gct gag aag        96
Thr Arg Ala Val Gln Phe Thr Glu Glu Lys Phe Gly Gln Ala Glu Lys
             20                  25                  30 acg gag ctt gac gcc cac ttt gaa aac ctc cta gct cgg gca gac agc       144
Thr Glu Leu Asp Ala His Phe Glu Asn Leu Leu Ala Arg Ala Asp Ser
         35                  40                  45 acc aag aac tgg aca gag cgg atc ctg agg cag acc gag gtg ctg ctg       192
Thr Lys Asn Trp Thr Glu Arg Ile Leu Arg Gln Thr Glu Val Leu Leu
     50                  55                  60 cag ccc aac ccc agt gct cga gtg gag gag ttc cta tat gag aag ctg       240
Gln Pro Asn Pro Ser Ala Arg Val Glu Glu Phe Leu Tyr Glu Lys Leu
 65                  70                  75                  80 gac aga aag gtg ccc tcg aga gtc acc aat ggg gag ctg ctg gct cag       288
Asp Arg Lys Val Pro Ser Arg Val Thr Asn Gly Glu Leu Leu Ala Gln
                 85                  90                  95 tac atg gcg gag gca gcc agc gag ctg ggc ccc agc act ccc tac ggg       336
Tyr Met Ala Glu Ala Ala Ser Glu Leu Gly Pro Ser Thr Pro Tyr Gly
            100                 105                 110 aag acg ctg atc aag gtg tca gaa gct gag aag cgc ctc gga gca gca       384
Lys Thr Leu Ile Lys Val Ser Glu Ala Glu Lys Arg Leu Gly Ala Ala
        115                 120                 125 gag cgg gat ttc att cac act gcc tcc ctc agc ttc ctc aca ccc ctg       432
Glu Arg Asp Phe Ile His Thr Ala Ser Leu Ser Phe Leu Thr Pro Leu
    130                 135                 140 cgg aac ttc cta gag ggg gac tgg aaa acg att tcg aag gag agg cgg       480
Arg Asn Phe Leu Glu Gly Asp Trp Lys Thr Ile Ser Lys Glu Arg Arg
145                 150                 155                 160 ctc ctg cag aac cgg cgt ctt gac ctg gat gcc tgc aaa gcc cgg cta       528
Leu Leu Gln Asn Arg Arg Leu Asp Leu Asp Ala Cys Lys Ala Arg Leu
                165                 170                 175 aag aag gcc aag gca gcc gaa gcc aaa gcc acg acg gtg cct gac ttt       576
Lys Lys Ala Lys Ala Ala Glu Ala Lys Ala Thr Thr Val Pro Asp Phe
            180                 185                 190 cag gag act aga cct cgt aat tac att cta tcg gcc agc gcc tcc gcg       624
Gln Glu Thr Arg Pro Arg Asn Tyr Ile Leu Ser Ala Ser Ala Ser Ala
        195                 200                 205 ctt tgg aac gat gaa gtc gac aag gct gag cag gag ctt cga gtg gcg       672
Leu Trp Asn Asp Glu Val Asp Lys Ala Glu Gln Glu Leu Arg Val Ala
    210                 215                 220 cag aca gag ttt gac cgg cag gca gaa gtg acc cgt ctc ctg ctg gag       720
Gln Thr Glu Phe Asp Arg Gln Ala Glu Val Thr Arg Leu Leu Leu Glu
225                 230                 235                 240 ggg atc agc agt act cat gtg aac cac ctt cac tgc ctc cat gag ttc       768
Gly Ile Ser Ser Thr His Val Asn His Leu His Cys Leu His Glu Phe
                245                 250                 255 gtc aag tct cag aca acc tac tat gca cag tgc tac cgc cac atg ctg       816
Val Lys Ser Gln Thr Thr Tyr Tyr Ala Gln Cys Tyr Arg His Met Leu
```

-continued

```
Val Lys Ser Gln Thr Thr Tyr Tyr Ala Gln Cys Tyr Arg His Met Leu
            260                 265                 270 gat ctg cag aaa cag cta ggc aga ttt cca ggc acc ttc gtg ggc acc       864
Asp Leu Gln Lys Gln Leu Gly Arg Phe Pro Gly Thr Phe Val Gly Thr
        275                 280                 285 aca gag cct gcc tcc cca ccc ctg agc agc acc tca cct acc acc act       912
Thr Glu Pro Ala Ser Pro Pro Leu Ser Ser Thr Ser Pro Thr Thr Thr
    290                 295                 300 gcg gcc acc atg cct gtg gta cct act ggg gct gtc ttg gcc cct cca       960
Ala Ala Thr Met Pro Val Val Pro Thr Gly Ala Val Leu Ala Pro Pro
305                 310                 315                 320 gaa gag gca gcc ctc tgc ctg gag gag gtg gct ccc cca gcc agt ggg      1008
Glu Glu Ala Ala Leu Cys Leu Glu Glu Val Ala Pro Pro Ala Ser Gly
                325                 330                 335 act cga aag gcc cgg gtg ctc tac gac tac gag gca gct gac agc agt      1056
Thr Arg Lys Ala Arg Val Leu Tyr Asp Tyr Glu Ala Ala Asp Ser Ser
            340                 345                 350 gag ctg gcc ctg ctg gct gat gag ctc atc act gtc tac agc ctg cca      1104
Glu Leu Ala Leu Leu Ala Asp Glu Leu Ile Thr Val Tyr Ser Leu Pro
        355                 360                 365 ggc atg gat ccc gac tgg ctc att ggt gag aga ggc aac aag aag ggc      1152
Gly Met Asp Pro Asp Trp Leu Ile Gly Glu Arg Gly Asn Lys Lys Gly
370                 375                 380 aag gtt cct gtc acc tac ctg gaa ctt ctc agc                          1185
Lys Val Pro Val Thr Tyr Leu Glu Leu Leu Ser
385                 390                 395
```

<210> SEQ ID NO 19
<211> LENGTH: 395
<212> TYPE: PRT
<213> ORGANISM: Artificial Sequence
<220> FEATURE:
<223> OTHER INFORMATION: Tumor SPAS-1

<400> SEQUENCE: 19

```
Met Asp Phe Asn Met Lys Lys Leu Ala Ser Asp Ala Gly Ile Phe Phe
 1               5                  10                  15

Thr Arg Ala Val Gln Phe Thr Glu Glu Lys Phe Gly Gln Ala Glu Lys
            20                  25                  30

Thr Glu Leu Asp Ala His Phe Glu Asn Leu Leu Ala Arg Ala Asp Ser
        35                  40                  45

Thr Lys Asn Trp Thr Glu Arg Ile Leu Arg Gln Thr Glu Val Leu Leu
    50                  55                  60

Gln Pro Asn Pro Ser Ala Arg Val Glu Glu Phe Leu Tyr Glu Lys Leu
65                  70                  75                  80

Asp Arg Lys Val Pro Ser Arg Val Thr Asn Gly Glu Leu Leu Ala Gln
                85                  90                  95

Tyr Met Ala Glu Ala Ala Ser Glu Leu Gly Pro Ser Thr Pro Tyr Gly
            100                 105                 110

Lys Thr Leu Ile Lys Val Ser Glu Ala Glu Lys Arg Leu Gly Ala Ala
        115                 120                 125

Glu Arg Asp Phe Ile His Thr Ala Ser Leu Ser Phe Leu Thr Pro Leu
    130                 135                 140

Arg Asn Phe Leu Glu Gly Asp Trp Lys Thr Ile Ser Lys Glu Arg Arg
145                 150                 155                 160

Leu Leu Gln Asn Arg Arg Leu Asp Leu Asp Ala Cys Lys Ala Arg Leu
                165                 170                 175

Lys Lys Ala Lys Ala Ala Glu Ala Lys Ala Thr Thr Val Pro Asp Phe
```

```
                     180                 185                 190
Gln Glu Thr Arg Pro Arg Asn Tyr Ile Leu Ser Ala Ser Ala Ser Ala
                195                 200                 205

Leu Trp Asn Asp Glu Val Asp Lys Ala Glu Gln Glu Leu Arg Val Ala
    210                 215                 220

Gln Thr Glu Phe Asp Arg Gln Ala Glu Val Thr Arg Leu Leu Leu Glu
225                 230                 235                 240

Gly Ile Ser Ser Thr His Val Asn His Leu His Cys Leu His Glu Phe
                    245                 250                 255

Val Lys Ser Gln Thr Thr Tyr Tyr Ala Gln Cys Tyr Arg His Met Leu
                260                 265                 270

Asp Leu Gln Lys Gln Leu Gly Arg Phe Pro Gly Thr Phe Val Gly Thr
                275                 280                 285

Thr Glu Pro Ala Ser Pro Leu Ser Ser Thr Ser Pro Thr Thr Thr
            290                 295                 300

Ala Ala Thr Met Pro Val Val Pro Thr Gly Ala Val Leu Ala Pro Pro
305                 310                 315                 320

Glu Glu Ala Ala Leu Cys Leu Glu Glu Val Ala Pro Ala Ser Gly
                325                 330                 335

Thr Arg Lys Ala Arg Val Leu Tyr Asp Tyr Glu Ala Ala Asp Ser Ser
                340                 345                 350

Glu Leu Ala Leu Leu Ala Asp Glu Leu Ile Thr Val Tyr Ser Leu Pro
                355                 360                 365

Gly Met Asp Pro Asp Trp Leu Ile Gly Glu Arg Gly Asn Lys Lys Gly
                370                 375                 380

Lys Val Pro Val Thr Tyr Leu Glu Leu Leu Ser
385                 390                 395

<210> SEQ ID NO 20
<211> LENGTH: 1185
<212> TYPE: DNA
<213> ORGANISM: Artificial Sequence
<220> FEATURE:
<223> OTHER INFORMATION: Normal SPAS-1 sequence
<220> FEATURE:
<221> NAME/KEY: CDS
<222> LOCATION: (1)...(1185)

<400> SEQUENCE: 20 atg gac ttc aac atg aag aag ctg gcg tcg gac gcg ggc atc ttc ttc     48
Met Asp Phe Asn Met Lys Lys Leu Ala Ser Asp Ala Gly Ile Phe Phe
 1               5                  10                  15 act cgg gcg gtg cag ttc aca gag gag aag ttt ggc cag gct gag aag     96
Thr Arg Ala Val Gln Phe Thr Glu Glu Lys Phe Gly Gln Ala Glu Lys
                20                  25                  30 acg gag ctt gac gcc cac ttt gaa aac ctc cta gct cgg gca gac agc    144
Thr Glu Leu Asp Ala His Phe Glu Asn Leu Leu Ala Arg Ala Asp Ser
            35                  40                  45 acc aag aac tgg aca gag cgg atc ctg agg cag acc gag gtg ctg ctg    192
Thr Lys Asn Trp Thr Glu Arg Ile Leu Arg Gln Thr Glu Val Leu Leu
        50                  55                  60 cag ccc aac ccc agt gct cga gtg gag gag ttc cta tat gag aag ctg    240
Gln Pro Asn Pro Ser Ala Arg Val Glu Glu Phe Leu Tyr Glu Lys Leu
65                  70                  75                  80 gac aga aag gtg ccc tcg aga gtc acc aat ggg gag ctg ctg gct cag    288
Asp Arg Lys Val Pro Ser Arg Val Thr Asn Gly Glu Leu Leu Ala Gln
                85                  90                  95 tac atg gcg gag gca gcc agc gag ctg ggc ccc agc act ccc tac ggg    336
```

```
                Tyr Met Ala Glu Ala Ala Ser Glu Leu Gly Pro Ser Thr Pro Tyr Gly
                        100                 105                 110 aag acg ctg atc aag gtg tca gaa gct gag aag cgc ctc gga gca gca            384
Lys Thr Leu Ile Lys Val Ser Glu Ala Glu Lys Arg Leu Gly Ala Ala
        115                 120                 125 gag cgg gat ttc att cac act gcc tcc ctc agc ttc ctc aca ccc ctg            432
Glu Arg Asp Phe Ile His Thr Ala Ser Leu Ser Phe Leu Thr Pro Leu
130                 135                 140 cgg aac ttc cta gag ggg gac tgg aaa acg att tcg aag gag agg cgg            480
Arg Asn Phe Leu Glu Gly Asp Trp Lys Thr Ile Ser Lys Glu Arg Arg
145                 150                 155                 160 ctc ctg cag aac cgg cgt ctt gac ctg gat gcc tgc aaa gcc cgg cta            528
Leu Leu Gln Asn Arg Arg Leu Asp Leu Asp Ala Cys Lys Ala Arg Leu
                165                 170                 175 aag aag gcc aag gca gcc gaa gcc aaa gcc acg acg gtg cct gac ttt            576
Lys Lys Ala Lys Ala Ala Glu Ala Lys Ala Thr Thr Val Pro Asp Phe
            180                 185                 190 cag gag act aga cct cgt aat tac att cta tcg gcc agc gcc tcc gcg            624
Gln Glu Thr Arg Pro Arg Asn Tyr Ile Leu Ser Ala Ser Ala Ser Ala
        195                 200                 205 ctt tgg aac gat gaa gtc gac aag gct gag cag gag ctt cga gtg gcg            672
Leu Trp Asn Asp Glu Val Asp Lys Ala Glu Gln Glu Leu Arg Val Ala
210                 215                 220 cag aca gag ttt gac cgg cag gca gaa gtg acc cgt ctc ctg ctg gag            720
Gln Thr Glu Phe Asp Arg Gln Ala Glu Val Thr Arg Leu Leu Leu Glu
225                 230                 235                 240 ggg atc agc agt act cat gtg aac cac ctt cgc tgc ctc cat gag ttc            768
Gly Ile Ser Ser Thr His Val Asn His Leu Arg Cys Leu His Glu Phe
                245                 250                 255 gtc aag tct cag aca acc tac tat gca cag tgc tac cgc cac atg ctg            816
Val Lys Ser Gln Thr Thr Tyr Tyr Ala Gln Cys Tyr Arg His Met Leu
            260                 265                 270 gat ctg cag aaa cag cta ggc aga ttt cca ggc acc ttc gtg ggc acc            864
Asp Leu Gln Lys Gln Leu Gly Arg Phe Pro Gly Thr Phe Val Gly Thr
        275                 280                 285 aca gag cct gcc tcc cca ccc ctg agc agc acc tca cct acc acc act            912
Thr Glu Pro Ala Ser Pro Pro Leu Ser Ser Thr Ser Pro Thr Thr Thr
290                 295                 300 gcg gcc acc atg cct gtg gta cct act ggg gct gtc ttg gcc cct cca            960
Ala Ala Thr Met Pro Val Val Pro Thr Gly Ala Val Leu Ala Pro Pro
305                 310                 315                 320 gaa gag gca gcc ctc tgc ctg gag gag gtg gct ccc cca gcc agt ggg           1008
Glu Glu Ala Ala Leu Cys Leu Glu Glu Val Ala Pro Pro Ala Ser Gly
                325                 330                 335 act cga aag gcc cgg gtg ctc tac gac tac gag gca gct gac agc agt           1056
Thr Arg Lys Ala Arg Val Leu Tyr Asp Tyr Glu Ala Ala Asp Ser Ser
            340                 345                 350 gag ctg gcc ctg ctg gct gat gag ctc atc act gtc tac agc ctg cca           1104
Glu Leu Ala Leu Leu Ala Asp Glu Leu Ile Thr Val Tyr Ser Leu Pro
        355                 360                 365 ggc atg gat ccc gac tgg ctc att ggt gag aga ggc aac aag aag ggc           1152
Gly Met Asp Pro Asp Trp Leu Ile Gly Glu Arg Gly Asn Lys Lys Gly
370                 375                 380 aag gtt cct gtc acc tac ctg gaa ctt ctc agc                                1185
Lys Val Pro Val Thr Tyr Leu Glu Leu Leu Ser
385                 390                 395

<210> SEQ ID NO 21
<211> LENGTH: 395
<212> TYPE: PRT
```

<213> ORGANISM: Artificial Sequence
<220> FEATURE:
<223> OTHER INFORMATION: Normal SPAS-1

<400> SEQUENCE: 21

```
Met Asp Phe Asn Met Lys Lys Leu Ala Ser Asp Ala Gly Ile Phe Phe
 1               5                  10                  15

Thr Arg Ala Val Gln Phe Thr Glu Glu Lys Phe Gly Gln Ala Glu Lys
                20                  25                  30

Thr Glu Leu Asp Ala His Phe Glu Asn Leu Leu Ala Arg Ala Asp Ser
            35                  40                  45

Thr Lys Asn Trp Thr Glu Arg Ile Leu Arg Gln Thr Glu Val Leu Leu
 50                  55                  60

Gln Pro Asn Pro Ser Ala Arg Val Glu Glu Phe Leu Tyr Glu Lys Leu
 65                  70                  75                  80

Asp Arg Lys Val Pro Ser Arg Val Thr Asn Gly Glu Leu Leu Ala Gln
                85                  90                  95

Tyr Met Ala Glu Ala Ala Ser Glu Leu Gly Pro Ser Thr Pro Tyr Gly
                100                 105                 110

Lys Thr Leu Ile Lys Val Ser Glu Ala Glu Lys Arg Leu Gly Ala Ala
            115                 120                 125

Glu Arg Asp Phe Ile His Thr Ala Ser Leu Ser Phe Leu Thr Pro Leu
130                 135                 140

Arg Asn Phe Leu Glu Gly Asp Trp Lys Thr Ile Ser Lys Glu Arg Arg
145                 150                 155                 160

Leu Leu Gln Asn Arg Arg Leu Asp Leu Asp Ala Cys Lys Ala Arg Leu
                165                 170                 175

Lys Lys Ala Lys Ala Ala Glu Ala Lys Ala Thr Thr Val Pro Asp Phe
                180                 185                 190

Gln Glu Thr Arg Pro Arg Asn Tyr Ile Leu Ser Ala Ser Ala Ser Ala
            195                 200                 205

Leu Trp Asn Asp Glu Val Asp Lys Ala Glu Gln Glu Leu Arg Val Ala
210                 215                 220

Gln Thr Glu Phe Asp Arg Gln Ala Glu Val Thr Arg Leu Leu Leu Glu
225                 230                 235                 240

Gly Ile Ser Ser Thr His Val Asn His Leu Arg Cys Leu His Glu Phe
                245                 250                 255

Val Lys Ser Gln Thr Thr Tyr Tyr Ala Gln Cys Tyr Arg His Met Leu
                260                 265                 270

Asp Leu Gln Lys Gln Leu Gly Arg Phe Pro Gly Thr Phe Val Gly Thr
            275                 280                 285

Thr Glu Pro Ala Ser Pro Leu Ser Ser Thr Ser Pro Thr Thr Thr
290                 295                 300

Ala Ala Thr Met Pro Val Val Pro Thr Gly Ala Val Leu Ala Pro Pro
305                 310                 315                 320

Glu Glu Ala Ala Leu Cys Leu Glu Glu Val Ala Pro Pro Ala Ser Gly
                325                 330                 335

Thr Arg Lys Ala Arg Val Leu Tyr Asp Tyr Glu Ala Ala Asp Ser Ser
            340                 345                 350

Glu Leu Ala Leu Leu Ala Asp Glu Leu Ile Thr Val Tyr Ser Leu Pro
                355                 360                 365

Gly Met Asp Pro Asp Trp Leu Ile Gly Glu Arg Gly Asn Lys Lys Gly
            370                 375                 380

Lys Val Pro Val Thr Tyr Leu Glu Leu Leu Ser
```

<210> SEQ ID NO 22
<211> LENGTH: 1185
<212> TYPE: DNA
<213> ORGANISM: Artificial Sequence
<220> FEATURE:
<223> OTHER INFORMATION: Human homolog of SPAS-1

<400> SEQUENCE: 22

```
atggacttca acatgaagaa gctggcgtcg acgcgggca tcttcttcac ccgggcggtg      60
cagttcacgg aggagaaatt tggccaggct gagaagactg agcttgatgc ccactttgaa    120
aaccttctgg cgcgggcaga cagcaccaag aactggacag agaagatctt gaggcagaca    180
gaggtgctgc tgcagcccaa ccccagtgcc cgagtggagg agttcctgta tgagaagctg    240
gacaggaagg tccctcaag ggtcaccaac ggggagctgc tggctcagta catggcagac    300
gcggccagtg agctggggcc gaccaccccc tatgggaaga cactgatcaa ggtggcagaa    360
gctgaaaagc aactgggagc cgcggagagg gatttatcc acacggcctc catcagcttc    420
ctcacaccct gcgcaacttt cctggagggg actggaaga ccatctcgaa ggagaggcgg    480
ctcctccaaa accggcgtct ggacttggat gcctgcaaag cgaggctgaa gaaggccaag    540
gctgcagaag ccaaagccac gacggtgcct gactttcagg agactagacc tcgtaattac    600
attctctcgg ccagcgcctc cgcgctctgg aatgatgaag tggacaaggc cgagcaggag    660
ctccgcgtgg cccagacaga gtttgaccgg caagcagaag tgacccgtct cttgctggag    720
ggaatcagta gcactcacgt gaaccacctg cgctgcctcc acgagttcgt caagtctcag    780
acaacctact acgcacagtg ctaccgccac atgctggact gcagaagca gctgggcaga    840
tttcccggca ccttcgtggg caccacagag cccgcctccc acccctgag cagcacctca    900
cccaccactg ctgcggccac catgcctgtg gtgccctctg tggccagcct ggcccctccg    960
ggggaggcct cgctctgcct ggaagaggtg gccccccctg ccagtgggac ccgcaaagct   1020
cgggtgctct atgactacga ggcagccgac agcagtgagc tggccctgct ggctgatgag   1080
ctcatcactg tctacagcct gcctggcatg gaccctgact ggctcattgg cgagagaggc   1140
aacaagaagg gcaaggtccc tgtcacctac ttggaactgc tcagc                   1185
```

<210> SEQ ID NO 23
<211> LENGTH: 9
<212> TYPE: PRT
<213> ORGANISM: Artificial Sequence
<220> FEATURE:
<223> OTHER INFORMATION: Predicted AA sequence SPAS-1 epitope from
     normal tissue

<400> SEQUENCE: 23

Ser Thr His Val Asn His Leu Arg Cys
 1               5

<210> SEQ ID NO 24
<211> LENGTH: 27
<212> TYPE: DNA
<213> ORGANISM: Artificial Sequence
<220> FEATURE:
<223> OTHER INFORMATION: cDNA of SPAS-1 epitope from normal tissue

<400> SEQUENCE: 24
agtactcatg tgaaccacct tcgctgc                                         27

<210> SEQ ID NO 25
<211> LENGTH: 9
<212> TYPE: PRT
<213> ORGANISM: Artificial Sequence
<220> FEATURE:
<223> OTHER INFORMATION: Predicted AA sequence of SPAS-1 epitope from
      TRAMP-C2 cDNA library

<400> SEQUENCE: 25

Ser Thr His Val Asn His Leu His Cys
 1               5

<210> SEQ ID NO 26
<211> LENGTH: 27
<212> TYPE: DNA
<213> ORGANISM: Artificial Sequence
<220> FEATURE:
<223> OTHER INFORMATION: cDNA of SPAS-1 epitope from TRAMP-C2 cDNA
      library

<400> SEQUENCE: 26
agtactcatg tgaaccacct tcactgc                                         27

<210> SEQ ID NO 27
<211> LENGTH: 10
<212> TYPE: PRT
<213> ORGANISM: Artificial Sequence
<220> FEATURE:
<223> OTHER INFORMATION: SPAS-1(T) Minigene predicted AA sequence

<400> SEQUENCE: 27

Met Ser Thr His Val Asn His Leu His Cys
 1               5                  10

<210> SEQ ID NO 28
<211> LENGTH: 30
<212> TYPE: DNA
<213> ORGANISM: Artificial Sequence
<220> FEATURE:
<223> OTHER INFORMATION: cDNA sequence of SPAS-1(T) Minigene

<400> SEQUENCE: 28
atgagtactc atgtgaacca ccttcactgc                                      30

<210> SEQ ID NO 29
<211> LENGTH: 13
<212> TYPE: PRT
<213> ORGANISM: Artificial Sequence
<220> FEATURE:
<223> OTHER INFORMATION: Predicted AA sequence of SPAS-1(T) from cloned
      cDNA

<400> SEQUENCE: 29

Leu Glu Ser Ser Thr His Val Asn His Leu His Cys Leu
 1               5                  10

<210> SEQ ID NO 30
<211> LENGTH: 36
<212> TYPE: DNA
<213> ORGANISM: Artificial Sequence
<220> FEATURE:
<223> OTHER INFORMATION: SPAS-1(T) sequence from cloned cDNA

<400> SEQUENCE: 30
ctggaaagca gtactcatgt gaaccacctt cactgc                               36

<210> SEQ ID NO 31

<210> SEQ ID NO 31
<211> LENGTH: 10
<212> TYPE: PRT
<213> ORGANISM: Artificial Sequence
<220> FEATURE:
<223> OTHER INFORMATION: Predicted AA sequence of SPAS-1(N) Minigene

<400> SEQUENCE: 31

```
Met Ser Thr His Val Asn His Leu Arg Cys
1               5                   10
```

<210> SEQ ID NO 32
<211> LENGTH: 30
<212> TYPE: DNA
<213> ORGANISM: Artificial Sequence
<220> FEATURE:
<223> OTHER INFORMATION: SPAS-1(N) Minigene cDNA

<400> SEQUENCE: 32
atgagtactc atgtgaacca ccttcgctgc                                    30

<210> SEQ ID NO 33
<211> LENGTH: 1410
<212> TYPE: DNA
<213> ORGANISM: H. sapiens
<220> FEATURE:
<221> NAME/KEY: CDS
<222> LOCATION: (61)...(1248)

<400> SEQUENCE: 33

```
ggctgggccg ggggctgccg gctgcgctcg ggccgtgcgc agcggccgtg cgggcacgcc    60 atg gac ttc aac atg aag aag ctg gcg tcg gac gcg ggc atc ttc ttc    108
Met Asp Phe Asn Met Lys Lys Leu Ala Ser Asp Ala Gly Ile Phe Phe
1               5                   10                  15 acc cgg gcg gtg cag ttc acg gag gag aaa ttt ggc cag gct gag aag    156
Thr Arg Ala Val Gln Phe Thr Glu Glu Lys Phe Gly Gln Ala Glu Lys
                20                  25                  30 act gag ctt gat gcc cac ttt gaa aac ctt ctg gcc cgg gca gac agc    204
Thr Glu Leu Asp Ala His Phe Glu Asn Leu Leu Ala Arg Ala Asp Ser
            35                  40                  45 acc aag aac tgg aca gag aag atc ttg agg cag aca gag gtg ctg ctg    252
Thr Lys Asn Trp Thr Glu Lys Ile Leu Arg Gln Thr Glu Val Leu Leu
        50                  55                  60 cag ccc aac ccc agt gcc cga gtg gag gag ttc ctg tat gag aag ctg    300
Gln Pro Asn Pro Ser Ala Arg Val Glu Glu Phe Leu Tyr Glu Lys Leu
65                  70                  75                  80 gac agg aag gtc ccc tca agg gtc acc aac ggg gag ctg ctg gct cag    348
Asp Arg Lys Val Pro Ser Arg Val Thr Asn Gly Glu Leu Leu Ala Gln
                85                  90                  95 tac atg gca gac gcg gcc agt gag ctg ggg ccg acc acc ccc tat ggg    396
Tyr Met Ala Asp Ala Ala Ser Glu Leu Gly Pro Thr Thr Pro Tyr Gly
                100                 105                 110 aag aca ctg atc aag gtg gca gaa gct gaa aag caa ctg gga gcc gcg    444
Lys Thr Leu Ile Lys Val Ala Glu Ala Glu Lys Gln Leu Gly Ala Ala
            115                 120                 125 gag agg gat ttt atc cac acg gcc tcc atc agc ttc ctc aca ccc ttg    492
Glu Arg Asp Phe Ile His Thr Ala Ser Ile Ser Phe Leu Thr Pro Leu
        130                 135                 140 cgc aac ttc ctg gag ggg gac tgg aag acc atc tcg aag gag agg cgg    540
Arg Asn Phe Leu Glu Gly Asp Trp Lys Thr Ile Ser Lys Glu Arg Arg
145                 150                 155                 160 ctc ctc caa aac cgg cgt ctg gac ttg gat gcc tgc aaa gcg agg ctg    588
Leu Leu Gln Asn Arg Arg Leu Asp Leu Asp Ala Cys Lys Ala Arg Leu
                165                 170                 175
```

```
aag aag gcc aag gct gca gaa gcc aaa gcc acg acg gtg cct gac ttt    636
Lys Lys Ala Lys Ala Ala Glu Ala Lys Ala Thr Thr Val Pro Asp Phe
        180                 185                 190 cag gag act aga cct cgt aat tac att ctc tcg gcc agc gcc tcc gcg    684
Gln Glu Thr Arg Pro Arg Asn Tyr Ile Leu Ser Ala Ser Ala Ser Ala
    195                 200                 205 ctc tgg aat gat gaa gtg gac aag gcc gag cag gag ctc cgc gtg gcc    732
Leu Trp Asn Asp Glu Val Asp Lys Ala Glu Gln Glu Leu Arg Val Ala
        210                 215                 220 cag aca gag ttt gac cgg caa gca gaa gtg acc cgt ctc ttg ctg gag    780
Gln Thr Glu Phe Asp Arg Gln Ala Glu Val Thr Arg Leu Leu Leu Glu
225                 230                 235                 240 gga atc agt agc act cac gtg aac cac ctg cgc tgc ctc cac gag ttc    828
Gly Ile Ser Ser Thr His Val Asn His Leu Arg Cys Leu His Glu Phe
            245                 250                 255 gtc aag tct cag aca acc tac tac gca cag tgc tac cgc cac atg ctg    876
Val Lys Ser Gln Thr Thr Tyr Tyr Ala Gln Cys Tyr Arg His Met Leu
        260                 265                 270 gac ttg cag aag cag ctg ggc aga ttt ccc ggc acc ttc gtg ggc acc    924
Asp Leu Gln Lys Gln Leu Gly Arg Phe Pro Gly Thr Phe Val Gly Thr
    275                 280                 285 aca gag ccc gcc tcc cca ccc ctg agc agc acc tca ccc acc act gct    972
Thr Glu Pro Ala Ser Pro Pro Leu Ser Ser Thr Ser Pro Thr Thr Ala
290                 295                 300 gcg gcc act atg cct gtg gtg ccc tct gtg gcc agc ctg gcc cct ccg   1020
Ala Ala Thr Met Pro Val Val Pro Ser Val Ala Ser Leu Ala Pro Pro
305                 310                 315                 320 ggg gag gcc tcg ctc tgc ctg gaa gag gtg gcc ccc cct gcc agt ggg   1068
Gly Glu Ala Ser Leu Cys Leu Glu Glu Val Ala Pro Pro Ala Ser Gly
            325                 330                 335 acc cgc aaa gct cgg gtg ctc tat gac tac gag gca gcc gac agc agt   1116
Thr Arg Lys Ala Arg Val Leu Tyr Asp Tyr Glu Ala Ala Asp Ser Ser
        340                 345                 350 gag ctg gcc ctg ctg gct gat gag ctc atc act gtc tac agc ctg cct   1164
Glu Leu Ala Leu Leu Ala Asp Glu Leu Ile Thr Val Tyr Ser Leu Pro
    355                 360                 365 ggc atg gac cct gac tgg ctc att ggc gag aga ggc aac aag aag ggc   1212
Gly Met Asp Pro Asp Trp Leu Ile Gly Glu Arg Gly Asn Lys Lys Gly
370                 375                 380 aag gtc cct gtc acc tac ttg gaa ctg ctc agc tag ctcaaagcca         1258
Lys Val Pro Val Thr Tyr Leu Glu Leu Leu Ser *
385                 390                 395 agtccaagcg gccgcagtct ttacctattc acactcactt tttatctcgg ggttttaatt  1318
tttgctgggg gtttgggttt ataacccaat aaaccgtcct ttgtgtggcg aagtcacctg  1378
gggcttcttg tcaagggccc tgggccttga ag                               1410

<210> SEQ ID NO 34
<211> LENGTH: 395
<212> TYPE: PRT
<213> ORGANISM: H. sapiens

<400> SEQUENCE: 34

Met Asp Phe Asn Met Lys Lys Leu Ala Ser Asp Ala Gly Ile Phe Phe
1               5                   10                  15

Thr Arg Ala Val Gln Phe Thr Glu Glu Lys Phe Gly Gln Ala Glu Lys
            20                  25                  30

Thr Glu Leu Asp Ala His Phe Glu Asn Leu Leu Ala Arg Ala Asp Ser
        35                  40                  45
```

```
Thr Lys Asn Trp Thr Glu Lys Ile Leu Arg Gln Thr Glu Val Leu Leu
         50                   55                  60

Gln Pro Asn Pro Ser Ala Arg Val Glu Glu Phe Leu Tyr Glu Lys Leu
 65                  70                  75                  80

Asp Arg Lys Val Pro Ser Arg Val Thr Asn Gly Glu Leu Leu Ala Gln
             85                  90                  95

Tyr Met Ala Asp Ala Ala Ser Glu Leu Gly Pro Thr Thr Pro Tyr Gly
                100                 105                 110

Lys Thr Leu Ile Lys Val Ala Glu Ala Glu Lys Gln Leu Gly Ala Ala
                115                 120                 125

Glu Arg Asp Phe Ile His Thr Ala Ser Ile Ser Phe Leu Thr Pro Leu
        130                 135                 140

Arg Asn Phe Leu Glu Gly Asp Trp Lys Thr Ile Ser Lys Glu Arg Arg
145                 150                 155                 160

Leu Leu Gln Asn Arg Arg Leu Asp Leu Asp Ala Cys Lys Ala Arg Leu
                165                 170                 175

Lys Lys Ala Lys Ala Ala Glu Ala Lys Ala Thr Thr Val Pro Asp Phe
                180                 185                 190

Gln Glu Thr Arg Pro Arg Asn Tyr Ile Leu Ser Ala Ser Ala Ser Ala
        195                 200                 205

Leu Trp Asn Asp Glu Val Asp Lys Ala Glu Gln Glu Leu Arg Val Ala
    210                 215                 220

Gln Thr Glu Phe Asp Arg Gln Ala Glu Val Thr Arg Leu Leu Leu Glu
225                 230                 235                 240

Gly Ile Ser Ser Thr His Val Asn His Leu Arg Cys Leu His Glu Phe
                245                 250                 255

Val Lys Ser Gln Thr Thr Tyr Tyr Ala Gln Cys Tyr Arg His Met Leu
                260                 265                 270

Asp Leu Gln Lys Gln Leu Gly Arg Phe Pro Gly Thr Phe Val Gly Thr
        275                 280                 285

Thr Glu Pro Ala Ser Pro Leu Ser Ser Thr Ser Pro Thr Thr Ala
    290                 295                 300

Ala Ala Thr Met Pro Val Val Pro Ser Val Ala Ser Leu Ala Pro Pro
305                 310                 315                 320

Gly Glu Ala Ser Leu Cys Leu Glu Glu Val Ala Pro Pro Ala Ser Gly
                325                 330                 335

Thr Arg Lys Ala Arg Val Leu Tyr Asp Tyr Glu Ala Ala Asp Ser Ser
                340                 345                 350

Glu Leu Ala Leu Leu Ala Asp Glu Leu Ile Thr Val Tyr Ser Leu Pro
        355                 360                 365

Gly Met Asp Pro Asp Trp Leu Ile Gly Glu Arg Gly Asn Lys Lys Gly
        370                 375                 380

Lys Val Pro Val Thr Tyr Leu Glu Leu Leu Ser
385                 390                 395

<210> SEQ ID NO 35
<211> LENGTH: 9
<212> TYPE: PRT
<213> ORGANISM: H. sapiens

<400> SEQUENCE: 35

Leu Leu Ala Asp Glu Leu Ile Thr Val
 1               5
```

```
<210> SEQ ID NO 36
<211> LENGTH: 9
<212> TYPE: PRT
<213> ORGANISM: H. sapiens

<400> SEQUENCE: 36

Tyr Met Ala Asp Ala Ala Ser Glu Leu
 1               5

<210> SEQ ID NO 37
<211> LENGTH: 9
<212> TYPE: PRT
<213> ORGANISM: H. sapiens

<400> SEQUENCE: 37

Leu Leu Leu Glu Gly Ile Ser Ser Thr
 1               5

<210> SEQ ID NO 38
<211> LENGTH: 9
<212> TYPE: PRT
<213> ORGANISM: H. sapiens

<400> SEQUENCE: 38

Phe Leu Thr Pro Leu Arg Asn Phe Leu
 1               5

<210> SEQ ID NO 39
<211> LENGTH: 9
<212> TYPE: PRT
<213> ORGANISM: H. sapiens

<400> SEQUENCE: 39

Ile Leu Ser Ala Ser Ala Ser Ala Leu
 1               5
```

DIAGNOSIS OF PROSTATE CANCER WITH SPAS-1 CANCER ANTIGEN

CROSS-REFERENCE TO RELATED APPLICATIONS

This application is a continuation-in-part of U.S. application Ser. No. 09/952,432, filed Sep. 13, 2001, now abandoned, which claims the benefit of U.S. Provisional Patent Application Ser. No. 60/234,472, filed Sep. 21, 2000, the disclosures of which are incorporated herein in their entirety.

This invention was made with Government support under Grant No. 5RO1CA57986-06, awarded by the National Institutes of Health. The Government has certain rights in this invention.

BACKGROUND OF THE INVENTION

The present invention relates generally to therapy and diagnosis of cancer, such as prostate cancer. The invention is more specifically related to polypeptides comprising at least a portion of a SPAS-1 protein, and to polynucleotides encoding such polypeptides. Such polypeptides and polynucleotides can be used in vaccines and pharmaceutical compositions for prevention and treatment of prostate cancer, and for the diagnosis and monitoring of such cancers including but not limited to prostate cancer and other tumors that express this gene. The present invention also relates to methods of identifying and cloning T cell-defined tumor antigens.

Cancer is a significant health problem throughout the world. Although advances have been made in detection and therapy of cancer, no vaccine or other universally successful method for prevention or treatment is currently available. Current therapies, which are generally based on a combination of chemotherapy or surgery and radiation, continue to prove inadequate in many patients.

In North America, prostate cancer is the most common type of cancer and the second leading cause of death from cancer among men. Metastatic prostate cancer is initially treated by androgen deprivation, which has temporary beneficial effects in over 80% of patients. However, despite a variety of hormonal treatments, all patients ultimately develop hormone refractory prostate cancer (HRPC) with a median survival of approximately one-year.

There is a considerable literature demonstrating immunological targets for a few other types of cancer, including notably melanoma. However, there are very few immunological targets for prostate cancer that have been demonstrated in either animal models or in man. Among the few that have been examined, largely on the basis of fairly restricted expression in prostate, are prostate specific antigen (PSA), and prostatic acid phosphase (PAP), and prostate stem cell antigen (PCSA). Although there have been an occasional reports of induction of T cell responses, there have been no documented cases showing strong therapeutic effects of immunization to any of these proteins. Nor have there been any instances of antigens from prostate cancer cells isolated by virtue of their ability to stimulate T cells. It is clearly very desirable to identify additional targets to be used in immunological therapy of prostate cancer, as well as other cancers.

A theme that is emerging in immunological studies of both experimental models in mice and in clinical situations is that immune responses to tumor cells are very often reacted against normal unmutated, normal tissue specific antigens. Many experimental strategies for vaccination against tumors have been devised (see Rosenberg, S., 2000, Development of Cancer Vaccines, ASCO EDUCATIONAL BOOK Spring: 60-62; Logothetis, C., 2000, ASCO EDUCATIONAL BOOK SPRING: 300-302; Khayat, D., 2000, ASCO EDUCATIONAL BOOK Spring: 414-428; Foon, K., 2000, ASCO EDUCATIONAL BOOK Spring: 730-738; see also Restifo, N. and Sznol, M., Cancer Vaccines, Ch. 61, pp. 3023-3043 in DeVita, V. et al. (eds.), 1997, CANCER: PRINCIPLES AND PRACTICE OF ONCOLOGY, Fifth Edition (Lippincott-Raven Publishers, Philadelphia, Pa.). In these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., 1993, Proc. Natl. Acad. Sci U.S.A. 90: 3539-43).

Previous studies have shown that the T cell activation molecule CTLA-4 is an important down regulator of T cells responses (Thompson C. B. and Allison J. P., 1997, Immunity 7:445-50). Further, blockade of CTLA-4 alone or in combination with a variety of types of vaccines can lead to rejection of both immunogenic as well as tumors considered to be non-immunogenic in experimental tumor models such as mammary carcinoma (Hurwitz et al., 1998, supra) and primary prostate cancer (Hurwitz A. et al., 2000, Cancer Research 60: 2444-8). In these instances, non-immunogenic tumors, such as the B16 melanoma, have been rendered susceptible to destruction by the immune system.

One study demonstrated that one could achieve irradication of a murine melanoma B16, an extremely aggressive and non-immunogenic model tumor, by immunizing mice with a vaccine consisting of GM-CSF producing irradiated tumor cells along with CTLA-4 blockade (van Elsas, A et al., 1999, J. Exp. Med. 190:355-66)). Irradication of the tumor was followed development of vitiligo, a progressive depigmentation syndrome often observed in human melanoma patients that undergo spontaneous remission. A peptide was derived from the normal, unmutated trp-2 gene as a major target for the anti-melanoma response. Interestingly, the trp-2 gene has been previously shown to encode a target of T cells regularly detected in human melanoma patients.

In spite of considerable research into therapies for these and other cancers, prostate cancer remains difficult to diagnose and treat effectively. Accordingly, there is a need in the art for improved methods for detecting and treating such cancers. The present invention fulfills these needs and further provides other related advantages.

BRIEF SUMMARY OF THE INVENTION

Compositions and methods are provided for the diagnosis and therapy of cancer, such as prostate cancer. In one aspect, the present invention provides polypeptides comprising at least a portion of a SPAS-1 protein, or variants thereof. Polypeptides of interest for diagnosis and therapy include fragments of the SPAS-1 protein, e.g. the human SPAS-1 protein. Such polypeptides may be fragments of from about 7 amino acids in length to about 20 amino acids in length, including, without limitation the polypeptides (SEQ ID NO:35) LLADELITV (LV-9); (SEQ ID NO:36) YMADAAMSEL (YL-9); (SEQ ID NO:37) LLLEGISST (LT-9); (SEQ ID NO:38) FLTPLRNFL (FL-9); and (SEQ ID NO:39) ILSASASAL (IL-9). For use in diagnosis or therapy, the peptides may be provided as a stable MHC complex. Alternatively, antibodies specific for the SPAS-1 peptide MHC complex, for the SPAS-1 polypeptide or soluble T cell receptors (TCR) specific for the SPAS-1 peptide MHC complex may find use. Such an antibody, peptide, soluble TCR or SPAS-1 peptide MHC complex may be used in a method of determining whether an individual has mounted an immune response against the SPAS-1 antigen, for example by quantitating the presence of T cells immunoreactive with the polypeptide of interest in a patient sample, e.g. a prostate cancer patient sample from blood, lymph, etc. Patient samples may also be evaluated for the expression of SPAS-1 in putative cancer cells, for example by analyzing a sample of such cells for the presence of SPAS-1 encoding mRNA, the presence of SPAS-1 polypeptides, and the like. In such diagnostic methods, the presence of SPAS-1 reactive T cells, mRNA or polypeptide may be compared to a control sample. Such peptides also find use in therapeutic formations, e.g. by administration of an immunologically effective dose of the SPAS-1 polypeptide to an individual.

Within further aspects, the present invention provides methods for inhibiting the development of a cancer in a patient, comprising administering to a patient a pharmaceutical composition or vaccine as described herein, comprising an immunogenic portion of a SPAS-1 polypeptide. The patient can be afflicted a cancer, for example prostate cancer, in which case the methods provide treatment for the disease, or a patient considered at risk for such a disease can be treated prophylactically.

The present invention further provides an isolated SPAS-1 polynucleotide, wherein said polynucleotide may include (a) a polynucleotide that has the sequence as shown in FIG. 1; or (b) a polynucleotide that hybridizes under stringent hybridization conditions to (a) and encodes a polypeptide having the sequence as shown in FIG. 1 or an allelic variant or homologue of a polypeptide having the sequence shown in FIG. 1; or (c) a polynucleotide that hybridizes under stringent hybridization conditions to (a) and encodes a polypeptide with at 15 contiguous residues of the polypeptide shown in FIG. 1; or (d) a polynucleotide that hybridizes under stringent hybridization conditions to (a) and has at least 15 contiguous bases identical to or exactly complementary the sequence shown in FIG. 1. Also included are expression vectors comprising such polynucleotides and host cells transformed or transfected with such expression vectors.

Within other aspects, the present invention provides pharmaceutical compositions comprising SPAS-1 polypeptides or polynucleotides as described herein, and a physiologically acceptable carrier. Within a related aspect of the present invention, vaccines are provided. Such vaccines include, without limitation, a SPAS-1 polypeptide or polynucleotide as described herein and a non-specific immune response enhancer. The SPAS-1 polypeptide may be complexed with an MHC antigen, presented on a cell, including antigen presenting cells, patient cells genetically modified to overexpress SPAS-1; bacterial cells genetically modified to overexpress SPAS-1; viral particles comprising SPAS-1 polypeptides, and the like The present invention further provides pharmaceutical compositions that comprise: a soluble T cell receptor, an antibody or antigen-binding fragment thereof that specifically binds to SPAS-1 or to SPAS-1/MHC complex; and a physiologically acceptable carrier. Within further aspects, the present invention provides pharmaceutical compositions comprising: an antigen presenting cell that expresses a SPAS-1 polypeptide as described above and a pharmaceutically acceptable carrier or excipient. Antigen presenting cells include dendritic cells, macrophages and B cells.

The present invention further provides, within other aspects, methods for removing tumor cells from a biological sample, comprising contacting a biological sample with T cells that specifically react with a SPAS-1 protein or SPAS-1 human homolog protein, wherein the step of contacting is performed under conditions and for a time sufficient to permit the removal of cells expressing the protein from the sample.

Methods are further provided, within other aspects, for stimulating and expanding T cells specific for a SPAS-1 protein or SPAS-1 human homolog, comprising contacting T cells with one or more of. (i) a polypeptide as described above; (ii) a polynucleotide encoding such a polypeptide; and/or (iii) an antigen presenting cell that expresses such a polypeptide; under conditions and for a time sufficient to permit the stimulation and expansion of T cells. Isolated T cell populations comprising T cells prepared as described above are also provided. Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of. (a) incubating $CD4^+$ and/or $CD8^+$ T cells isolated from a patient with one or more of: (i) a polypeptide comprising at least an immunogenic portion of a SPAS-1 human homolog protein; (ii) a polynucleotide encoding such a polypeptide; and (iii) an antigen-presenting cell that expresses such a polypeptide; and (b) administering to the patient an effective amount of the proliferated T cells, and thereby inhibiting the development of a cancer in the patient. Proliferated cells can, but need not be, cloned prior to administration to the patient.

The present invention also provides, within other aspects, methods for monitoring the progression of a cancer in a patient. Such methods comprise the steps of: (a) contacting a biological sample obtained from a patient at a first point in time with a binding agent that binds to a SPAS-1 human homolog polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a SPAS-1 human homolog protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a SPAS-1 human homolog protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

BRIEF DESCRIPTION OF THE DRAWINGS

FIG. 1. Preliminary SPAS-1 cDNA sequence (A-C). (A) (SEQ ID NO: 1) Partial nucleotide and predicted amino acid sequence encoding SPAS-1. The first six nucleotides shown are part of the vector DNA. (B) Nucleotide alignment of the SPAS-1 as shown in FIG. 1A with its human homolog (Accession No. 9910351). The coding region of the partial SPAS-1 cDNA (nucleotides 1-465) was aligned to the DNA segment (nucleotides 783-1245) of the human homolog (Accession No. 9910351) using the Clustal W software (MacVector, Oxford Molecular, Ltd.). The alignment revealed 89% identities at the nucleotide level between SPAS-1 (SEQ ID NO: 14) and its human homolog (SEQ ID NO: 15). (C) The translated SPAS-1 cDNA (amino acids 1-155) (SEQ ID NO: 16) was aligned to the translated DNA of the human homolog (amino acids 261-415) (SEQ ID NO: 17) using the Clustal W software. The alignment revealed 94% identities and 2% similarities at the amino acid level between SPAS-1 and its human homolog. Nucleotide and predicted amino acid sequence of SPAS-1 (D-G); (D) Nucleotide sequence with corresponding predicted amino acid sequence of the full length SPAS-1 cDNA from TRAMP-C2 tumor cells (SEQ ID NO: 18). Nucleotide 6 of the partial sequence (FIG. 1A) (SEQ ID NO: 1) corresponds to nucleotide 727 of the full length SPAS-1 cDNA. (SEQ ID NO: 18) This cDNA is also referred to as Tumor SPAS-1 or SPAS-1 (T). The DNA region of SPAS-1 (T) that contains the antigenic epitope capable of activating TRAMP-specific murine T cells is highlighted. (E) Nucleotide sequence (SEQ ID NO: 20) with corresponding predicted amino acid sequence (SEQ ID NO: 21) of the full length SPAS-1 cDNA from TRAMP-C-2 tumor cells referred to as Normal SPAS-1 or SPAS-1 (N). (F) Nucleotide alignment of SPAS-1 (T) (SEQ ID NO: 18) with SPAS-1 (N) (SEQ ID NO: 20). (G) Nucleotide alignment of the full length mouse SPAS-1 (T) (SEQ ID NO: 18) with its human homolog (Accession No. 9910351) (SEQ ID NO: 22).

FIG. 15. SAGE Tag to gene assignment suggests that SPAS-1 is enriched in a human prostate cancer library.

FIG. 19: Prediction of HLA-A2-binding human SPAS-1 peptides: Human SPAS-1 protein regions containing candidate HLA-A2-binding peptides were predicted with the computer algorithms SYFPEITHI, BIMAS and nHLApred. Five peptides (P1 to P5) were synthesized which had high binding scores according to all three algorithms: P1: (SEQ ID NO:35) LLADELITV (LV-9); P2: (SEQ ID NO:36) YMADAASEL (YL-9); P3: (SEQ ID NO:37) LLLEGISST (LT-9); P4: (SEQ ID NO:38) FLTPLRNFL (FL-9); P5: (SEQ ID NO:39) ILSASASAL (IL-9).

DETAILED DESCRIPTION OF THE INVENTION

Figure 2:
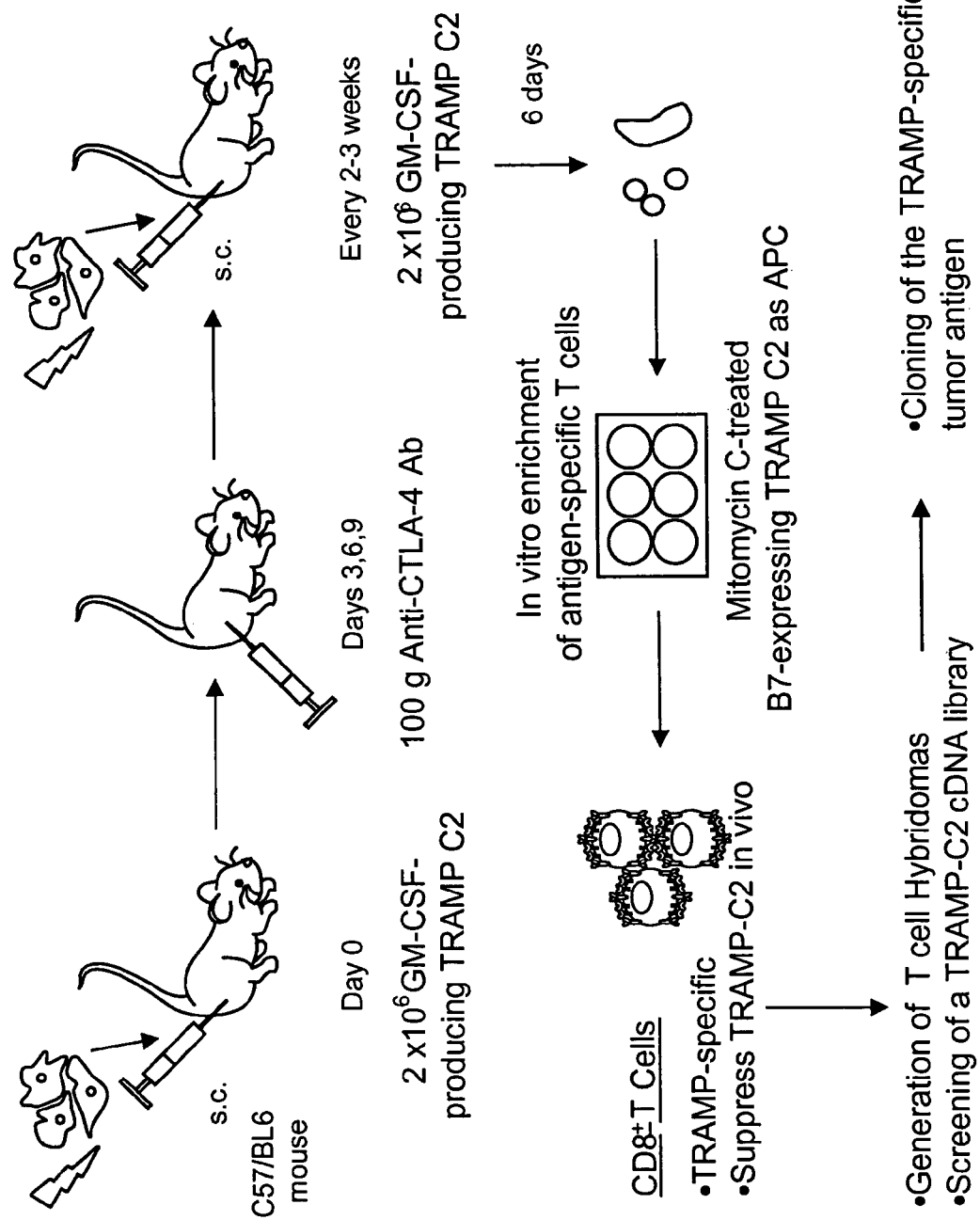
FIG. 2. Generation of anti-TRAMP T cell lines.

The present invention relates to the isolation, via expression cloning using T cells with specificity for prostatic adenocarcinoma cells, of a cDNA termed "SPAS-1," that encodes a T cell antigen, as well as identification of the human homolog. The human polynucleotide or polypeptide may be referred to as "SPAS-1" and "SPAS-1 human homolog". Without intending to be bound to a particular mechanism or limited in any way by type of tumor, the SPAS-1 protein can be used to elicit anti-tumor immune responses that can be exploited in tumor immunotherapy.

In another aspect, the present invention provides methods and reagents for detection of SPAS-1 expression, immune responsiveness against SPAS-1, and the presence of SPAS-1-expressing cells. Abnormal immunoreactivity, expression patterns or expression levels are diagnostic the presence of adenocarcinoma, e.g. of prostate adenocarcinoma.

As noted above, the present invention is generally directed to compositions and methods for the therapy and diagnosis of cancer, such as prostate cancer. The compositions described herein can include prostate tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a SPAS-1 protein or a variant thereof. Certain SPAS-1 proteins are tumor proteins that react detectably (within an immunoassay, such as an ELISA or Western blot) with antisera of a patient afflicted with prostate cancer or other cancers. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells and macrophages that express a polypeptide as described above. T cells that can be employed within such compositions are generally T cells that are specific for a polypeptide as described above.

Figure 1C:
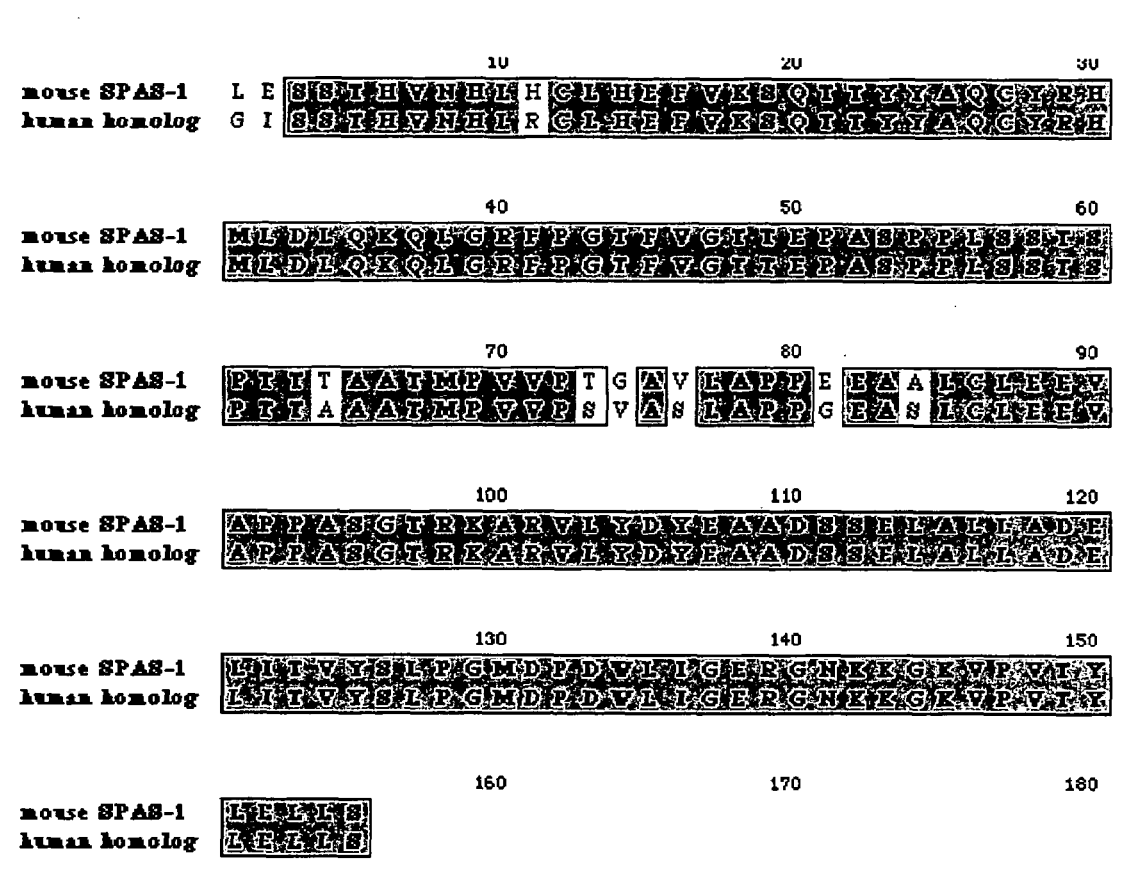
Figure 1G:
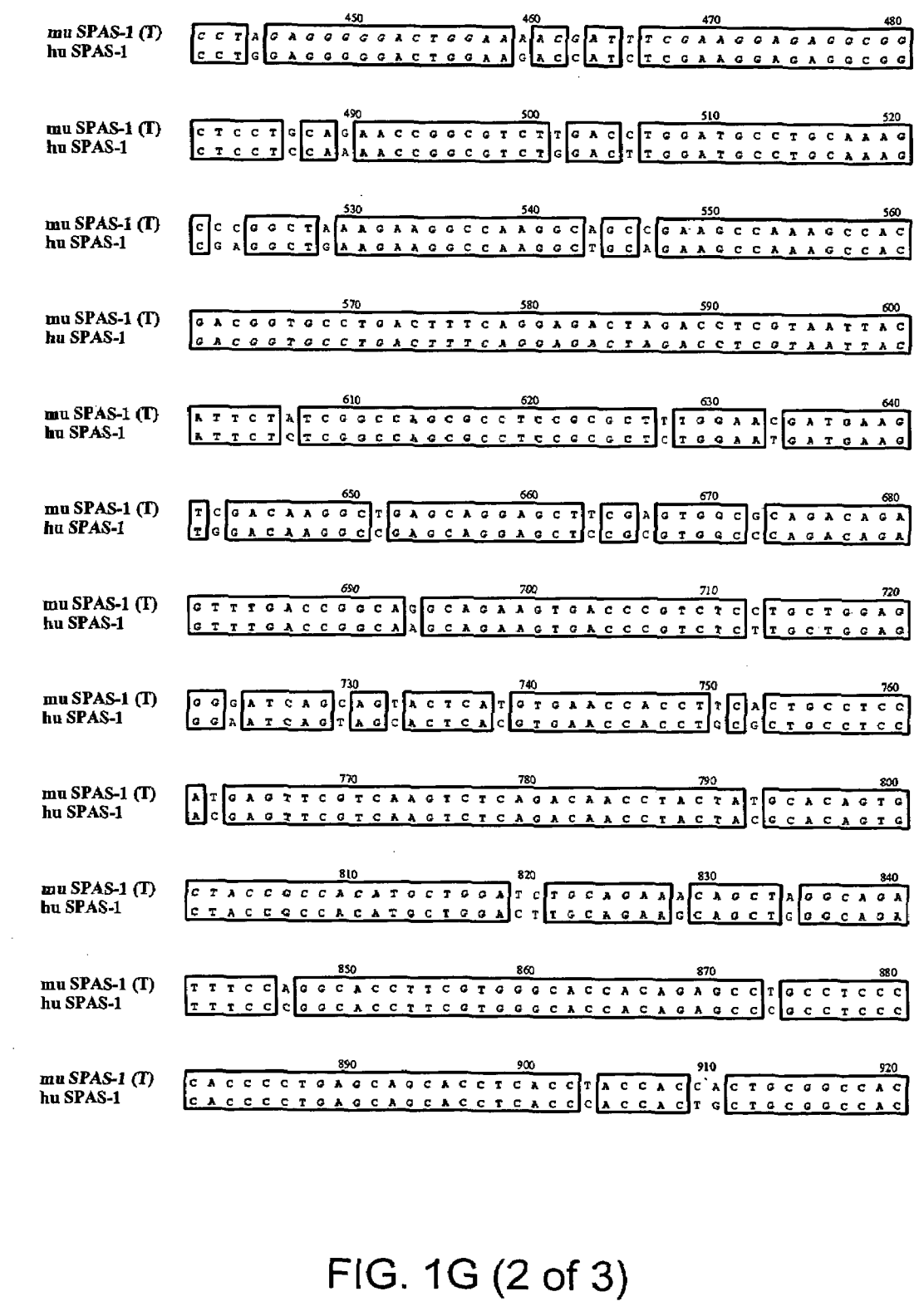

The present invention is based on the discovery of previously unknown mouse gene product, referred to as SPAS-1, expressed in prostate tumor cells, that elicits T cell responses. Partial and full length sequences of polynucleotides encoding SPAS-1 are provided in FIG. 1. FIG. 1 also shows the full length nucleotide and predicted amino acid sequence of SPAS-1. FIG. 1D shows the nucleotide sequence with corresponding predicted amino acid sequence of the full length SPAS-1 cDNA from TRAMP-C2 tumor cells referred to as Tumor SPAS-1 or SPAS-1 (T). The DNA region of SPAS-1 (T) that contains the antigenic epitope capable of activating TRAMP-specific murine T cells is highlighted in FIG. 1D. FIG. 1E shows the nucleotide sequence with corresponding predicted amino acid sequence of the full length SPAS-1 cDNA from TRAMP-C-2 tumor cells referred to as Normal SPAS-1 or SPAS-1 (N). It was cloned both from TRAMP tumor cells as well as from normal tissues (prostate, liver, heart and lung). SPAS-1 (N) differs from SPAS-1 (T) cDNA by one single nucleotide at position 752 (see. FIG. 1F). Nucleotide alignment of the full length mouse SPAS-1 (T) with its human homolog (Accession No. 9910351) is shown in FIG. 1(G).

Mutations in the coding sequence of SPAS-1 or any other gene can have a number of different effects. These effects can include: (1) the generation of new T cell epitopes that might provoke an immune response, and (2) the conferring of oncogenic activity on the gene product. The latter effects could be a result of functional alterations in proteins that regulate, e.g., cell cycle progression and proliferation of the cells, or that play a role in regulating cell death by apoptosis. Changes in function could be either positive or negative and involve acquisition of new activity or loss of normal activity. Examples could include loss of ability to inhibit cell cycle progression or promote cell death, or acquisition of activity that would promote cell cycle progression or that would inhibit cell death. It is possible that mutations that confer oncogenic activity can occur at different positions of the gene in different tumors.

In addition, the invention provides SPAS-1 homologs from other species. The human homolog of SPAS-1 is also shown in FIG. 1. Other SPAS-1 homologs of particular interest include monkey, porcine, ovine, bovine, canine, feline, equine and other primate SPAS-1 homolog proteins. The invention also provides naturally occurring alleles of SPAS-1 and SPAS-1 homologs, and SPAS-1 and SPAS-1 homolog variants as described herein, methods for using SPAS-1 and SPAS-1 homolog polynucleotide, polypeptides, antibodies and other reagents.

SPAS-1 Polynucleotides

Any polynucleotide that encodes a SPAS-1 protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a SPAS-1 protein. More preferably, a polynucleotide encodes an immunogenic portion of a SPAS-1 protein. Polynucleotides complementary to any such sequences are also encompassed by the present invention. Polynucleotides can be single-stranded (coding or antisense) or double-stranded, and can be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences can, but need not, be present within a polynucleotide of the present invention, and a polynucleotide can, but need not, be linked to other molecules and/or support materials.

Polynucleotides can comprise a native sequence (i.e., an endogenous sequence that encodes a SPAS-1 protein or a portion thereof) or can comprise a variant of such a sequence. Polynucleotide variants can contain one or more substitutions, additions, deletions and/or insertions such that the immunogenicity of the encoded polypeptide is not diminished, relative to a native tumor protein (discussed below). The effect on the immunogenicity of the encoded polypeptide can generally be assessed as described herein. Variants preferably exhibit at least about 70% identity, more preferably at least about 80% identity and most preferably at least about 90% identity to a polynucleotide sequence that encodes a native SPAS-1 protein or SPAS-1 homolog, or a portion thereof.

The SPAS-1 and SPAS-1 homolog variants of the invention can contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. SPAS-1 polynucleotide variants can be produced for a variety of reasons, e.g., to optimize codon expression for a particular host (change codons in the human mRNA to those preferred by a bacterial host such as E. coli).

Exemplary SPAS-1 polynucleotide fragments and SPAS-1 homolog polynucleotide fragments, are preferably at least about 15 nucleotides, and more preferably at least about 20 nucleotides, still more preferably at least about 30 nucleotides, and even more preferably, at least about 40 nucleotides in length, or larger 50, 150, 200, 250, 300, 350, 400, 450, 500, 550, 600, 650 nucleotides. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

The term sequence identity refers to a measure of similarity between amino acid or nucleotide sequences, and can be measured using methods known in the art, such as those described below.

The terms "identical" or "percent identity", in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region (see, e.g., SEQ ID NO: 1), when compared and aligned for maximum correspondence over a comparison window, or designated region as measured using one of the following sequence comparison algorithms or by manual alignment and visual inspection.

The phrase "substantially identical," in the context of two nucleic acids or polypeptides, refers to two or more sequences or subsequences that have at least of at least 60%, often at least 70%, preferably at least 80%, most preferably at least 90% or at least 95% nucleotide or amino acid residue identity, when compared and aligned for maximum correspondence, as measured using one of the following sequence comparison algorithms or by visual inspection. Preferably, the substantial identity exists over a region of the sequences that is at least about 50 bases or residues in length, more preferably over a region of at least about 100 bases or residues, and most preferably the sequences are substantially identical over at least about 150 bases or residues. In a most preferred embodiment, the sequences are substantially identical over the entire length of the coding regions.

The percent identity for two polynucleotide or polypeptide sequences can be readily determined by comparing sequences using computer algorithms well known to those of ordinary skill in the art, such as Megalign, using default parameters. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to SPAS-1 nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2: 482), by the homology alignment algorithm of Needleman & 1; 5; Wunsch, 1970, J. Mol. Biol. 48: 443, by the search for similarity method of Pearson & Lipman, 1988, Proc. Natl. Acad. Sci. U.S.A. 85: 2444, by computerized implementations of these algorithms (FASTDB (Intelligenetics), BLAST (National Center for Biomedical Information), GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., 1987 (1999 Suppl.), CURRENT PROTOCOLS IN MOLECULAR BIOLOGY, Greene Publishing Associates and Wiley Interscience, N.Y.)

A preferred example of algorithm that is suitable for determining percent sequence identity and sequence similarity are the BLAST and BLAST 2.0 algorithms, which are described in Altschul et al., 1977, Nuc. Acids Res. 25: 3389-3402 and Altschul et al., 1990, J. Mol. Biol. 215: 403-410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and acomparison of both strands. For amino acid sequences, the BLASTP program uses as defaults a wordlength of 3, and expectation (E) of 10, and the BLOSUM62 scoring matrix (see Henikoff & Henikoff, 1989, Proc. Natl. Acad. Sci. U.S.A. 89:10915) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Natl. Acad. Sc. U.S.A. 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, 1987, J. Mol. Evol. 35: 351-360. The method used is similar to the method described by Higgins & Sharp, 1989, CABIOS 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., 1984, Nuc. Acids Res. 12: 387-395.

Another preferred example of an algorithm that is suitable for multiple DNA and amino acid sequence alignments is the CLUSTALW program (Thompson, J. D. et al., 1994, Nucl. Acids. Res. 22: 4673-4680). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, 1992, Proc. Natl. Acad. Sci. U.S.A. 89:10915-10919).

Variants can also, or alternatively, be substantially homologous to a native gene, or a portion or complement thereof. Such polynucleotide variants are capable of hybridizing under stringent hybridization conditions to a naturally occurring DNA sequence encoding a native SPAS-1 protein (or a complementary sequence). The phrase "stringent hybridization conditions" refers to conditions under which a probe will hybridize, to its target subsequence, typically in a complex mixture of nucleic acid, but not to other sequences. Stringent conditions are sequence-dependent and will be different in different circumstances. Longer sequences hybridize specifically at higher temperatures. An extensive guide to the hybridization of nucleic acids is found in Tijssen, TECHNIQUES IN BIOCHEMISTRY AND MOLECULAR BIOLOGY—HYBRIDIZATION WITH NUCLEIC PROBES, "Overview of principles of hybridization and the strategy of nucleic acid assays" (Elsevier, N.Y. 1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g, greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. An extensive guide to the hybridization of nucleic acids is found in e.g., Sambrook, ed., MOLECULAR CLONING: A LABORATORY MANUAL (2ND EDITION), Vols. 1-3, Cold Spring Harbor Laboratory Press, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, PART I. Theory and Nucleic Acid Preparation, Tijssen, ed. (Elsevier, N.Y. 1993).

For selective or specific hybridization, a positive signal (e.g., identification of a nucleic acid of the invention) is about 10 times background hybridization. "Stringent" hybridization conditions that are used to identify nucleic acids within the scope of the invention include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. In the present invention, genomic DNA or cDNA comprising nucleic acids of the invention can be identified in standard Southern blots under stringent conditions using the nucleic acid sequences disclosed here. Additional stringent conditions for such hybridizations (to identify nucleic acids within the scope of the invention) are those which include a hybridization in a buffer of 40% formamide, 1 M NaCl, 1% SDS at 37° C.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein can, but need not, have an altered structure or function. Alleles can be identified using standard techniques (such as hybridization, amplification and/or database sequence comparison).

Polynucleotides can be prepared using any of a variety of techniques. For example, a polynucleotide can be identified, as described in more detail below, by screening a microarray of cDNAs for tumor-associated expression. Such screens can be performed using a Synteni microarray (Palo Alto, Calif.) according to the manufacturer's instructions (and essentially as described by Schena et al., Proc. Natl. Acad. Sci U.S.A. 93:10614-10619, 1996 and Heller et al., Proc. Natl. Acad. Sci. U.S.A. 94:2150-2155, 1997). Alternatively, polynucleotides can be amplified from cDNA prepared from cells expressing the proteins described herein, such as prostate tumor cells. Such polynucleotides can be amplified via polymerase chain reaction (PCR). For this approach, sequence-specific primers can be designed based on the sequences provided herein, and can be purchased or synthesized.

An amplified portion can be used to isolate a full length gene from a suitable library (e.g., a prostate tumor cDNA library) using well known techniques. Within such techniques, a library (cDNA or genomic) is screened using one or more polynucleotide probes or primers suitable for amplification. Preferably, a library is size-selected to include larger molecules. Random primed libraries can also be preferred for identifying 5' and upstream regions of genes. Genomic libraries are preferred for obtaining introns and extending 5' sequences.

For hybridization techniques, a partial sequence can be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., MOLECULAR CLONING: A LABORATORY MANUAL, Cold Spring Harbor Laboratory Press, Cold Spring Harbor, N.Y., 1989). Hybridizing colonies or plaques are selected and expanded, and the DNA is isolated for further analysis. cDNA clones can be analyzed to determine the amount of additional sequence by, for example, PCR using a primer from the partial sequence and a primer from the vector. Restriction maps and partial sequences can be generated to identify one or more overlapping clones. The complete sequence can then be determined using standard techniques, which can involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits can be used to perform the amplification step. Primers can be designed using, for example, software well known in the art. Primers are preferably 22-30 nucleotides in length, have a GC content of at least 50% and anneal to the target sequence at temperatures of about 68° C. to 72° C. The amplified region can be sequenced as described above, and overlapping sequences assembled into a contiguous sequence.

One such amplification technique is inverse PCR (see Triglia et al., Nuc. Acids Res. 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence can be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., PCR Methods Applic. 1:111-19, 1991) and walking PCR (Parker et al., Nucl. Acids. Res. 19:3055-60, 1991). Other methods employing amplification can also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs can generally be performed using well known programs (e.g., NCBI BLAST searches), and such ESTs can be used to generate a contiguous full length sequence.

Certain nucleic acid sequences of cDNA molecules encoding portions of SPAS-1 proteins are provided in FIG. 1. These polynucleotides were isolated initially by analysis of a cDNA isolated from a murine prostate adenocarcinoma cell library by expression cloning. T cell hybridomas used for the cloning were prepared from T cell lines established from mice immunized by protocols (described below) shown to result in potent anti-tumor immune responses.

Polynucleotide variants can generally be prepared by any method known in the art, including chemical synthesis by, for example, solid phase phosphoramidite chemical synthesis. Modifications in a polynucleotide sequence can also be introduced using standard mutagenesis techniques, such as oligonucleotide-directed site-specific mutagenesis (see Adelman et al., DNA 2:183, 1983). Alternatively, RNA molecules can be generated by in vitro or in vivo transcription of DNA sequences encoding a SPAS-1 protein, or portion thereof, provided that the DNA is incorporated into a vector with a suitable RNA polymerase promoter (such as T7 or SP6). Certain portions can be used to prepare an encoded polypeptide, as described herein. In addition, or alternatively, a portion can be administered to a patient such that the encoded polypeptide is generated in vivo (e.g., by transfecting antigen-presenting cells, such as dendritic cells, with a cDNA construct encoding a prostate tumor polypeptide, and administering the transfected cells to the patient).

A portion of a sequence complementary to a coding sequence (i.e., an antisense polynucleotide) can also be used as a probe or to modulate gene expression. cDNA constructs that can be transcribed into antisense RNA can also be introduced into cells or tissues to facilitate the production of antisense RNA. An antisense polynucleotide can be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al., In Huber and Carr, MOLECULAR AND IMMUNOLOGIC APPROACHES, Futura Publishing Co. (Mt. Kisco, N.Y.; 1994)). Alternatively, an antisense molecule can be designed to hybridize with a control region of a gene (e.g., promoter, enhancer or transcription initiation site), and block transcription of the gene; or to block translation by inhibiting binding of a transcript to ribosomes.

A portion of a coding sequence or of a complementary sequence can also be designed as a probe or primer to detect gene expression. Probes can be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22-30 nucleotides in length.

Any polynucleotide can be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein can be joined to a variety of other nucleotide sequences using established recombinant DNA techniques. For example, a polynucleotide can be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides can be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method can be employed. For example, a polynucleotide can be incorporated into a viral vector such as, but not limited to, adenovirus, adeno-associated virus, retrovirus, or vaccinia or other pox virus (e.g., avian pox virus). The polynucleotides can also be administered as naked plasmid vectors. Techniques for incorporating DNA into such vectors are well known to those of ordinary skill in the art. A retroviral vector can additionally transfer or incorporate a gene for a selectable marker (to aid in the identification or selection of transduced cells) and/or a targeting moiety, such as a gene that encodes a ligand for a receptor on a specific target cell, to render the vector target specific. Targeting can also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

SPAS-1 Polypeptides

Within the context of the present invention, polypeptides can comprise at least an immunogenic portion of a SPAS-1 protein or a variant thereof, as described herein. As noted above, a "SPAS-1 protein" is a protein that is expressed by cancer tumor cells. Proteins that are SPAS-1 proteins also react detectably within an immunoassay (such as an ELISA) with antisera from a patient with prostate cancer. Polypeptides as described herein can be of any length. Additional sequences derived from the native protein and/or heterologous sequences can be present, and such sequences can (but need not) possess further immunogenic or antigenic properties.

An "immunogenic portion," as used herein is a portion of a protein that is recognized (i.e., specifically bound) by a B-cell and/or T-cell surface antigen receptor and results to activation of that B-cell or T-cell. Such immunogenic portions generally comprise at least 5 amino acid residues, more preferably at least 10, and still more preferably at least 20 amino acid residues of a SPAS-1 protein or a variant thereof. Certain preferred immunogenic portions include peptides in which an N-terminal leader sequence and/or transmembrane domain have been deleted. Other preferred immunogenic portions can contain a small N- and/or C-terminal deletion (e.g., 1-30 amino acids, preferably 5-15 amino acids), relative to the mature protein. Other immunogenic peptides include, without limitation, P1: (SEQ ID NO:35) LLADELITV (LV-9); P2: (SEQ ID NO:36) YMADAASEL (YL-9); P3: (SEQ ID NO:37) LLLEGISST (LT-9); P4: (SEQ ID NO:38) FLTPL-RNFL (FL-9); P5: (SEQ ID NO:39) ILSASASAL (IL-9).

Immunogenic portions can generally be identified using well known techniques, such as those summarized in Paul, W. E. (ed.), FUNDAMENTAL IMMUNOLOGY, 3rd ed., 243-247 (Raven Press, 1993) and references cited therein. Such techniques include screening polypeptides for the ability to react with antigen-specific antibodies, antisera and/or T-cell lines or clones. The T cell receptor recognizes a complex structure that requires both a major histocompatibility antigen binding pocket and an antigenic peptide to be present. The binding affinity of T cell receptors is lower than that of antibodies, and will usually be at least about $10^{-4}$ M, more usually at least about $10^{-5}$ M. Methods for determining immunogenicity may include presentation of the epitope in conjunction with an MHC molecule on a cell surface, bead surface, plate surface, as a soluble complex, and the like. T cell responsiveness may include release of cytokines, proliferation, $Ca^{++}$ changes, and the like, as known in the art.

As used herein, antisera and antibodies are "antigen-specific" if they specifically bind to an antigen (i.e., they react with the protein in an ELISA or other immunoassay, and do not react detectably with unrelated proteins). Such antisera and antibodies can be prepared as described herein, and using well known techniques. An immunogenic portion of a native SPAS-1 protein is a portion that reacts with such antisera and/or T-cells at a level that is not substantially less than the reactivity of the full length polypeptide (e.g., in an ELISA and/or T-cell reactivity assay). Such immunogenic portions can react within such assays at a level that is similar to or greater than the reactivity of the fall length polypeptide. Such screens can generally be performed using methods well known to those of ordinary skill in the art, such as those described in Harlow and Lane, 1988, ANTIBODIES: A LABORATORY MANUAL, Cold Spring Harbor Laboratory Press. For example, a polypeptide can be immobilized on a solid support and contacted with patient sera to allow binding of antibodies within the sera to the immobilized polypeptide. Unbound sera can then be removed and bound antibodies detected using, for example, $^{125}$I-labeled Protein A.

An immunogenic portion of a SPAS-1 peptide may be provided a stable complex with an MHC protein. The binding complex may have a wide variety of peptide-MHC combinations. Class I MHC molecules will usually be used to bind $CD8^+$ T cells, and class II will usually be used to bind $CD4^+$ T cells. Non-classical MHC molecules can also be used. The MHC-antigen binding complex comprises monomers or multimers of: an α MHC subunit, a β MHC subunit, and a peptide antigen bound in the cleft formed by the α and β subunits. Complexes of interest may be monomeric, dimeric, trimeric, tetrameric, or higher. In addition, different MHC-peptides can be pooled and spotted together or alternatively, different peptides can be pooled prior to their incorporation into the MHC complex. The MHC proteins may be from any mammalian or avian species, e.g. primate sp., particularly humans; rodents, including mice, rats and hamsters; rabbits; equines, bovines, canines, felines; etc. Of particular interest are the human HLA proteins, and the murine H-2 proteins. Included in the HLA proteins are the class II subunits HLA-DPα, HLA-DPβ, HLA-DQα, HLA-DQβ, HLA-DRα and HLA-DRβ, and the class I proteins HLA-A, HLA-B, HLA-C, and $β_2$-microglobulin. Included in the murine H-2 subunits are the class I H-2K, H-2D, H-2L, and the class II I-A$^α$, I-A$^β$, I-E$^k$, I-E$^α$ and I-E$^β$, and $β_2$-microglobulin. Usually the MHC protein subunits are soluble forms of the membrane-bound protein. Optionally the complexes are labeled. Methods of producing such complexes are known in the art.

Human Class I HLA alleles include, without limitation, HLA-A1 (A*0101); HLA-A2 (A*0206); HLA-A2 (A*0201); HLA-A2 (A*0207); HLA-A2 (A*02011); HLA-A3 (A*0301); HLA-A11 (A*11011); HLA-A24 (A*24021); HLA-A24 (A*2420); HLA-A26 (A*2601); HLA-A26 (A*2603); HLA-A31 (A*31012); HLA-A33 (A*3303); HLA-B7 (B*07021); HLA-B8 (B*0801); HLA-B15 (B*15011); HLA-B35 (B*35011); HLA-B38 (B*3801); HLA-B39 (B*39011); HLA-B40 (B*40012); HLA-B40 (B*4002); HLA-B44 (B*4401); HLA-B44 (B*44031); HLA-B46 (B*4601); HLA-B48 (B*4801); HLA-B51 (B*51011); HLA-B52 (B*52011); HLA-B54 (B*5401); HLA-B55 (B*5502); HLA-B59 (B*5901); HLA-Cw1 (Cw*0102); HLA-Cw1 (Cw*0103); HLA-Cw3 (Cw*03031); HLA-Cw3 (Cw*03041); HLA-Cw4 (Cw*04011); HLA-Cw6 (Cw*0602); HLA-Cw7 (Cw*0702); HLA-Cw8 (Cw*0801); HLA-Cw12 (Cw*12022); HLA-Cw14 (Cw*14021); HLA-Cw14 (Cw*1403); HLA-Cw15 (Cw*15021); HLA-Cx 52 (Cw 12) (Cw*1201); HLA-Cx52 (Cw12) (Cw*1201). Human Class II HLA alleles include, without limitation, HLA-DA alpha 1-4 (pDA alpha 1-4); HLA-DA alpha 1-5 (pDA alpha 1-5); HLA-DA beta 5 (pDA beta 5); HLA-DC alpha 107 (pDC alpha 107); HLA-DO alpha 20 (pDO alpha 20); HLA-DQ beta155 (pDQ beta155); HLA-DR alpha 11 (pDR alpha 11); HLA-DR beta 134 (pDR beta 134); HLA DR beta 5 (TOK H5 DR beta); HLA-DR beta 4 (YT158); HLA-DQA1 (pgDQ4A); HLA-DQB1 (pg DQ1B); HLA-DQB1 (pg DQ1BS); HLA-DRA (DRA2EH); HLA-DPA1 (DPA 02022); HLA-DPB1 (DPB0202); HLA-DRB1 (K^b DRB1 0803); HLA-DRB1 (K^b DRB1 1201); HLA-DRB1 (K^b DRB1 1302); HLA-DRB3 (DRB30301 EMJ-4); HLA-DQA1 (DQA10501 AMALA-4); HLA-DQB1 (DQB10301 AMALA-4); HLA-DQA1 (DQA10101 KAS116 3-6); and HLA-DQB1 (DQB10503 EK2-4).

The antigenic peptide will be from about 6 to about 20 amino acids in length for complexes with class I MHC proteins, usually from about 8 to about 16 amino acids, or from about 9 to about 11 amino acids in length. The peptide will be from about 6 to 25 amino acids in length for complexes with class II MHC proteins, usually from about 10 to 20 amino acids. The epitopic sequence may be empirically determined, by isolating and sequencing peptides bound to native MHC proteins, by synthesis of a series of peptides from the target sequence, then assaying for T cell reactivity to the different peptides, or by producing a series of binding complexes with different peptides and quantitating the T cell binding. The peptides may be prepared in a variety of ways as known in the art.

The peptide MHC complex may be multimerized by through fusion of the MHC portion to a multivalent protein, e.g. immunoglobulin, or by binding the monomers to a multivalent entity through specific attachment sites, as are known in the art. A multimer may also be formed by chemical cross-linking. The attachment site for binding to a multivalent entity may be naturally occurring, or may be introduced through genetic engineering. The site can be a specific binding pair member or one that is modified to provide a specific binding pair member, where the complementary pair has a multiplicity of specific binding sites. Binding to the complementary binding member can be a chemical reaction, epitope-receptor binding or hapten-receptor binding where a hapten is linked to the subunit chain. One of the subunits can be fused to an amino acid sequence providing a recognition site for a modifying enzyme, for example BirA, various glycosylases, farnesyl protein transferase, protein kinases and the like. The subunit may be reacted with the modifying enzyme at any convenient time, usually after formation of the monomer. The group introduced by the modifying enzyme, e.g. biotin, sugar, phosphate, farnesyl, etc. provides a complementary binding pair member, or a unique site for further modification, such as chemical cross-linking, biotinylation, etc. that will provide a complementary binding pair member. Commercially available complexes include biotinylated complexes bound to streptavidin or avidin; and immunoglobulin fusion proteins.

A composition can comprise a variant of a native SPAS-1 protein. A polypeptide "variant," as used herein, is a polypeptide that differs from a native SPAS-1 protein in one or more substitutions, deletions, additions and/or insertions, such that the immunogenicity of the polypeptide is not substantially diminished. In other words, the ability of a variant to react with antigen-specific antisera can be enhanced or unchanged, relative to the native protein, or can be diminished by less than 50%, and preferably less than 20%, relative to the native protein. Such variants can generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the N- and/or C-terminal of the mature protein.

Polypeptide variants preferably exhibit at least about 70%, more preferably at least about 90% and most preferably at least about 95% identity to the native polypeptide. The percent identity can be determined as described above. Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions can generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that can represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant can also, or alternatively, contain nonconservative changes. In a preferred embodiment, variant polypeptides differ from a native sequence by substitution, deletion or addition of five amino acids or fewer. Variants can also (or alternatively) be modified by, for example, the deletion or addition of amino acids that have minimal influence on the immunogenicity, secondary structure and hydropathic nature of the polypeptide.

As noted above, polypeptides can comprise a signal (or leader) sequence at the N-terminal end of the protein, which co-translationally or post-translationally directs transfer of the protein. The polypeptide can also be conjugated to a linker or other sequence for ease of synthesis, purification or identification of the polypeptide (e.g., poly-His), or to enhance binding of the polypeptide to a solid support. For example, a polypeptide can be conjugated to an immunoglobulin Fc region.

Polypeptides can be prepared using any of a variety of well known techniques. Recombinant polypeptides encoded by DNA sequences as described above can be readily prepared from the DNA sequences using any of a variety of expression vectors known to those of ordinary skill in the art. Expression can be achieved in any appropriate host cell that has been transformed or transfected with an expression vector containing a DNA molecule that encodes a recombinant polypeptide. Suitable host cells include prokaryotes, yeast and higher eukaryotic cells, such as mammalian or plant cells. Preferably, the host cells employed are *E. coli*, yeast or a mammalian cell line such as COS or CHO. Supernatants from suitable host/vector systems which secrete recombinant protein or polypeptide into culture media can be first concentrated using a commercially available filter. Following concentration, the concentrate can be applied to a suitable purification matrix such as an affinity matrix or an ion exchange resin. Finally, one or more reverse phase HPLC steps can be employed to further purify a recombinant polypeptide.

Portions and other variants having less than about 100 amino acids, and generally less than about 50 amino acids, can also be generated by synthetic means, using techniques well known to those of ordinary skill in the art. For example, such polypeptides can be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Perkin Elmer/Applied Biosystems Division (Foster City, Calif.), and can be operated according to the manufacturer's instructions.

Within certain specific embodiments, a polypeptide can be a fusion protein that comprises multiple polypeptides as described herein, or that comprises at least one polypeptide as described herein and an unrelated sequence, such as a known tumor protein. A fusion partner can, for example, assist in providing T helper epitopes (an immunological fusion partner), preferably T helper epitopes recognized by humans, or can assist in expressing the protein (an expression enhancer) at higher yields than the native recombinant protein. Certain preferred fusion partners are both immunological and expression enhancing fusion partners. Other fusion partners can be selected so as to increase the solubility of the protein or to enable the protein to be targeted to desired intracellular compartments. Still further fusion partners include affinity tags, which facilitate purification of the protein.

Fusion proteins can generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components can be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence can be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences can be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala can also be used in the linker sequence. Amino acid sequences which can be usefully employed as linkers include those disclosed in Maratea et al., Gene 40:39-46, 1985; Murphy et al., Proc. Natl. Acad. Sci. U.S.A., 1986, 83:8258-8262; U.S. Pat. Nos. 4,935,233 and 4,751,180. The linker sequence can generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Also provided are fusion proteins that comprise a polypeptide as described herein together with an unrelated immunogenic protein. Preferably, the immunogenic protein is capable of eliciting a recall response. Examples of such proteins include tetanus, tuberculosis and hepatitis proteins (see, e.g., Stoute et al., New Engl. J. Med. 336:86-91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100-110 amino acids), and a protein D derivative can be lipidated. Within certain preferred embodiments, the first 109 residues of a Lipoprotein D fusion partner is included on the N-terminus to provide the polypeptide with additional exogenous T-cell epitopes and to increase the expression level in E. coli (thus functioning as an expression enhancer). The lipid tail ensures optimal presentation of the antigen to antigen present cells. Other fusion partners include the non-structural protein from influenzae virus, NS1 (hemaglutinin). Typically, the N-terminal 81 amino acids are used, although different fragments that include T-helper epitopes can be used.

In another embodiment, the immunological fusion partner is the protein known as LYTA, or a portion thereof (preferably a C-terminal portion). LYTA is derived from Streptococcus pneumoniae, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of E. coli C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA can be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. The terms "isolated," or "purified," refer to material that is substantially free from components that normally accompany it as found in its native state (e.g., recombinantly produced or purified away from other cell components with which it is naturally associated). Purity and homogeneity are typically determined using analytical chemistry techniques such as polyacrylamide gel electrophoresis or high performance liquid chromatography. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "nucleic acid" and "polynucleotide" are used interchangeably" and refer to refers to DNA, RNA and nucleic acid polymers containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation; phosphorothioates, phosphoramidates, methyl phosphonates, chiral-methyl phosphonates, 2-O-methyl ribonucleotides, peptide-nucleic acids (PNAs).

The terms "polypeptide," "peptide" and "protein" are used interchangeably herein to refer to a polymer of amino acid residues. The amino acids may be natural amino acids, or include an artificial chemical mimetic of a corresponding naturally occurring amino acid.

SPAS-1 Binding Agents

The present invention further provides agents, such as antibodies and antigen-binding fragments thereof, that specifically bind to a SPAS-1 protein of the SPAS-1 human homolog. The term antibody is used to include intact antibodies and binding fragments thereof. Typically, fragments compete with the intact antibody from which they were derived and with other antibodies for specific binding to an antigen. The term antibody includes polyclonal antibodies, monoclonal antibodies, chimeric antibodies and humanized antibodies, produced by immunization, from hybridomas, or recombinantly.

The term "molecule" is used broadly to mean an organic or inorganic chemical such as a drug; a peptide, including a variant or modified peptide or peptide-like substance such as a peptidomimetic or peptoid; or a protein such as an antibody or a growth factor receptor or a fragment thereof, such as an Fv, Fc or Fab fragment of an antibody, which contains a binding domain. A molecule can be nonnaturally occurring, produced as a result of in vitro methods, or can be naturally occurring, such as a protein or fragment thereof expressed from a cDNA library.

The phrase "specifically (or selectively) binds" to an antibody refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample.

The phrase "specifically bind(s)" or "bind(s) specifically" when referring to a peptide refers to a peptide molecule which has intermediate or high binding affinity, exclusively or predominately, to a target molecule. The phrases "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions may require a binding moiety that is selected for its specificity for a particular target antigen. A variety of assay formats may be used to select ligands that are specifically reactive with a particular protein. For example, solid-phase ELISA immunoassays, immunoprecipitation, Biacore and Western blot are used to identify peptides that specifically react with SPAS-1 domain-containing proteins. Typically a specific or selective reaction will be at least twice background signal or noise and more typically more than 10 times background. Specific binding between a monovalent peptide and a SPAS-1-containing protein means a binding affinity of at least $10^4$ $M^{-1}$, and preferably $10^5$ or $10^6$ $M^{-1}$.

Binding agents can be further capable of differentiating between patients with and without a cancer, such as prostate cancer, using the representative assays provided herein. In other words, antibodies or other binding agents that bind to a SPAS-1 protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, urine and/or tumor biopsies and the like) from patients with and without a cancer (as determined using standard clinical tests) can be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents can be used in combination to improve sensitivity.

Any agent that satisfies the above requirements can be a binding agent. For example, a binding agent can be a ribosome, with or without a peptide component, an RNA molecule or a polypeptide. In a preferred embodiment, a binding agent is an antibody or an antigen-binding fragment thereof. Antibodies can be prepared by any of a variety of techniques known to those of ordinary skill in the art. See, e.g., Harlow and Lane, 1988, ANTIBODIES: A LABORATORY MANUAL, Cold Spring Harbor Laboratory Press. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention can serve as the immunogen without modification. Alternatively, particularly for relatively short polypeptides, a superior immune response can be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide can then be purified from such antisera by, for example, affinity chromatography using the polypeptide coupled to a suitable solid support.

Monoclonal antibodies specific for an antigenic polypeptide of interest can be prepared, for example, using the technique of Kohler and Milstein, Eur. J. Immunol. 6:511-519, 1976, and improvements thereto. Briefly, these methods involve the preparation of immortal cell lines capable of producing antibodies having the desired specificity (i.e., reactivity with the polypeptide of interest). Such cell lines can be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques can be employed. For example, the spleen cells and myeloma cells can be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies can be isolated from the supernatants of growing hybridoma colonies. In addition, various techniques can be employed to enhance the yield, such as injection of the hybridoma cell line into the peritoneal cavity of a suitable vertebrate host, such as a mouse. Monoclonal antibodies can then be harvested from the ascites fluid or the blood. Contaminants can be removed from the antibodies by conventional techniques, such as chromatography, gel filtration, precipitation, and extraction. The polypeptides of this invention can be used in the purification process in, for example, an affinity chromatography step.

Within certain embodiments, the use of antigen-binding fragments of antibodies can be preferred. Such fragments include Fab fragments, which can be prepared using standard techniques. Briefly, immunoglobulins can be purified from rabbit serum by affinity chromatography on Protein A bead columns (Harlow and Lane, 1988, ANTIBODIES: A LABORATORY MANUAL, Cold Spring Harbor Laboratory Press) and digested by papain to yield Fab and Fc fragments. The Fab and Fc fragments can be separated by affinity chromatography on protein A bead columns.

Monoclonal antibodies of the present invention can be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent can be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one can be capable of reacting with a carbonyl-containing group, such as an anhydride or an acid halide, or with an alkyl group containing a good leaving group (e.g., a halide) on the other.

Alternatively, it can be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity can also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), can be employed as the linker group. Coupling can be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it can be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It can be desirable to couple more than one agent to an antibody. In one embodiment, multiple molecules of an agent are coupled to one antibody molecule. In another embodiment, more than one type of agent can be coupled to one antibody. Regardless of the particular embodiment, immunoconjugates with more than one agent can be prepared in a variety of ways. For example, more than one agent can be coupled directly to an antibody molecule, or linkers that provide multiple sites for attachment can be used. Alternatively, a carrier can be used.

A carrier can bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al). A carrier can also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate can be formed from chelating compounds that include those containing nitrogen and sulfur atoms as the donor atoms for binding the metal, or metal oxide, radionuclide. For example, U.S. Pat. No. 4,673,562, to Davison et al., discloses representative chelating compounds and their synthesis.

A variety of routes of administration for the antibodies and immunoconjugates can be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Immunotherapeutic compositions can also, or alternatively, comprise T cells specific for a SPAS-1 protein or SPAS-1 human homolog. Such cells can generally be prepared in vitro or ex vivo, using standard procedures. For example, T cells can be isolated from bone marrow, peripheral blood or a fraction of bone marrow or peripheral blood of a patient, using a commercially available cell separation system, such as the CEPRATE™ system, available from CellPro Inc., Bothell Wash. (see also U.S. Pat. Nos. 5,240,856 and 5,215,926; and PCT applications WO 89/06280; WO 91/16116 and WO 92/07243). Alternatively, T cells can be derived from related or unrelated humans, non-human mammals, cell lines or cultures.

T cells can be stimulated with a prostate tumor polypeptide, polynucleotide encoding a prostate tumor polypeptide and/or an antigen presenting cell (APC) that expresses such a polypeptide. Such stimulation is performed under conditions and for a time sufficient to permit the generation of T cells that are specific for the polypeptide. Preferably, a prostate tumor polypeptide or polynucleotide is present within a delivery vehicle, such as a microsphere, to facilitate the generation of specific T cells.

T cells are considered to be specific for a prostate tumor polypeptide if the T cells kill target cells coated with the polypeptide or expressing a gene encoding the polypeptide. T cell specificity can be evaluated using any of a variety of standard techniques. For example, within a chromium release assay or proliferation assay, a stimulation index of more than two fold increase in lysis and/or proliferation, compared to negative controls, indicates T cell specificity. Such assays can be performed, for example, as described in Chen et al., 1994, Cancer Res. 54:1065-1070. Alternatively, detection of the proliferation of T cells can be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a prostate tumor polypeptide (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-.gamma.) is indicative of T cell activation (see Coligan et al., CURRENT PROTOCOLS IN IMMUNOLOGY, Vol. 1, Wiley Interscience (Greene 1998)). T cells that have been activated in response to a prostate tumor polypeptide, polynucleotide or polypeptide-expressing APC can be $CD4^+$ and/or $CD8^+$. SPAS-1 protein-specific T cells can be expanded using standard techniques. Within preferred embodiments, the T cells are derived from a patient, or from a related or unrelated donor, and are administered to the patient following stimulation and expansion.

For therapeutic purposes, $CD4^+$ or $CD8^+$ T cells that proliferate in response to a prostate tumor polypeptide, polynucleotide or APC can be expanded in number either in vitro or in vivo. Proliferation of such T cells in vitro can be accomplished in a variety of ways. For example, the T cells can be re-exposed to a prostate tumor polypeptide (e.g., a short peptide corresponding to an immunogenic portion of such a polypeptide) with or without the addition of T cell growth factors, such as interleukin-2, and/or stimulator cells that synthesize a prostate tumor polypeptide. Alternatively, one or more T cells that proliferate in the presence of a SPAS-1 protein or SPAS-1 human homolog can be expanded in number by cloning. Methods for cloning cells are well known in the art, and include limiting dilution. Following expansion, the cells can be administered back to the patient as described, for example, by Chang et al., 1996, Crit. Rev. Oncol. Hematol. 22:213.

CTLA-4 blockade is most effective when combined with a vaccination protocol. Many experimental strategies for vaccination against tumors have been devised (see Rosenberg, S., 2000, Development of Cancer Vaccines, ASCO EDUCATIONAL BOOK Spring: 60-62; Logothetis, C., 2000, ASCO EDUCATIONAL BOOK Spring: 300-302; Khayat, D., 2000, ASCO EDUCATIONAL BOOK Spring: 414-428; Foon, K. 2000, ASCO EDUCATIONAL BOOK Spring: 730-738; see also Restifo, N. and Sznol, M., Cancer Vaccines, Ch. 61, pp. 3023-3043 in DeVita, V. et al. (eds.), 1997, CANCER: PRINCIPLES AND PRACTICE OF ONCOLOGY, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al, 1993, Proc. Natl. Acad. Sci U.S.A. 90:3539-43).

Anti-CTLA-4 blockade together with the use of GMCSF-modified tumor cell vaccines has been shown to be effective in a number of experimental tumor models such as mammary carcinoma (Hurwitz et al., 1998, supra), primary prostate cancer (Hurwitz A. et al., 2000, Cancer Research 60: 2444-8) and melanoma (van Elsas, A et al., 1999, J. Exp. Med. 190: 355-66). In these instances, non-immunogenic tumors, such as the B16 melanoma, have been rendered susceptible to destruction by the immune system. The tumor cell vaccine can also be modified to express other immune activators such as IL2, and costimulatory molecules, among others.

CTLA-4 blockade can be used in conjunction with the SPAS-1 proteins of the invention to generate an immune response to these proteins. Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with CTLA-4 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P., 1995, Science 269: 1585-1588; Tamura, Y. et al., 1997, Science 278: 117-120.

Pharmaceutical Compositions and Vaccines

Within certain aspects, polypeptides, including polypeptide MHC complexes as described herein, antibodies specific for SPAS-1 peptide/MHC complex; soluble T cell receptors specific for SPAS-1/MHC complex; polynucleotides, cells expressing or complexed with SPAS-1, T cells and/or binding agents described herein can be incorporated into pharmaceutical compositions or immunogenic compositions (i.e., vaccines). Specific vaccine agents of interest include, without limitation, dendritic cells (peptide pulsed, protein pulsed, RNA transfected, virally infected, bacterial infected, DNA transfected, protein electroporated); dendritophages, activated macrophages; whole cell vaccine (e.g. GVAX); adjuvanted protein (adjuvants, TLR agonists such as CpG, Polyl: C, etc); protein conjugated to TLR agonists; microbial cells expressing SPAS-1, e.g. *Listeria, Salmonella, Clostridium, E. coli*; yeast; viral particles expressing SPAS-1, e.g. adenovirus, alphavirus (Semliki Forest virus, VEE, Sindbis virus, etc), vaccinia virus (Modified ankara virus, MVA); DNA vaccination (naked, gene gun, etc); TCR/MHC complexes; and the like.

Pharmaceutical compositions comprise one or more such compounds and a physiologically acceptable carrier. Vaccines can comprise one or more such compounds and a non-specific immune response enhancer. A non-specific immune response enhancer can be any substance that enhances an immune response to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., VACCINE DESIGN: THE SUBUNIT AND ADJUVANT APPROACH, Plenum Press (NY, 1995). Vaccines can be designed to generate antibody immunity and/or cellular immunity such as that arising from CTL or $CD4^+$ T cells.

Pharmaceutical compositions and vaccines within the scope of the present invention can also contain other compounds, which can be biologically active or inactive. For example, one or more immunogenic portions of other tumor antigens can be present, either incorporated into a fusion polypeptide or as a separate compound, within the composition or vaccine. Polypeptides can, but need not, be conjugated to other macromolecules as described, for example, within U.S. Pat. Nos. 4,372,945 and 4,474,757. Pharmaceutical compositions and vaccines can generally be used for prophylactic and therapeutic purposes.

In prophylactic applications, pharmaceutical compositions or medicaments are administered to a patient susceptible to, or otherwise at risk of a disease or condition (i.e., cancer) in an amount sufficient to eliminate or reduce the risk, lessen the severity, or delay the outset of the disease (including biochemical or histologic), its complications and intermediate pathological phenotypes presenting during development of the disease. In therapeutic applications, compositions or medicaments are administered to a patient suspected of, or already suffering from such a disease in an amount sufficient to cure, or at least partially arrest, the symptoms of the disease (including biochemical or histologic), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

The pharmaceutical compositions of the invention are generally formulated as sterile, substantially isotonic and in full compliance with all Good Manufacturing Practice (GMP) regulations of the U.S. Food and Drug Administration.

A pharmaceutical composition or vaccine can contain a polynucleotide encoding one or more of the polypeptides as described above, such that the polypeptide is generated in situ. Such a polynucleotide can comprise DNA, RNA, a modified nucleic acid or a DNA/RNA hybrid. As noted above, a polynucleotide can be present within any of a variety of delivery systems known to those of ordinary skill in the art, including nucleic acid expression systems, bacteria and viral expression systems. Numerous gene delivery techniques are well known in the art, such as those described by Rolland, 1998, Crit. Rev. Therap. Drug Carrier Systems 15:143-198, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In a preferred embodiment, the DNA can be introduced using a viral expression system (e.g., vaccinia or other pox virus, retrovirus, or adenovirus), which can involve the use of a non-pathogenic (defective), replication competent virus. Suitable systems are disclosed, for example, in Fisher-Hoch et al., 1989, Proc. Natl. Acad. Sci. U.S.A. 86:317-321; Flexner et al., 1989, Ann. N.Y. Acad. Sci 569:86-103; Flexner et. al., Vaccine 8:17-21, 1990; U.S. Pat. Nos. 4,603,112, 4,769, 330, 4,777,127 and 5,017,487; WO 89/01973; GB 2,200,651; EP 0,345,242; WO 91/02805; Berkner, 1988, Biotechniques 6:616-627; Rosenfeld et al., 1991, Science 252:431-434; Kolls et al., 1994, Proc. Natl. Acad. Sci. U.S.A. 91:215-219; Kass-Eisler et al., 1993, Proc. Natl. Acad. Sci. U.S.A. 90:11498-11502; Guzman et al., 1993, Circulation 88:2838-2848; and Guzman et al., 1993, Cir. Res. 73:1202-1207. Techniques for incorporating DNA into such expression systems are well known to those of ordinary skill in the art. The DNA can also be "naked," as described, for example, in Ulmer et al., 1993, Science 259:1745-1749 and reviewed by Cohen, 1993, Science 259:1691-1692. The uptake of naked DNA can be increased by coating the DNA onto biodegradable beads, which are efficiently transported into the cells. It will be apparent that a vaccine can comprise both a polynucleotide and a polypeptide component. Such vaccines can provide for an enhanced immune response.

It will be apparent that a vaccine can contain pharmaceutically acceptable salts of the polynucleotides and polypeptides provided herein. Such salts can be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art can be employed in the pharmaceutical compositions of this invention, the type of carrier will vary depending on the mode of administration. Compositions of the present invention can be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, can be employed. Biodegradable microspheres (e.g., polylactate polyglycolate) can also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

Such compositions can also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention can be formulated as a lyophilizate. Compounds can also be encapsulated within liposomes using well known technology.

Any of a variety of non-specific immune response enhancers can be employed in the vaccines of this invention. For example, an adjuvant can be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7; or -12, can also be used as adjuvants.

Within the vaccines provided herein, the adjuvant composition is preferably designed to induce an immune response predominantly of the TH1 type. High levels of TH1-type cytokines (e.g., IFN-.gamma., TNF-α, IL-2 and IL-12) tend to favor the induction of cell mediated immune responses to an administered antigen. In contrast, high levels of TH2-type cytokines (e.g., IL-4, IL-5, IL-6 and IL-10) tend to favor the induction of humoral immune responses. Following application of a vaccine as provided herein, a patient will support an immune response that includes TH1- and TH2-type responses. Within a preferred embodiment, in which a response is predominantly TH1-type, the level of TH1-type cytokines will increase to a greater extent than the level of TH2-type cytokines. The levels of these cytokines can be readily assessed using standard assays. For a review of the families of cytokines, see Mosmann and Coffman, 1989, Ann. Rev. Immunol. 7:145-173.

Immunogenic agents of the invention, such as peptides, are sometimes administered in combination with an adjuvant. A variety of adjuvants can be used in combination with a peptide, such as a SPAS-1 human homolog or other cancer proteins of the invention, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIB ImmunoChem Research Inc., Hamilton, Mont.). Stimulon™ QS-21 is a triterpene glycoside or saponin isolated from the bark of the *Quillaja Saponaria* Molina tree found in South America (see Kensil et al, in VACCINE DESIGN: THE SUBUNIT AND ADJUVANT APPROACH (eds.), (Powell & Newman, Plenum Press, NY, 1995); U.S. Pat. No. 5,057,540; Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., 1997, N. Engl. J. Med. 336:86-91). Another adjuvant is CpG (WO 98/40100). Adjuvants can be administered as a component of a therapeutic composition with an active agent or can be administered separately, before, concurrently with, or after administration of the therapeutic agent.

Other preferred classes of adjuvants include aluminum salts (alum), such as aluminum hydroxide, aluminum phosphate, aluminum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton, Mont.) containing 2% squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™). Another class of preferred adjuvants is saponin adjuvants, such as Stimulon™ (QS-21, Aquila, Framingham, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, and alum, QS-21 and MPL together. Also, Incomplete Freund's adjuvant can be used (Chang et al., 1998, Advanced Drug Delivery Reviews 32:173-186), optionally in combination with any of alum, QS-21, and MPL and all combinations thereof.

Any vaccine provided herein can be prepared using well known methods that result in a combination of antigen, immune response enhancer and a suitable carrier or excipient. The compositions described herein can be administered as part of a sustained release formulation (i.e., a formulation such as a capsule or sponge that effects a slow release of compound following administration). Such formulations can generally be prepared using well known technology (see, e.g., Coombes et al., 1996, Vaccine 14:1429-1438) and administered by, for example, oral, rectal or subcutaneous implantation, or by implantation at the desired target site. Sustained-release formulations can contain a polypeptide, polynucleotide or antibody dispersed in a carrier matrix and/or contained within a reservoir surrounded by a rate controlling membrane.

Carriers for use within such formulations are biocompatible, and can also be biodegradable; preferably the formulation provides a relatively constant level of active component release. Such carriers include microparticles of poly(lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles can be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that can be engineered to be efficient APCs. Such cells can, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs can generally be isolated from any of a variety of biological fluids and organs, including tumor and peritumoral tissues, and can be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, 1998, Nature 392:245-251) and have been shown to be effective as a physiological adjuvant for eliciting prophylactic or therapeutic antitumor immunity (see Timmerman and Levy, 1999, Ann. Rev. Med. 50:507-529). In general, dendritic cells can be identified based on their typical shape (stellate in situ, with marked cytoplasmic processes (dendrites) visible in vitro), their ability to take up process and present antigens with high efficiency and their ability to activate naive T cell responses. Dendritic cells can, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) can be used within a vaccine (see Zitvogel et al., 1998, Nature Med. 4:594-600).

Dendritic cells and progenitors can be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells can be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow can be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fc.gamma. receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs can generally be transfected with a polynucleotide encoding a SPAS-1 protein or SPAS-1 human homolog (or portion or other variant thereof) such that the SPAS-1 polypeptide or SPAS-1 human homolog polypeptide, or an immunogenic portion thereof, is expressed on the cell surface. Such transfection can take place ex vivo, and a composition or vaccine comprising such transfected cells can then be used for therapeutic purposes, as described herein. Alternatively, a gene delivery vehicle that targets a dendritic or other antigen presenting cell can be administered to a patient, resulting in transfection that occurs in vivo. In vivo and ex vivo transfection of dendritic cells, for example, can generally be performed using any methods known in the art, such as those described in WO 97/24447, or the gene gun approach described by Mahvi et al., 1997, Immunology and Cell Biology 75:456-460. Antigen loading of dendritic cells can be achieved by incubating dendritic cells or progenitor cells with the prostate tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide can be covalently conjugated to an immunological partner that provides T cell help (e.g., a carrier molecule). Alternatively, a dendritic cell can be pulsed with a non-conjugated immunological partner, separately or in the presence of the polypeptide.

Vaccines and pharmaceutical compositions can be presented in unit-dose or multi-dose containers, such as sealed ampoules or vials. Such containers are preferably hermetically sealed to preserve sterility of the formulation until use. In general, formulations can be stored as suspensions, solutions or emulsions in oily or aqueous vehicles. Alternatively, a vaccine or pharmaceutical composition can be stored in a freeze-dried condition requiring only the addition of a sterile liquid carrier immediately prior to use.

The dosage can vary within this range depending upon the dosage form employed and the route of administration utilized. The exact formulation, route of administration and dosage can be chosen by the individual physician in view of the patient's condition. (See, e.g., Fingl et al., 1975, In: THE PHARMACOLOGICAL BASIS OF THERAPEUTICS, Ch. 1, p. 1).

Cancer Therapy

In further aspects of the present invention, the compositions described herein can be used for immunotherapy of cancer, such as prostate cancer. The SPAS-1 gene is expressed in in human and mouse cancers as shown in Table 1 and Table 2 below:

TABLE 1

Source of human ESTs that when BLASTed with SPAS-1 lead to a smallest Sum Probability P(N) < e–10

| Organ | Tissue type |
|---|---|
| Prostate | Fully malignant prostate cancer cells |
| Breast | Pectoral muscle after mastectomy |
| Cervix | Cervix tumor |
| Ovary | Ovary Tumor |
| Placenta | Choricarcinoma |
| Colon | Colon tumor metastasis |
| Colon | Colonic mucosa from patients with Crohn's disease |
| Brain | Neuroblastoma |
| Brain | Meningioma |
| Lung | Neuroendocrine lung carcinoid |
| Lung | Small cell carcinoma |
| Kidney | Renal cell tumor |
| B cell | Chronic Lymphatic Leukemia |
| Germinal Center | Germ cell tumors |

The coding region of SPAS-1 cDNA (nucleotides 1-465 from the partial cDNA sequence shown in FIG. 1) was BLASTed against a human EST Database. Hits leading to a smallest Sum Probability P(N) < e–10 were retrieved. Displayed in the table are the retrieved ESTs which originated from tumor tissues.

TABLE 2

Source of mouse ESTs that when BLASTed with SPAS-1 lead to a smallest Sum Probability P(N) < e–10

| Organ: | Tissue type: |
|---|---|
| Mammary | Infiltrating ductal carcinoma |
| Mammary gland | Mammary gland tumors |

The coding region of SPAS-1 cDNA (nucleotides 1-465 from the partial cDNA sequence shown in FIG. 1) was BLASTed against a mouse EST Database. Hits leading to a smallest Sum Probability P(N) < e–10 were retrieved. Displayed in the table are the retrieved ESTs which originated from tumor tissues.

Within such methods, pharmaceutical compositions and vaccines are typically administered to a patient. The term patient includes mammals, such as humans, domestic animals (e.g., dogs or cats), farm animals (cattle, horses, or pigs), monkeys, rabbits, rats, mice, and other laboratory animals. A patient can or can not be afflicted with cancer. Accordingly, the above pharmaceutical compositions and vaccines can be used to prevent the development of a cancer or to treat a patient afflicted with a cancer. A cancer can be diagnosed using criteria generally accepted in the art, including the presence of a malignant tumor. Pharmaceutical compositions and vaccines can be administered either prior to or following surgical removal of primary tumors and/or treatment such as administration of radiotherapy or conventional chemotherapeutic drugs. Administration can be by any suitable method, including administration by intravenous, intraperitoneal, intramuscular, subcutaneous, intranasal, intradermal, anal, vaginal, topical and oral routes.

Within certain embodiments and described above, immunotherapy can be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy can be passive immunotherapy as described above, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein can be cloned, expressed and transferred into other vectors or effector cells for adoptive immunotherapy. The polypeptides provided herein can also be used to generate antibodies or anti-idiotypic antibodies (as described above and in U.S. Pat. No. 4,918,164) for passive immunotherapy.

Effector cells can generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein can be used to rapidly expand antigen-specific T cell cultures in order to generate a sufficient number of cells for immunotherapy. In particular, antigen-presenting cells, such as dendritic, macrophage or B cells, can be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., 1997, Immunological Reviews 157:177).

Alternatively, a vector expressing a polypeptide recited herein can be introduced into antigen presenting cells taken from a patient and clonally propagated ex vivo for transplant back into the same patient. Transfected cells can be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and can be readily established using standard techniques. In general, the pharmaceutical compositions and vaccines can be administered by injection (e.g., intracutaneous, intramuscular, intravenous or subcutaneous), intranasally (e.g., by aspiration) or orally. Preferably, between 1 and 10 doses can be administered over a 52 week period. Preferably, 6 doses are administered, at intervals of 1 month, and booster vaccinations can be given periodically thereafter. Alternate protocols can be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 1 μg to 5 mg, preferably 100 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a SPAS-1 protein or SPAS-1 human homolog generally correlate with an improved clinical outcome. Such immune responses can generally be evaluated using standard proliferation, cytotoxicity or cytokine assays, which can be performed using samples obtained from a patient before and after treatment.

Cancer Diagnosis

In general, a cancer can be detected in a patient based on the presence of one or more SPAS-1 proteins and/or polynucleotides (and SPAS-1 human homolog proteins and/or polynucleotides) encoding such proteins in a biological sample (such as blood, sera, urine and/or tumor biopsies) obtained from the patient. In other words, such proteins can be used as markers to indicate the presence or absence of a cancer such as prostate cancer. In addition, such proteins can be useful for the detection of other cancers. The binding agents provided herein generally permit detection of the level of antigen that binds to the agent in the biological sample. Polynucleotide primers and probes can be used to detect the level of mRNA encoding a tumor protein, which is also indicative of the presence or absence of a cancer. In general, a prostate tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, 1988, ANTIBODIES: A LABORATORY MANUAL, Cold Spring Harbor Laboratory Press. In general, the presence or absence of a cancer in a patient can be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample.

The bound polypeptide can then be detected using a detection reagent that contains a reporter group and specifically binds to the binding agent/polypeptide complex. Such detection reagents can comprise, for example, a binding agent that specifically binds to the polypeptide or an antibody or other agent that specifically binds to the binding agent, such as an anti-immunoglobulin, protein G, protein A or a lectin. Alternatively, a competitive assay can be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length SPAS-1 proteins and portions thereof to which the binding agent binds, as described above.

The solid support can be any material known to those of ordinary skill in the art to which the tumor protein can be attached. For example, the solid support can be a test well in a microtiter plate or a nitrocellulose or other suitable membrane. Alternatively, the support can be a bead or disc, such as glass, fiberglass, latex or a plastic material such as polystyrene or polyvinylchloride. The support can also be a magnetic particle or a fiber optic sensor, such as those disclosed, for example, in U.S. Pat. No. 5,359,681. The binding agent can be immobilized on the solid support using a variety of techniques known to those of skill in the art, which are amply described in the patent and scientific literature. In the context of the present invention, the term "immobilization" refers to both noncovalent association, such as adsorption, and covalent attachment (which can be a direct linkage between the agent and functional groups on the support or can be a linkage by way of a cross-linking agent). Immobilization by adsorption to a well in a microtiter plate or to a membrane is preferred. In such cases, adsorption can be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support can generally be achieved by first reacting the support with a bifunctional reagent that will react with both the support and a functional group, such as a hydroxyl or amino group, on the binding agent. For example, the binding agent can be covalently attached to supports having an appropriate polymer coating using benzoquinone or by condensation of an aldehyde group on the support with an amine and an active hydrogen on the binding partner (see, e.g., PIERCE IMMUNOTECHNOLOGY CATALOG AND HANDBOOK, 1991, at A12-A13).

In certain embodiments, the assay is a two-antibody sandwich assay. This assay can be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample can be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium can be readily determined by assaying the level of binding that occurs over a period of time. At room temperature, an incubation time of about 30 minutes is generally sufficient.

Unbound sample can then be removed by washing the solid support with an appropriate buffer, such as PBS containing 0.1% Tween 20™. The second antibody, which contains a reporter group, can then be added to the solid support. Preferred reporter groups include those groups recited above.

The detection reagent is then incubated with the immobilized antibody-polypeptide complex for an amount of time sufficient to detect the bound polypeptide. An appropriate amount of time can generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods can be used to detect dyes, luminescent groups and fluorescent groups. Biotin can be detected using avidin, coupled to a different reporter group (commonly a radioactive or fluorescent group or an enzyme). Enzyme reporter groups can generally be detected by the addition of substrate (generally for a specific period of time), followed by spectroscopic or other analysis of the reaction products.

To determine the presence or absence of a cancer, such as prostate cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., CLINICAL EPIDEMIOLOGY: A BASIC SCIENCE FOR CLINICAL MEDICINE, Little Brown and Co., 1985, p. 106-7. Briefly, in this embodiment, the cut-off value can be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method can be considered positive. Alternatively, the cut-off value can be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent can then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols can be readily modified to use prostate tumor polypeptides to detect antibodies that bind to such polypeptides in a biological sample. The detection of such SPAS-1 protein specific antibodies can correlate with the presence of a cancer.

A cancer can also, or alternatively, be detected based on the presence of T cells that specifically react with a SPAS-1 protein or SPAS-1 human homolog in a biological sample. Within certain methods, a biological sample comprising $CD4^+$ and/or $CD8^+$ T cells isolated from a patient is incubated with a prostate tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells can be isolated from a patient by routine techniques (such as by Ficoll/Hypaque density gradient centrifugation of peripheral blood lymphocytes). T cells can be incubated in vitro for 2-9 days (typically 4 days) at 37° C. with Mtb-81 or Mtb-67.2 polypeptide (e.g., 5-25 µg/ml). It can be desirable to incubate another aliquot of a T cell sample in the absence of prostate tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer can also, or alternatively, be detected based on the level of mRNA encoding a SPAS-1 protein or SPAS-1 human homolog in a biological sample. For example, at least two oligonucleotide primers can be employed in a polymerase chain reaction (PCR) based assay to amplify a portion of a prostate tumor cDNA derived from a biological sample, wherein at least one of the oligonucleotide primers is specific for (i.e., hybridizes to) a polynucleotide encoding the SPAS-1 protein or SPAS-1 human homolog. The amplified cDNA is then separated and detected using techniques well known in the art, such as gel electrophoresis. Similarly, oligonucleotide probes that specifically hybridize to a polynucleotide encoding a SPAS-1 protein or SPAS-1 human homolog can be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a SPAS-1 protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which can be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence recited in FIG. 1. Techniques for both PCR based assays and hybridization assays are well known in the art (see, for example, Mullis et al., Cold Spring Harbor Symp. Quant. Biol., 51:263, 1987; Erlich ed., PCR TECHNOLOGY, Stockton Press, NY, 1989).

One preferred assay employs RT-PCR, in which PCR is applied in conjunction with reverse transcription. Typically, RNA is extracted from a biological sample such as a biopsy tissue and is reverse transcribed to produce cDNA molecules. PCR amplification using at least one specific primer generates a cDNA molecule, which can be separated and visualized using, for example, gel electrophoresis. Amplification can be performed on biological samples taken from a test patient and from an individual who is not afflicted with a cancer. The amplification reaction can be performed on several dilutions of cDNA spanning two orders of magnitude. A two-fold or greater increase in expression in several dilutions of the test patient sample as compared to the same dilutions of the non-cancerous sample is typically considered positive.

In another embodiment, SPAS-1 proteins and polynucleotides and SPAS-1 human homolog proteins and polynucleotides encoding such proteins can be used as markers for monitoring the progression of cancer. In this embodiment, assays as described above for the diagnosis of a cancer can be performed over time, and the change in the level of reactive polypeptide(s) evaluated. For example, the assays can be performed every 24-72 hours for a period of 6 months to 1 year, and thereafter performed as needed. In general, a cancer is progressing in those patients in whom the level of polypeptide detected by the binding agent increases over time. In contrast, the cancer is not progressing when the level of reactive polypeptide either remains constant or decreases with time.

Certain in vivo diagnostic assays can be performed directly on a tumor. One such assay involves contacting tumor cells with a binding agent. The bound binding agent can then be detected directly or indirectly via a reporter group. Such binding agents can also be used in histological applications. Alternatively, polynucleotide probes can be used within such applications.

As noted above, to improve sensitivity, multiple SPAS-1 protein markers and SPAS-1 human homolog markers can be assayed within a given sample. It will be apparent that binding agents specific for different proteins provided herein can be combined within a single assay. Further, multiple primers or probes can be used concurrently. The selection of tumor protein markers can be based on routine experiments to determine combinations that results in optimal sensitivity. In addition, or alternatively, assays for tumor proteins provided herein can be combined with assays for other known tumor antigens.

Methods of Identifying and Cloning T Cell-Defined Tumor Antigens

The methods disclosed herein to clone the SPAS-1 gene can be used as a general method for identifying other T cell tumor targets. This strategy exploits the ability of CTLA-4 blockade to greatly enhance T cell responses to tumor antigens in order to facilitate the production of T cell lines which would not normally be possible due to low frequency or to peripheral T cell tolerance. This strategy consists of six main components: 1. As was the case with the TRAMP murine model before, human prostatic adenocarcinoma, an appropriate mouse model of the relevant human cancer is chosen. 2. Mice are immunized with the tumor cells as a vaccine or with tumor cells genetically engineered to express cytokines, costimulatory molecules, and alike together with blockade of CTLA-4 using appropriate blocking antibodies. 3. Both $CD8^+$ and $CD4^+$ T cell lines are established from the immunized mice using conventional in vitro methods of restimulation and culture. 4. These T cell lines are fused with an appropriate T cell hybridoma fusion partner expressing a reporter gene for T cell activation and T cell hybridoma are selected for specificity of the original T cells (see Karttunen, J., 1992, Proc. Natl. Acad. Sci. U.S.A. 89:6020-6024). 5. The hybridomas described in (4) above are then used to screen CHO cells or other readily transfectable cells engineered to express a cDNA library from the tumor cells used for the original immunization along with the DNA encoding the restricting element used by the original T cells (see Karttunen, J., 1992, Proc. Natl. Acad. Sci. U.S.A. 89:6020-6024). 6. cDNAs obtained in (5) can be sequenced and full length and partial length clones can be obtained; full length genes can be obtained by conventional molecular methods. The human homologs can be obtained either by conventional molecular methods such as low stringency hybridization or by scanning available genomic or proteomic databases. Exemplary genes such as SPAS-1 can be isolated and characterized (see Examples). 7. With either the human or the mouse gene cDNA, a minimal T cell epitope can then be defined by transfection of appropriate cells with truncated variants of the cDNA and epitopes confirmed by analysis of synthetic peptides as described (see Examples).

Methods of Diagnosis

The invention provides methods of detecting an immune response against prostate tumor peptide, for example in a patient suffering from or susceptible to cancer (i.e. prostate cancer). The methods may be used for monitoring a course of treatment being administered to a patient, in prognostic methods, etc. The methods can be used to monitor both therapeutic treatment on symptomatic patients and prophylactic treatment on asymptomatic patients. The methods are useful for monitoring naturally occurring immune responsiveness against SPAS-1; active immunization of SPAS-1 (e.g., an immune response produced in response to administration of immunogen) and passive immunization (e.g., measuring level of administered immunologic agent).

Various methods known in the art may be used to determine the presence of an immune response. The tissue sample for analysis is typically blood, plasma, serum, mucous or cerebrospinal fluid from the patient. The sample is analyzed for indication of an immune response to any form of a SPAS-1 peptide of the invention. The immune response can be determined from the presence of, e.g., antibodies or T-cells that specifically bind to the prostate tumor peptide.

Where T cell responses are of interest, the sample is a sample comprising lymphocytes, e.g. the cellular portion of a blood sample, etc. T cells may be stained with a peptide/MHC complex, for example using detectably labeled MHC reagents (i•TAg™ MHC Tetramers, Beckman Coulter; BD™ DimerX reagents; ProImmune Pro5® MHC class I Pentamers etc.) to determine the presence of T cells having specificity for a SPAS-1 peptide. Alternatively, T cells may be assayed in vitro for reactivity to a SPAS-1 peptide, using methods known in the art. For example, a sample comprising T cells may be contacted with a SPAS-1 antigen presented by an antigen presenting cell; or provided as a stable MHC complex; and the response of the cells quantitated, for example by proliferation, cytokine synthesis, cytotoxicity and the like. Measured values may thus include quantitation of antigen specific T cells, quantitation of T cell proliferation in response to the antigen, quantitation of cytokine release, e.g. IFN-γ, IL-2, etc. in response to presented antigen, percentage of specific cell lysis and the like.

Some methods may entail determining a baseline value of an immune response in a normal control, or in a patient before administering a dosage of agent, and comparing this with a value for the test immune response, i.e. after treatment, in a patient sample, etc. A significant increase (i.e., greater than the typical margin of experimental error in repeat measurements of the same sample, expressed as one standard deviation from the mean of such measurements) in value of the immune response signals the presence of an immune response against SPAS-1 in the sample. If the value for immune response does not change significantly, or decreases, signals the lack of an immune response against SPAS-1 in the sample. In other methods, a control value (i.e., a mean and standard deviation) of immune response is determined for a control population. Typically the individuals in the control population are free of the cancer of interest. Measured values of immune response in a patient may be compared with the control value.

In general, patients undergoing an initial course of treatment with an immunogenic agent are expected to show an increase in immune response with successive dosages, which eventually reaches a plateau. Patients have a naturally occurring immune response against SPAS-1 will also show a positive response. Administration of agent is generally continued while the immune response is increasing. Attainment of the plateau is an indicator that the administered of treatment can be discontinued or reduced in dosage or frequency.

In other methods, a control value of immune response (e.g., a mean and standard deviation) is determined from a control population of individuals who have undergone treatment with a therapeutic agent. Measured values of immune response in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment regime, for example, use of a different adjuvant can be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

In general, the procedures for monitoring passive immunization are similar to those for monitoring active immunization described above. However, the antibody profile following passive immunization typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to the prostate tumor peptide in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

Diagnostic Kits

The present invention further provides kits for use within any of the above diagnostic methods. Such kits typically comprise two or more components necessary for performing a diagnostic assay for the detection of immune responses specific to SPAS-1, or to the expression of SPAS-1. Components can be compounds, reagents, containers and/or equipment. Kits also typically contain labeling providing directions for use of the kit. For example, one container within a kit can contain a monoclonal antibody or fragment thereof or soluble T cell receptor that specifically binds to a SPAS-1 protein, to a SPAS-1 genetic sequence; or to a SPAS-1/MHC complex. Alternatively, an MHC/SPAS-1 peptide complex may be included. Such reagents can be provided attached to a support material, as described above. One or more additional containers can enclose elements, such as reagents or buffers, to be used in the assay. Such kits can also, or alternatively, contain a detection reagent as described above that contains a reporter group suitable for direct or indirect detection of antibody binding. The term labeling refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Alternatively, a kit can be designed to detect the level of mRNA encoding a SPAS-1 protein in a biological sample. Such kits generally comprise at least one oligonucleotide probe or primer, as described above, that hybridizes to a polynucleotide encoding a SPAS-1 protein. Such an oligonucleotide can be used, for example, within a PCR or hybridization assay. Additional components that can be present within such kits include a second oligonucleotide, a diagnostic reagent or container to facilitate the detection of a polynucleotide encoding a SPAS-1 protein.

The following Examples are offered by way of illustration and not by way of limitation.

EXAMPLE 1

Generation of Anti-TRAMP T Cell Lines

Normal C57/BL6 male mice were immunized with GMCSF-producing TRAMP-C2 cells and CTLA-4 according to standard protocols (see, for example, Kwon. et al., Proc. Nat. Acad. Sci., U.S.A., 1997, 94: 8099-8103; Kwon et al., 1999, Proc. Natl. Acad. Sci. U.S.A., 1999, 96: 15074-15079; and Hurwitz et al., 2000, Cancer Research 6: 2444-2448. Briefly, as shown in FIG. 2, three C57/BL6 male mice were immunized subcutaneously with $2\times10^6$ irradiated GMCSF-producing TRAMP-C2 cells on day 1. On days 3, 6 and 9, 100 µg anti-CTLA-4 antibody (9H10) were injected intraperitonally in the same mice. On day 12, 26 and 54, the mice were re-immunized with $2\times10^6$ irradiated GMCSF-producing TRAMP-C2 cells. 8 days later, the spleen and lymph nodes were harvested, pooled, and put in single cell suspension in 6 well plates at $20\times10^6$ cells/well with $10^6$ MitomycinC-treated B7-expressing TRAMP-C2 cells as antigen-presenting cells and 5% final concentration of ConA supernatant. The T cell line was restimulated every 7 days by adding to each well $10^6$ MitomycinC-treated B7-expressing TRAMP-C2 cells in 5% ConA supernatant.

EXAMPLE 2

The T Cell Line is Specific for TRAMP Tumor

Normal C57/BL6 male mice were immunized with GMCSF-producing TRAMP-C2 cells and CTLA-4 according to standard procedures described. T cells lines were generated by stimulating spleen and lymph node cells from immunized mice with B7-expressing TRAMP cells in vitro. These cells were propagated in vitro by standard techniques.

Figure 3:
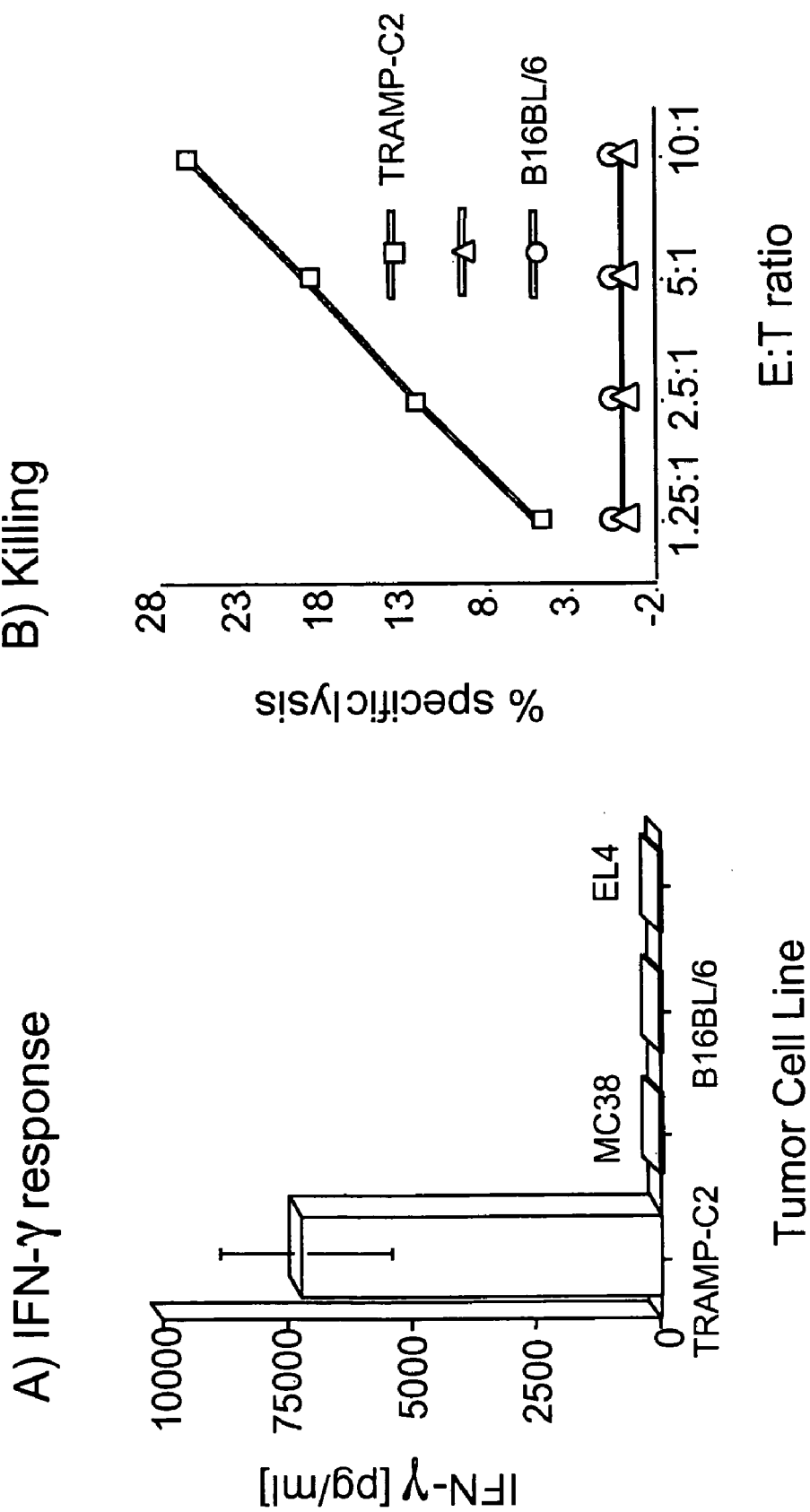
FIG. 3. The anti-TRAMP T cell line is specific for TRAMP tumor. The function and specificity of the T cells were assessed using standard assays for interferon gamma. (IFN) production (A) and cytotoxicity (B) in response to incubation with a panel of syngeneic, C57BL/6 derived tumors of different cellular origins.

FACS analysis of the cell line showed the cells were uniformly $CD8^+$, indicating that the cells were likely to be cytotoxic T lymphocytes and the target antigen a peptide restricted by Class I MHC molecules. The function and specificity of the T cells were assessed using standard assays for interferon gamma. (IFN) production (A) and cytotoxicity (B) in response to incubation with a panel of syngeneic, C57BL/6 derived tumors of different cellular origins. As shown in FIG. 3 in both assays the T cell line recognized only the TRAMP-C2 tumor line, and did not react with other tumors, including a melanoma (B16), a colon carcinoma (MC38), or a lymphoma (EL-4). This demonstrates that the T cell line is specific for the TRAMP prostatic tumor cells.

EXAMPLE 3

The CD8$^+$ T Cell Line Recognizes Naturally Processed Tumor Peptides (NPTPs) from TRAMP Prostate Tumor but not Thymoma Cells To determine the nature of the antigen detected by the T cell line, and to further examine specificity, peptides were eluted from TRAMP-C2 cells or from EL-4 thymoma cells by standard conditions. These peptides were then pulsed onto RMA-S cells, a cell line that does not express a critical peptide transporter and thus has on its surface empty MHC molecules that efficiently take up exogenously added peptide. Naturally Processed Tumor Peptides (NPTPs) were isolated by treating 10.sup.8 TRAMP-C2 and as a control $10^8$ EL-4 tumor cells with 4% TFA, pelleting the cell debris and passing the supernatant through a 10 kD-cutoff filter.

Figure 4:
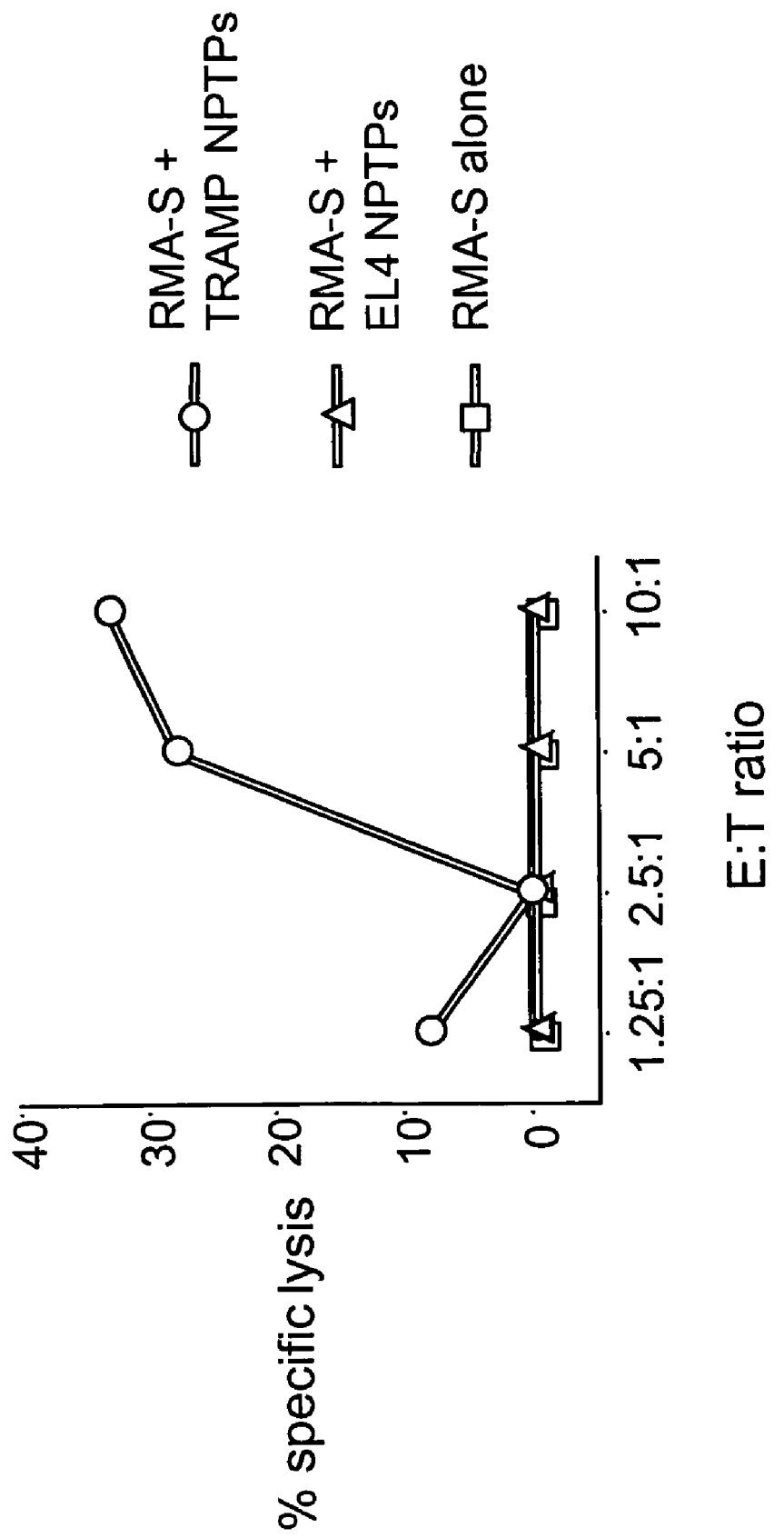
FIG. 4. The CD8+ T cell Line Recognizes Naturally Processed Tumor Peptides (NPTPs) from TRAMP prostate tumor but not thymoma cells.

As shown in FIG. 4, naturally processed peptides (NPTPs) from TRAMP-C2, but not EL-4 cells, sensitized RMA-S cells to lysis. This indicates the specificity of the T cell line for TRAMP-C2 peptides.

EXAMPLE 4

The CD8$^+$ T Cell Line Recognizes Three Different TRAMP-Derived Cell Lines

Figure 5:
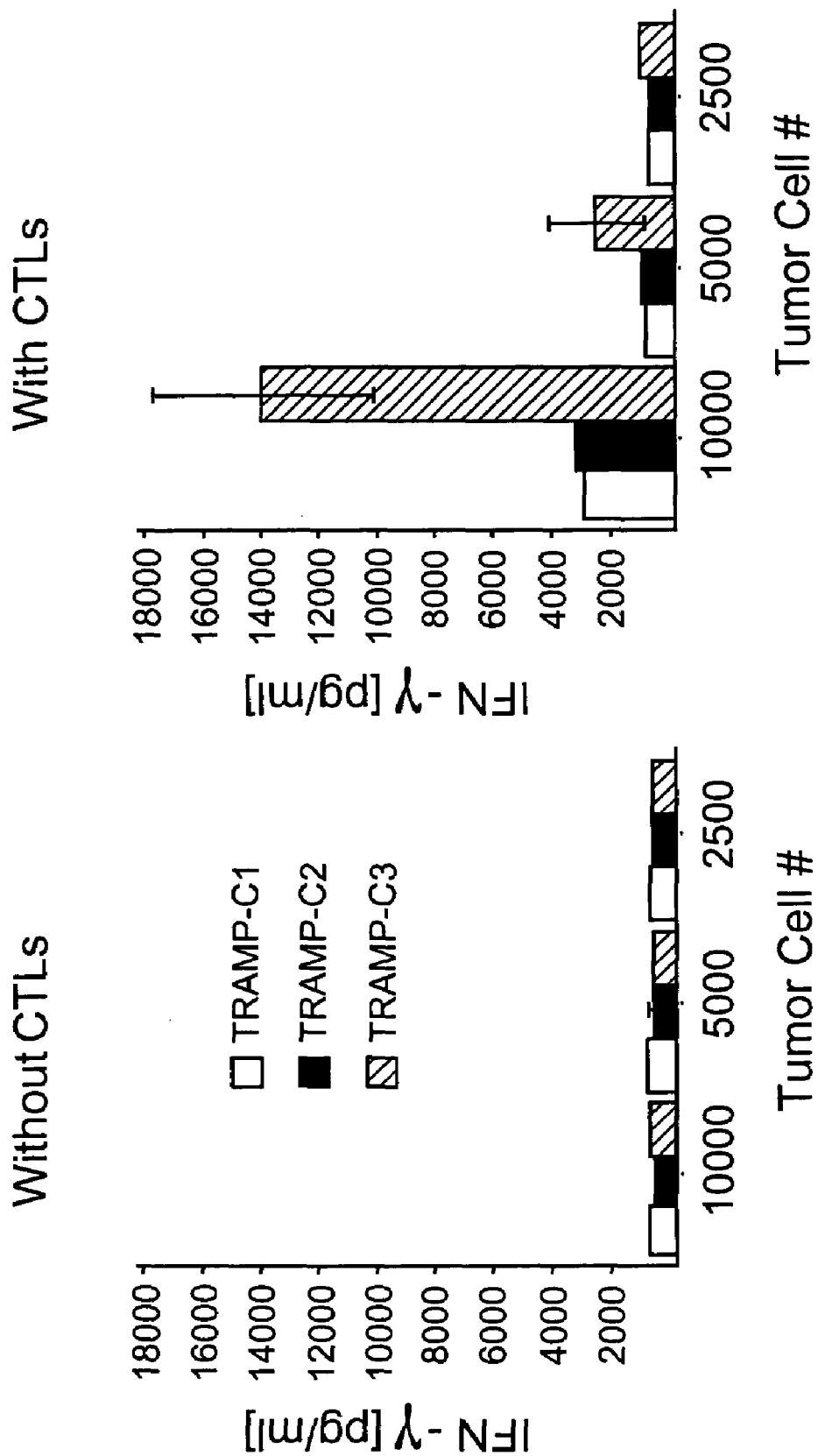
FIG. 5. The CD8+ T cell line recognizes three different TRAMP-derived cell lines.

To determine whether reactivity of the T cell line was restricted to TRAMP-C2, the tumor cell line used for immunization, the response of the T cells to two additional prostatic tumor lines derived from TRAMP mice was examined. As shown in FIG. 5, the T cell line responded to all three cell lines. This suggests that the T cells are not specific for an antigen restricted to a single tumor cell line, but is directed to an antigen generally expressed by prostatic tumor cells.

EXAMPLE 5

Adoptive Transfer of TRAMP-C2-Specific CTLs into Mice Delays Ectopic Tumor Growth On day 0, C57BL6 mice were injected subcutaneously with 4×10$^6$ TRAMP-C2 CD8$^+$ T cells. On day 0 and 14 the mice received 2×10$^6$ TRAMP-specific T cells in PBS or PBS alone intravenously. In order to provide a source of T cell help to the TRAMP-specific CD8$^+$ T cells the mice were injected daily from day 0 to day 14 with 10000 U of recombinant human IL-2 in PBS subcutaneously.

Figure 6:
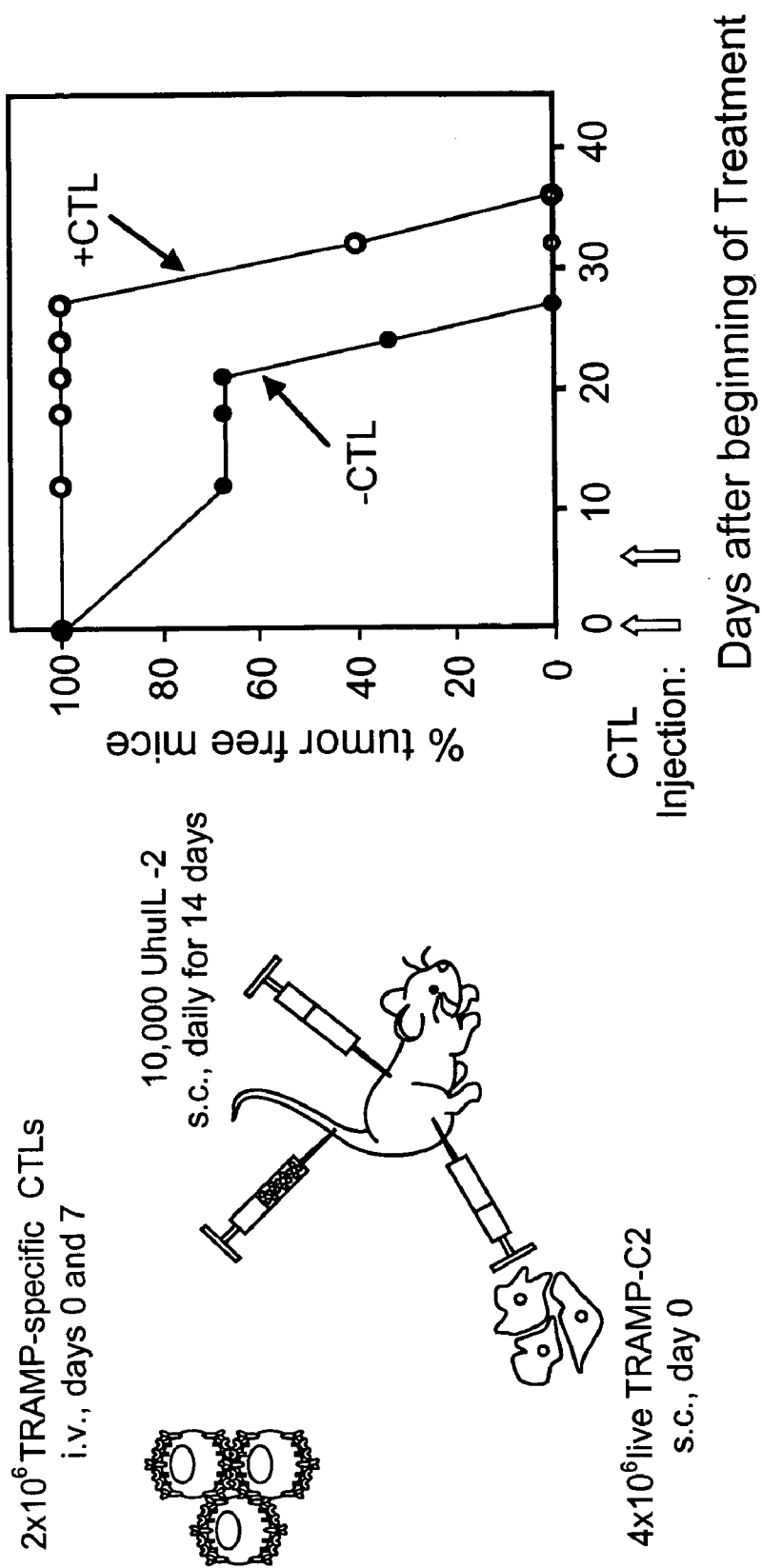
FIG. 6. Adoptive transfer of TRAMP-C2-specific CTLs into mice delays ectopic tumor growth.

The results in FIG. 6 show that during the two weeks where both the TRAMP-specific T cells and IL-2 were present, 100% of the mice remained tumor free versus 60% when only IL-2 was present. This demonstrates the in vivo anti-tumor effect of the TRAMP-specific T cells.

EXAMPLE 6

Scheme for Production of T Cell Hybridomas from the CD8$^+$ T Cell Line

Figure 7:
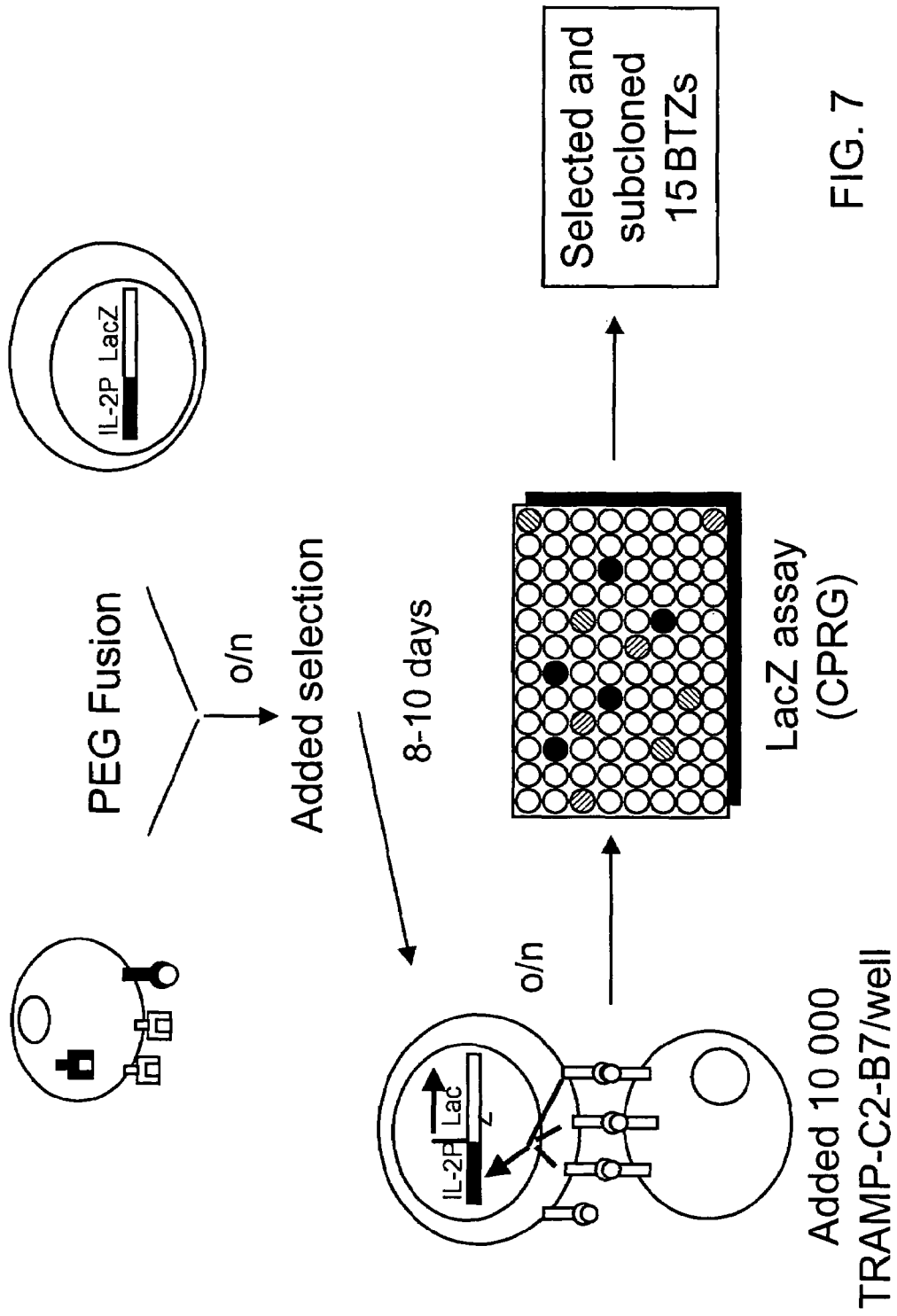
FIG. 7. Schematic for production of T cell hybridomas from the CD8+ T cell line.

To facilitate expression cloning of antigens responsible for stimulating the CD.sup.8+ T cells lines, cells were fused with the LacZ-inducible Fusion Partner BWZ.36 (see FIG. 7). This Fusion Partner was stably transfected with a DNA construct containing the LacZ coding sequence under the direct transcriptional control of three tandemly arranged IL-2 enhancer elements (NFAT). In the resultant hybridomas, engagement of the clonally expressed T cell antigen receptors by specific Ag/MHC complexes results in induction of expression of the LacZ enzyme, allowing rapid detection of T cell responses by calorimetric measurement of substrate conversion.

EXAMPLE 7

The BTZ Hybridomas Retain Specificity for TRAMP Tumors

Figure 8:
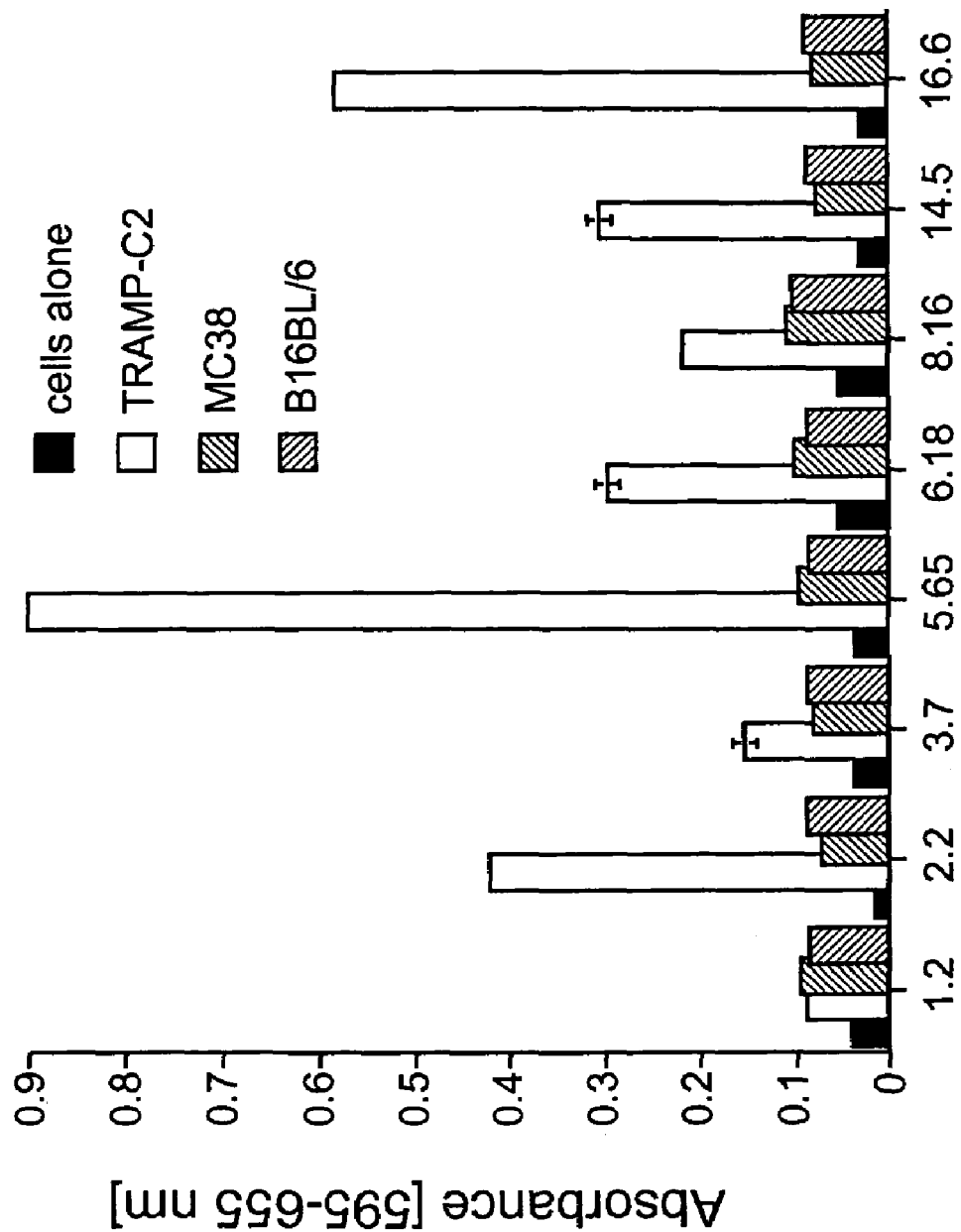
FIG. 8. The BTZ Hybridomas retain specificity for TRAMP tumors.

Eight T cells hybridoma clones produced as described above were tested for retention of reactivity by measuring induction of LacZ activity upon incubation with tumor cells. As shown in FIG. 8, seven of eight clones reacted with TRAMP-C2 cells, and not with MC38 or B16 cells. This confirms that the hybridomas retain the specificity of the original T cell line.

EXAMPLE 8

Determination of MHC-Restriction of the T Cell Hybridomas

Figure 9:
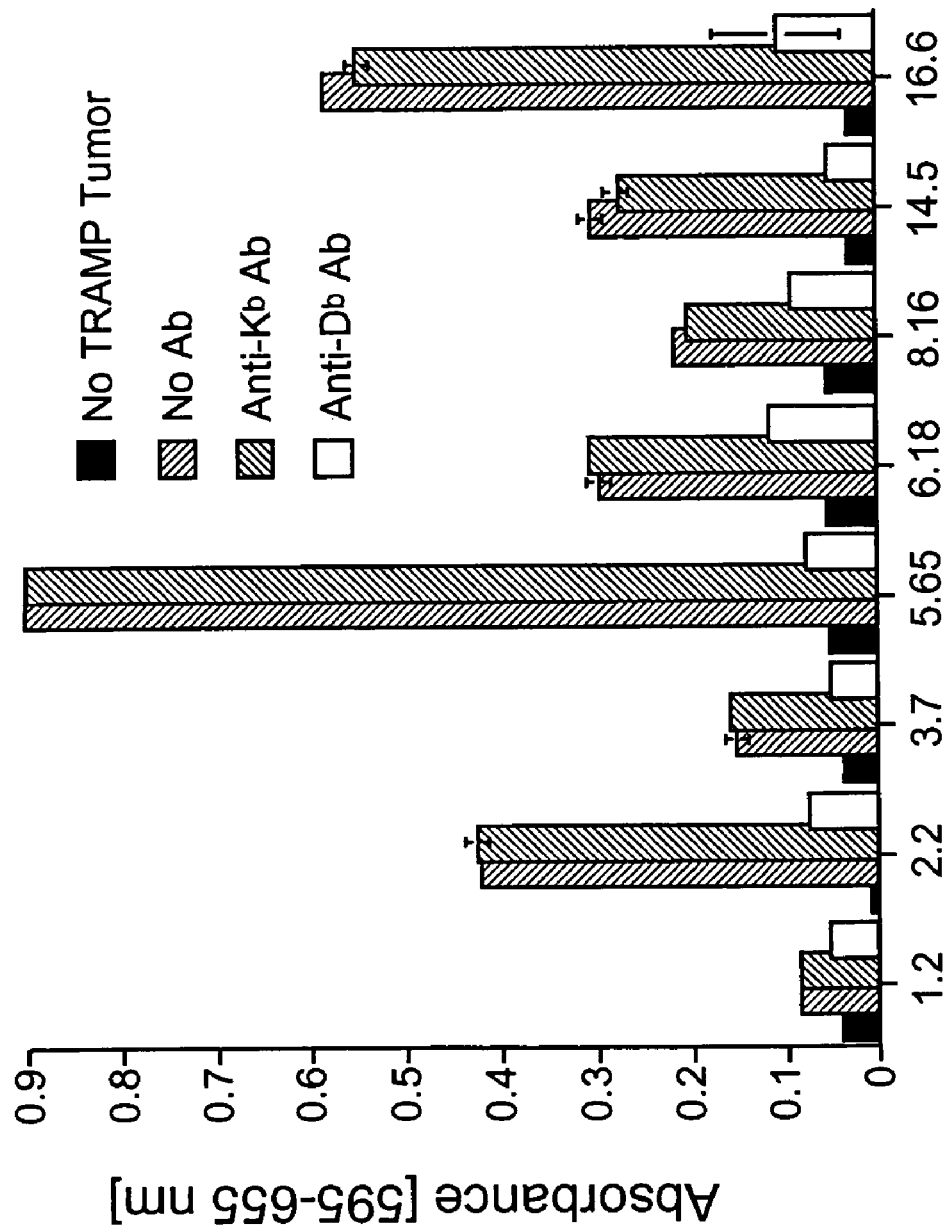
FIG. 9. Determination of MHC-Restriction of the T cell hybridomas.

In order to determine the MHC restriction of antigen recognition, T hybridoma cells were incubated with TRAMP-C2 cells in the presence of antibodies specific for H-2K$^b$ or H-2D$^b$ molecules. Briefly, 2×10$^4$ TRAMP-C2 cells were incubated for 1 hour with anti-K$^b$ (Y3, ATCC, HB176) or anti-D$^b$ antibody (B22.249.RI, Cedar Lane, Calif.) before addition of BTZs (1×10$^6$/well). Plates were incubated overnight and the T cell response measured as the LacZ activity by the conversion of the substrate chlorophenol red b-pyranoside (CPRG) at 595 nm and 655 nm as reference. As shown in FIG. 9, only anti-D$^b$, and not anti-K$^b$, resulted in inhibition. This indicated that all the hybridomas tested were restricted to an antigen expressed in the context of D$^b$ MHC molecules.

EXAMPLE 9

HPLC Analysis Indicates that the Hybridomas were Reactive with a Single Peptide Peak To determine the complexity of antigens responsible for stimulation of the anti-TRAMP T cell hybridomas, total cell surface peptides were eluted from TRAMP-C2 cells and fractionated by reverse phase high performance liquid chromatography. Briefly, in order to extract the whole acid soluble peptide pool from TRAMP-C2 cells, 1×10.sup.8 TRAMP-C2 cells were induced overnight with IFN-.gamma. (50 U/ml), then washed with PBS and extracted with 1 ml of 10% Formic acid in water. Cellular debris were removed by centrifugation and fractionated by HPLC after filtration through a 10 kD filter. Reverse Phase C18 narrow bore column was run in 0.1% TFA in water (solvent A) and 0.1% TFA acetonitrile (solvent B). Flow rate was maintained at 0.25 ml/min and fractions were collected in 96 well flat bottom plates, dried in a vacuum centrifuge and resuspended in 30 μl PBS+12% DMSO. Individual fractions were used to pulse Db-expressing L-cells, and the pulsed antigen presenting cells incubated with T cell hybrids BTZ5.65 or BTZ6.18 ($8.5 \times 10^4$/well) and $D^b$-expressing L-cells as APCs ($3 \times 10^4$/well). Mock injections with sample buffer alone were performed before each extract sample using the same column and identical run conditions to demonstrate the absence of cross-contamination between samples. The collected fractions of both cell extracts and mocks were assayed in the same experiment, using the same APC and T cell Hybrids.

Figure 10:
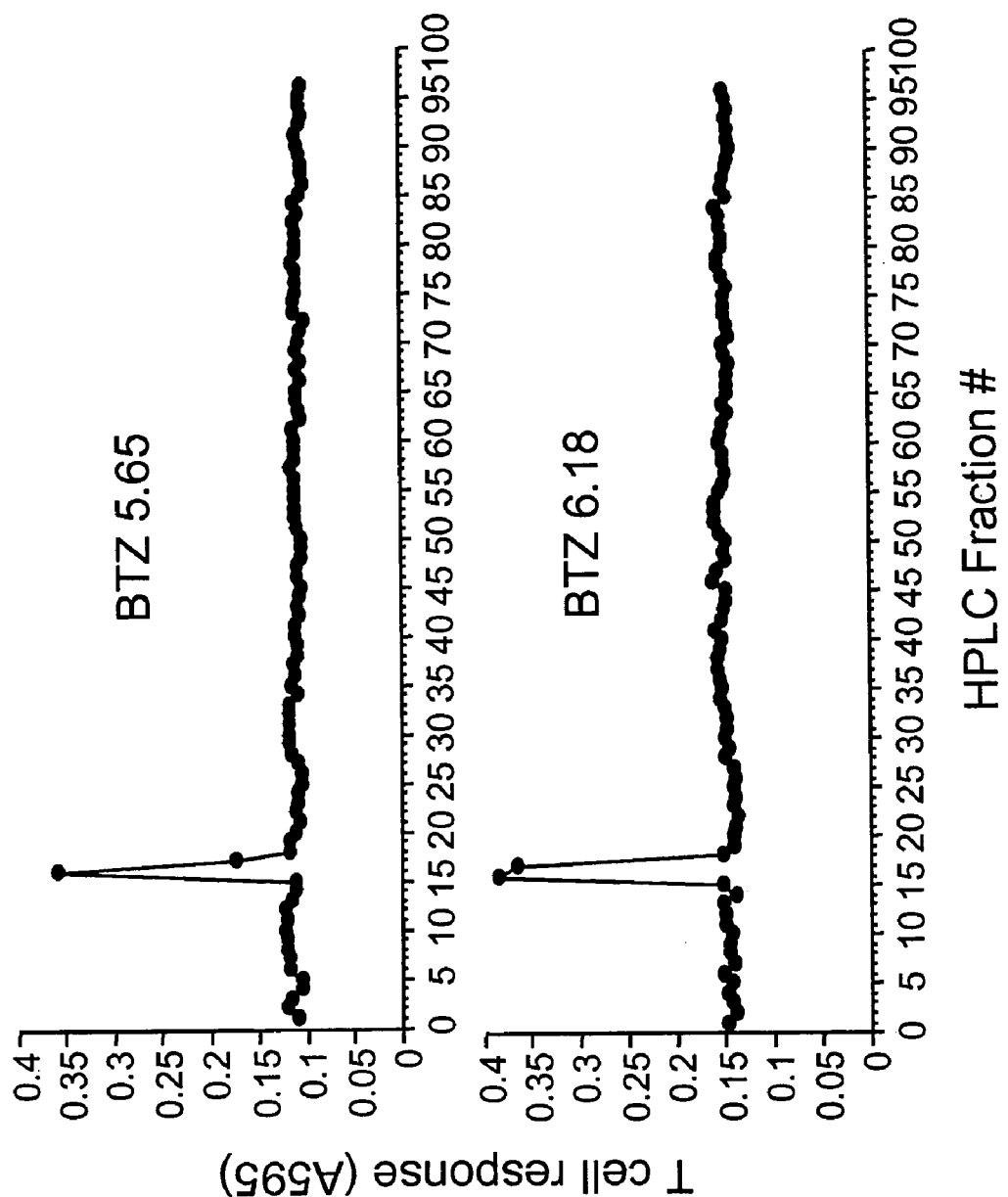
FIG. 10. HPLC analysis indicates that the hybridomas were reactive with a single peptide peak.

As shown in FIG. 10, both hybridomas reacted with a single, and the same, peak. This strongly suggested that the T cell specificity was for a single antigenic peptide.

EXAMPLE 10

Scheme for Expression Cloning of the TRAMP Antigen

Figure 11:
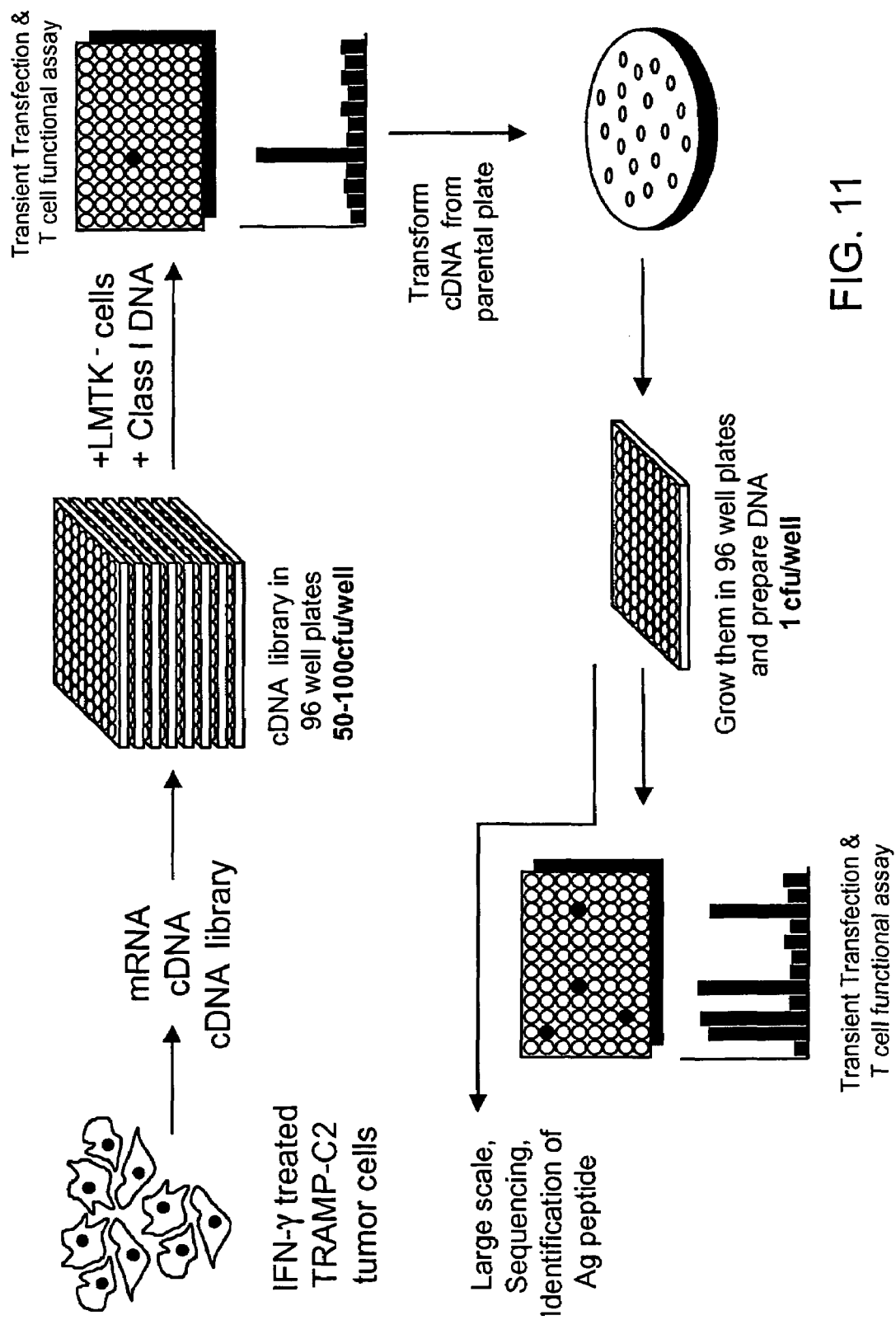
FIG. 11. Scheme for expression cloning of the TRAMP antigen.

A cDNA library was prepared from TRAMP-C2 cells. Briefly, as shown in FIG. 11, poly $A^+$ mRNA was derived from IFN-.gamma.-treated TRAMP-C2 tumor cells using standard protocols and a unidirectional cDNA Library was constructed in the BstXI/NotI sites of the mammalian expression vector pcDNA1 (Invitrogen, San Diego, Calif.). The cDNAs were screened by transforming competent bacteria with recombinant plasmids and culturing them in pools of 30-100 cfu in 96 well U-bottom plates. Miniscale preparation of the bacterial plasmid DNA was performed directly in the 96 well plates and subsequently transfected into $3 \times 10^4$ LMtk-cells co-transfected with the relevant $D^b$ MHC class I cDNA and B7-2 cDNA. Two days later, $8.5 \times 10^4$ BTZ5.65 were added per well and their response measured by standard techniques. This allowed the initial identification of positive pools. Repeating the screen with individual colonies obtained from the positive cDNA pool allowed final confirmation and isolation of the cDNA.

Figure 12:
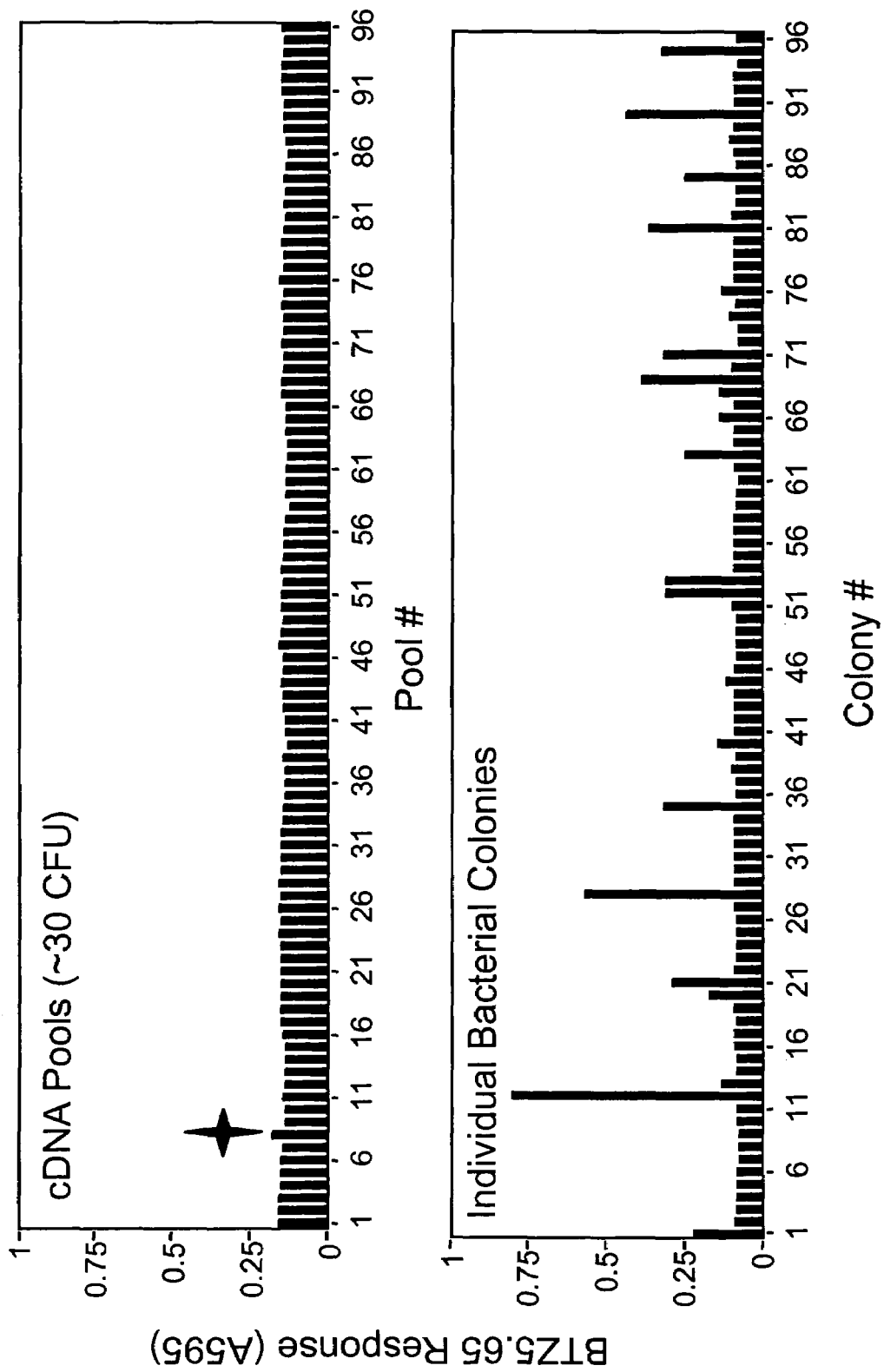
FIG. 12. Isolation of the cDNA clone that encodes for the TRAMP-C2 antigenic peptide.

DNA from stimulating pools was recycled through the process until a single clone was obtained as described above. This clone was designated SPAS-1 (see FIG. 12; see also FIG. 1 for the partial and full length SPAS-1 nucleotide and predicted amino acid sequences).

EXAMPLE 11

Figure 13:
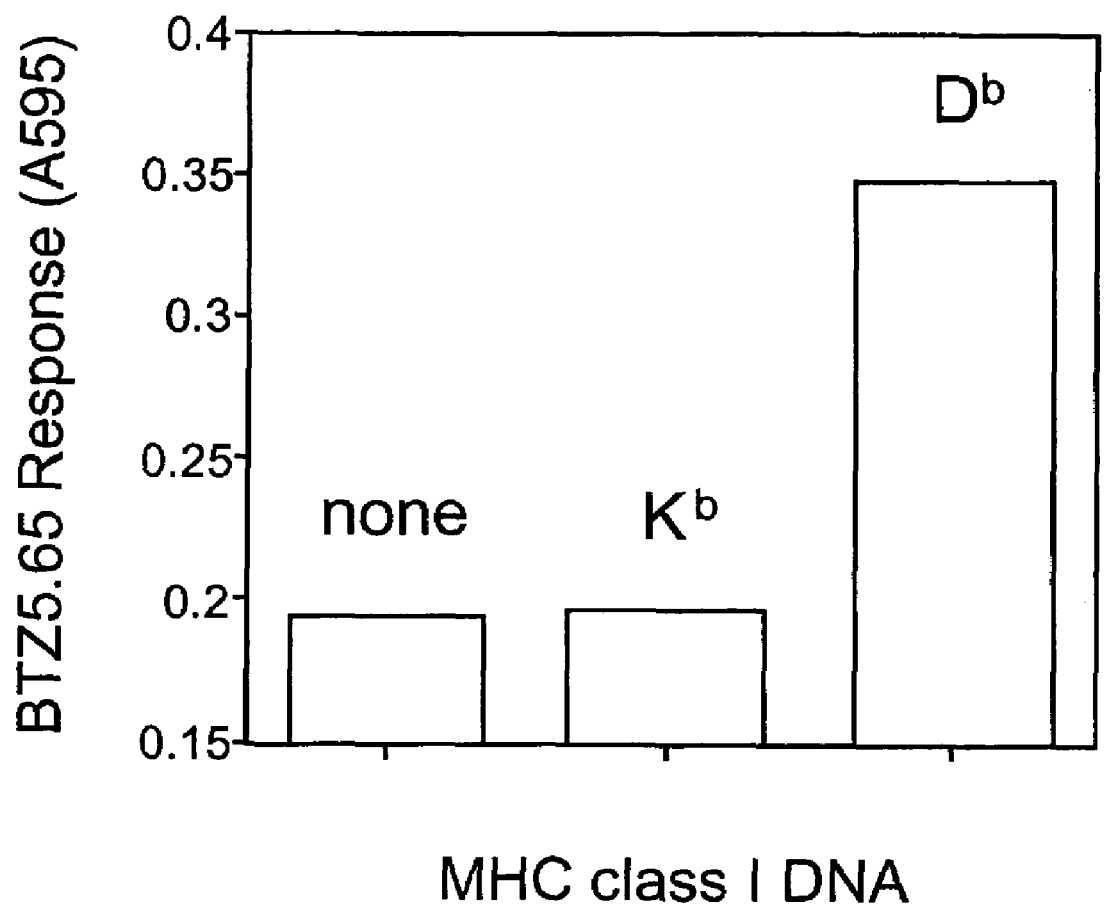
FIG. 13. BTZ5.65 recognizes the ligand encoded by SPAS-1 cDNA only when expressed in context of the relevant MHC class I.

BTZ5.65 Recognizes the Ligand Encoded by SPAS-1 cDNA Only when Expressed in Context of the Relevant MHC Class I To confirm the ability of SPAS-1 as the gene encoding the antigen defined by BTZ5.65, the T hybridoma used for the expression cloning, $8.5 \times 10^4$ hybridoma cells were incubated with $3.0 \times 10^4$ L cells which were transiently transfected with either SPAS-1 cDNA alone, or together with an irrelevant ($K^b$) or correct ($D^b$) MHC cDNA. As shown in FIG. 13, only the combination of SPAS-1 cDNA and the correct restricting element conferred the ability to stimulate the T cell hybridoma. This indicates that SPAS-1 cDNA encodes the relevant antigen recognized by BTZ5.65.

EXAMPLE 12

All Tested BTZs Recognize the Ligand Encoded by SPAS-1 cDNA in Context of Db

Figure 14:
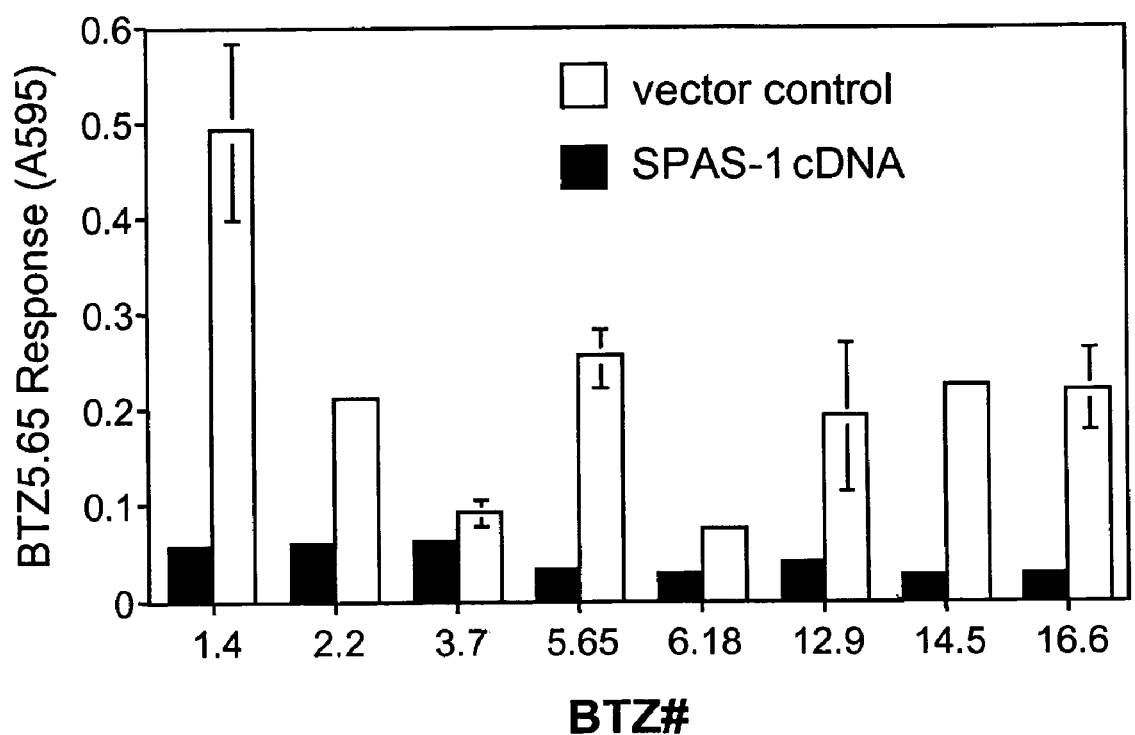
FIG. 14. All tested BTZs recognize the ligand encoded by SPAS-1 cDNA in context of $D_b$.

Seven additional T hybridomas were also stimulated in similar assays described above, providing additional confirmation that SPAS-1 cDNA encodes the H-$2D^b$-restricted antigen recognized by the original anti-TRAMP T cell line (see FIG. 14).

EXAMPLE 13

Virtual Northern obtained by submitting the human SPAS-1 cDNA sequence-lacking the 3'-terminal region encoding for an SH3 domain to the SAGE Tab libraries provided by the NCBI.

The virtual Northern shown in FIG. 15 suggests that the human SPAS-1 SAGE Tag is predominantly found in libraries from cancer tissues, particularly in one prostate cancer library of an advanced stage of prostate cancer.

EXAMPLE 14

The minimal antigenic T cell epitope of SPAS-1 capable of activating the TRAMP-specific T cell hybridomas was identified using standard techniques. The antigenic peptide was found to be encoded by nucleotides 730 to 756 of the SPAS-1 (T) cDNA and had the following amino acid sequence: Ser Thr His Val Asn His Leu His Cys.

Figure 16:
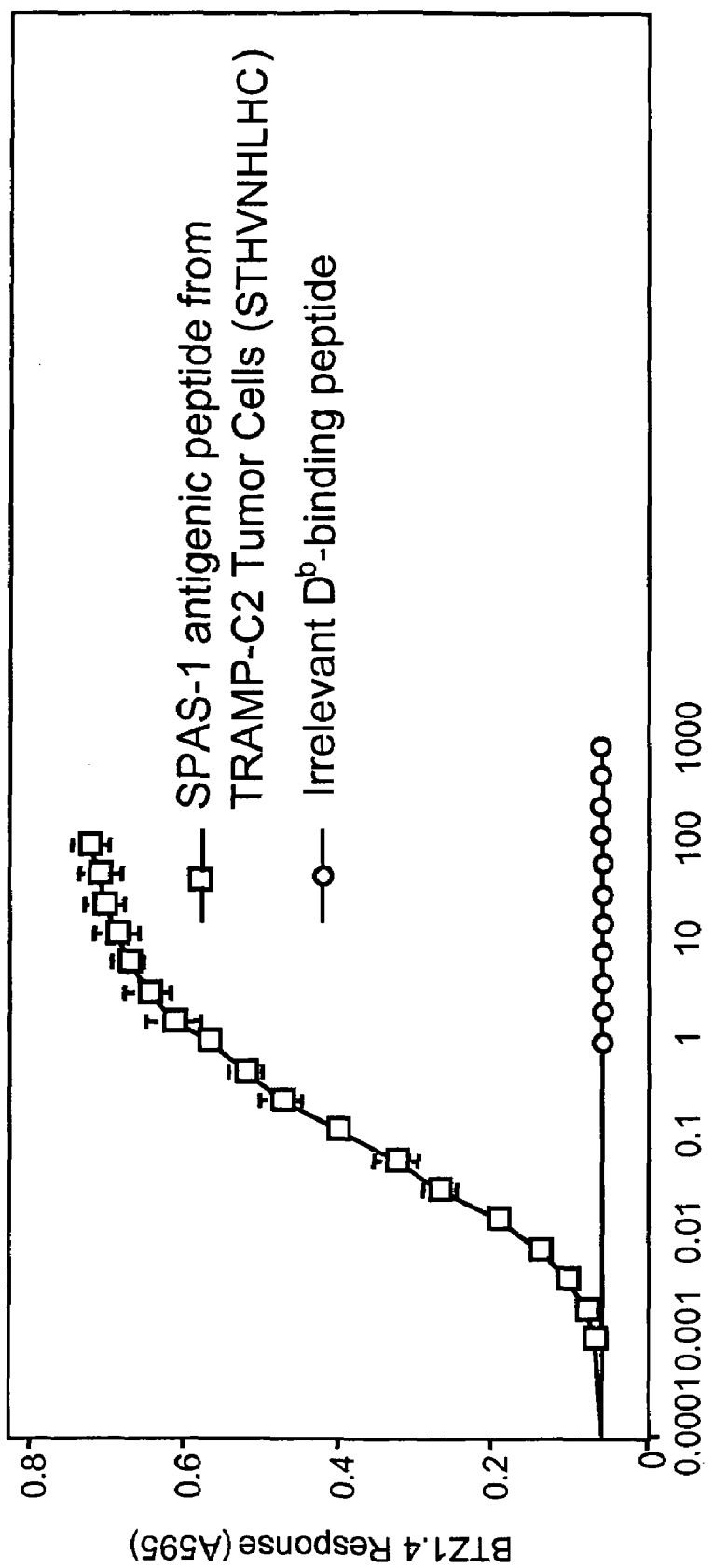
FIG. 16. TRAMP-specific T cells respond to the SPAS-1 peptide (SEQ ID NO:25) STHVNHLHC bound to H-2 $D^b$.

The synthetic peptide (SEQ ID NO:25) STHVNHLHC corresponding to the identified minimal T cell epitope was synthesized and pulsed on L-cells expressing the restricted MHC class I molecule H-$2D^b$ and used to activate the TRAMP-C2-specific T cell hybridoma BTZ1.4. FIG. 16 shows that while the peptide (SEQ ID NO:25) STHVNHLHC acted as a strong antagonist of T cell activation, another H-2Db-binding peptide from the same SPAS-1 protein did not induce T cell activation.

EXAMPLE 15

Figure 17:
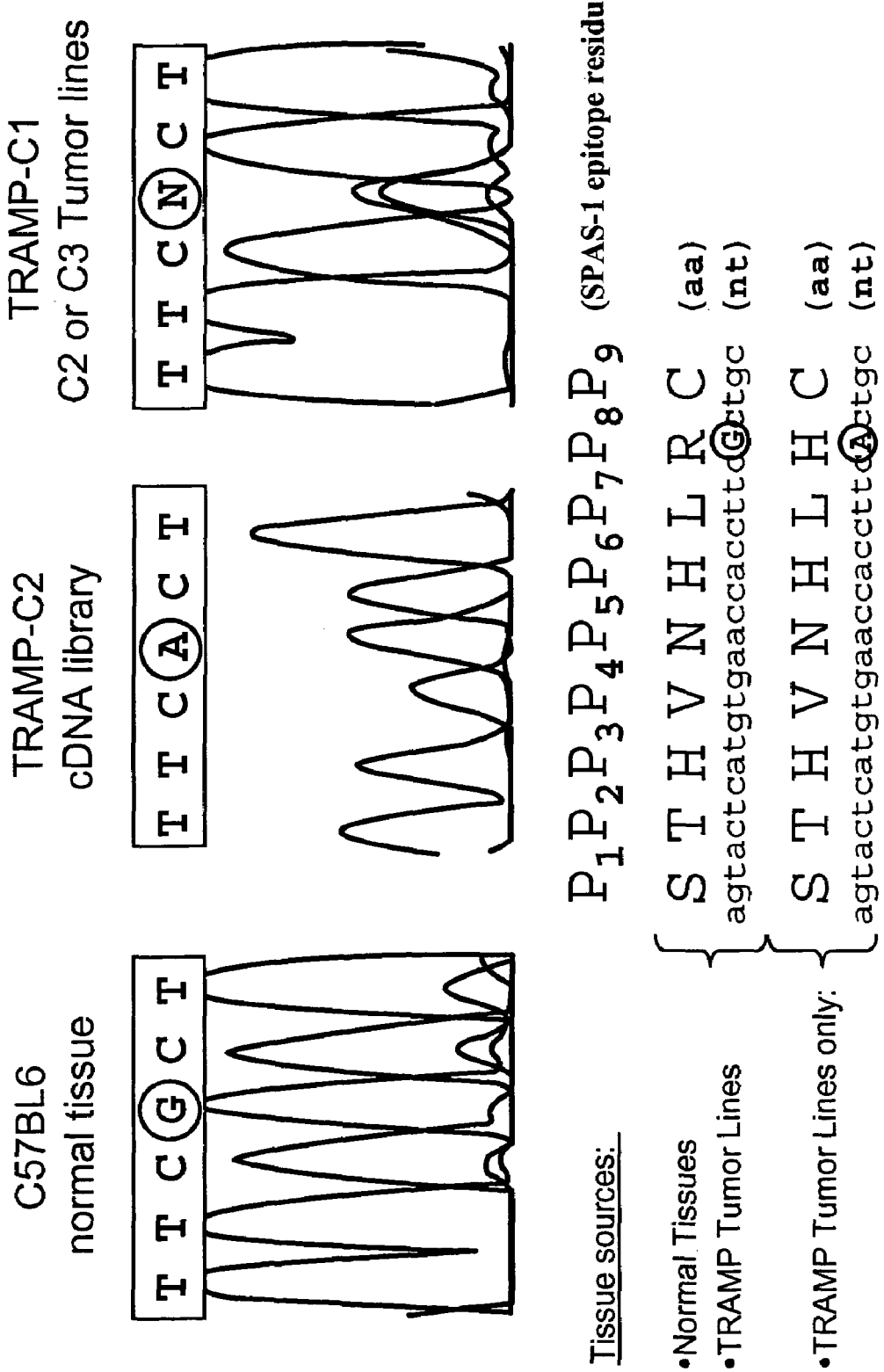
FIG. 17. SPAS-1 germline sequence reveals a G to A substitution in the genetic region encoding Residue P8 of the T cell epitope (SEQ ID NOS: 23-26).

SPAS-1 RNA was isolated from C57/B16 mouse normal tissues including liver, lung, prostate and heart and cDNA was made by RT PCR following standard procedures. The nucleotide sequence of the SPAS-1 cDNA derived from normal tissues (SPAS-1 (N)) was compared to that of the SPAS-1 cDNA originally isolated from the TRAMP-C2 cDNA library (SPAS-1 (T)). The sequence analysis of SPAS-1 cDNA from normal tissues revealed a G to A nucleotide substitution at position 752 in the genetic region encoding the antigenic T cell epitope (see FIG. 17). The three available TRAMP tumor cell lines TRAMP-C1, C2, and C3 expressed both versions of SPAS-1 cDNA (SPAS-1 (N) and SPAS-1 (T)). Importantly, FIG. 17 shows the single genetic substitution at position 752 resulted in an amino acid change at position P8 of the T cell epitope: Arginine (normal tissue) to Histidine (TRAMP tumor lines) substitution.

EXAMPLE 16

In order to determine the reactivity of TRAMP-specific T cell hybridomas with tumor and normal cell derived SPAS-1 epitopes, minigenes were constructed corresponding to nucleotides 730 to 752 of SPAS-1 (T) and SPAS-1 (N) cDNAs. L cells were transiently transfected with these minigenes for processing and presentation of the respectively encoded peptides following standard procedures. T cell hybridoma BTZ.14 was added to the cultures 48 hours later and its specific activation was measured as described previously.

Figure 18:
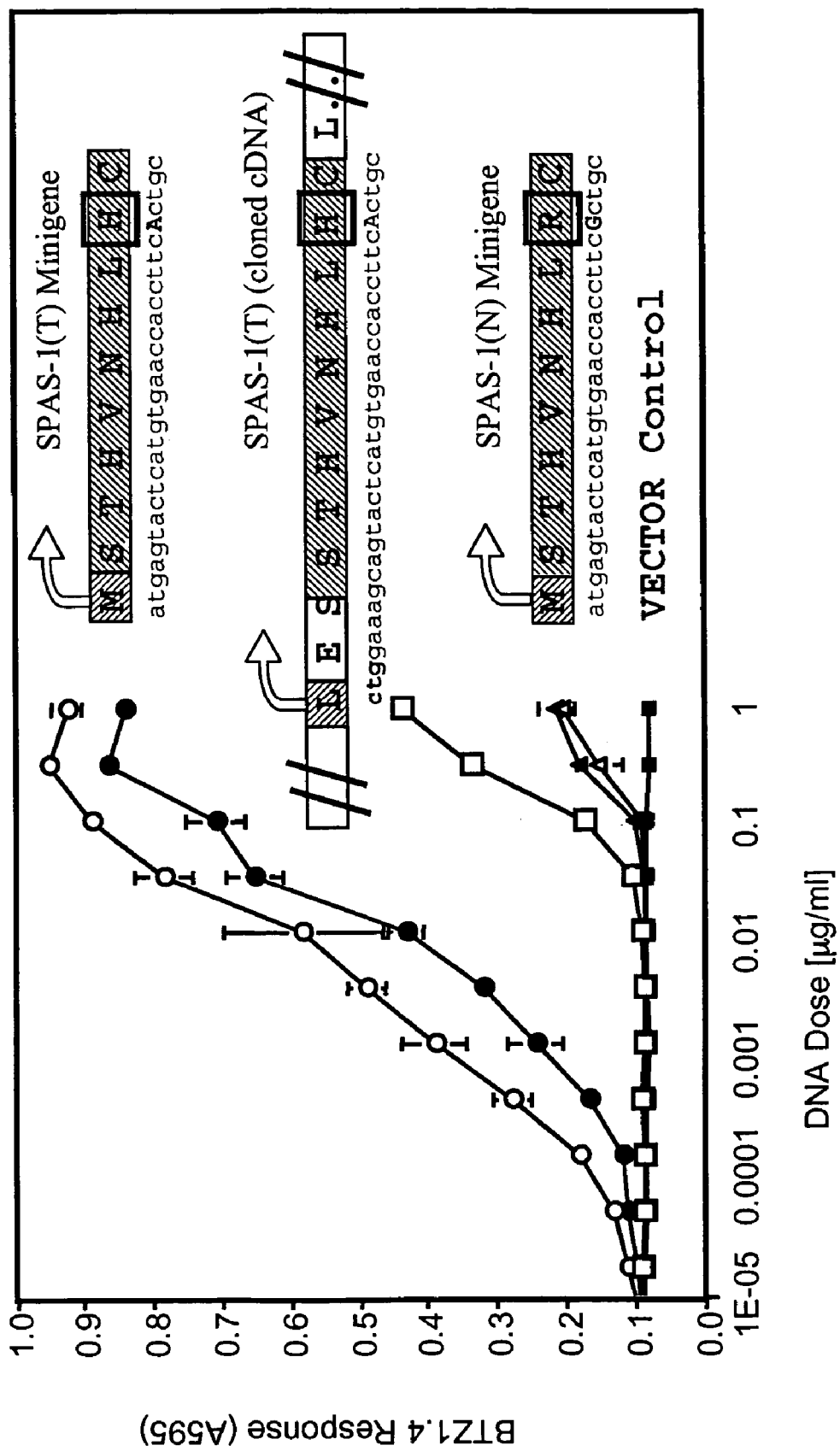
FIG. 18. H to R substitution in the antigenic peptide results in weak T cell activation. (SEQ ID NOS: 27-32).
Figure 20:
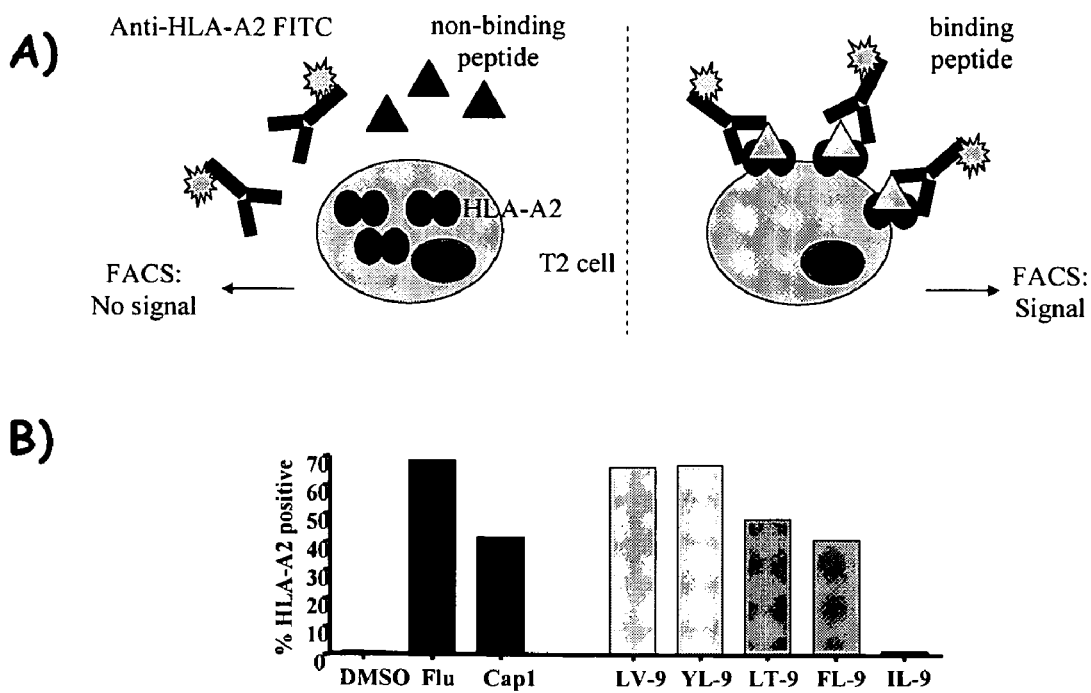
FIG. 20: T2 assay to determine physical binding of predicted SPAS-1 peptides to HLA-A2: To confirm HLA-A2 binding, the five synthetic peptides were tested in a conventional T2 binding assay. A) T2 assay: due to their TAP deficiency, T2 cells only contain unstable, empty HLA-A2 molecules that do not remain on the cell surface. An HLA-A2 binding peptide will stabilize HLA-A2 cell surface expression, which can then be detected by flow cytometry. B) Four out of the five predicted peptides bound to HLA-A2 as demonstrated by stabilization of surface HLA-A2 expression. Positive controls: Flu peptide and CEA Cap1 peptide; negative control: DMSO.
Figure 21:
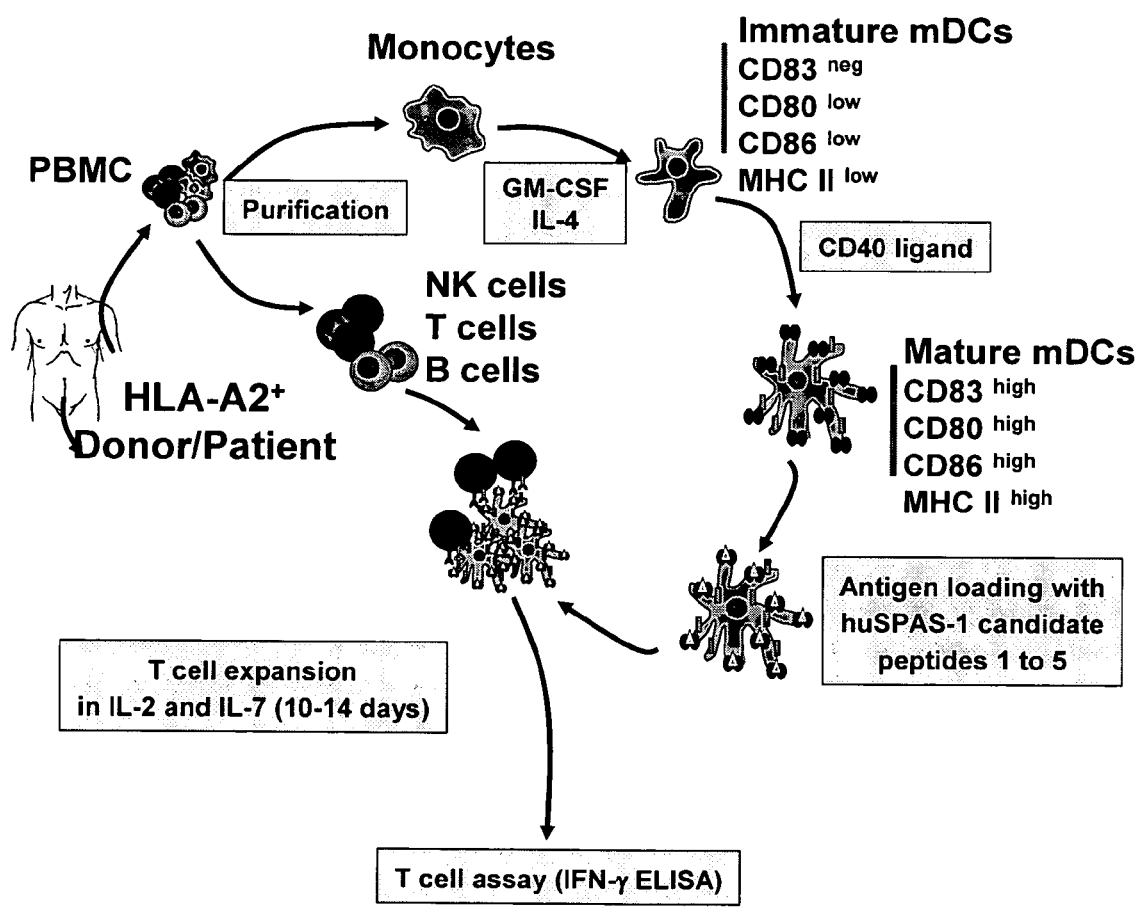
FIG. 21: Strategy for the generation of human cytotoxic T lymphocytes (CTLs) specific for candidate human SPAS-1 peptides: In order to determine whether CD8+ T cells specific for human SPAS-1 peptides are present in the periphery of healthy individuals we used an in vitro priming strategy. Briefly, immature Myeloid Dendritic Cells (mDCs) were generated from culturing monocytes isolated from Peripheral Blood Mononuclear Cells (PBMCs) of a healthy HLA-A2+ donor for 5 days in GM-CSF and IL-4. Upon overnight incubation with CD40 ligand, the mDC were induced to mature as shown by up-regulated cell surface expression of CD80, CD83, CD86 and MHC II (HLA-DR). The mature mDCs were loaded with either of the five candidate T cell epitopes from human SPAS-1 P1 (LV-9); P2 (YL-9); P3 (LT-9); P4 (FL-9); P5 (IL-9), and used to stimulate autologous T cells isolated from the same donor. Five days after first stimulation CD8+ T cells were isolated from the culture and allowed to expand in the presence of 10 U/ml IL-2 and 5 ng/ml IL-7 for another 10 days at which point T cell cultures were assessed for their capacity to produce IFN-γ in response to the corresponding peptide, pulsed onto a HLA-A2 expressing cell line such as A221 or THP-1.
Figure 22:
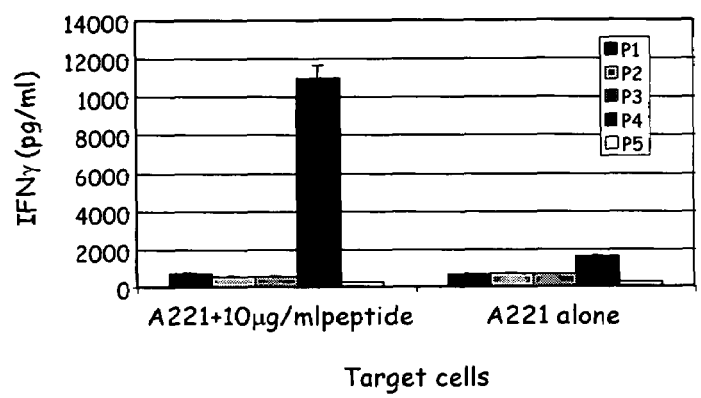
FIG. 22: SPAS-1 Derived Epitope P4 (FL-9) is Immunogenic in Humans. Monocyte-derived DC from HLA-A2+ healthy donors were pulsed with each of the five candidate peptides P1 (LV-9); P2 (YL-9); P3 (LT-9); P4 (FL-9); P5 (IL-9) and then incubated separately with autologous PBMC. Following another in vitro restimulation, T cell cultures were assessed for their capacity to produce IFN-γ in response to the corresponding peptide, pulsed onto the HLA-A2 expressing cell line A221. IFN-γ was assessed by ELISA on the cell supernatants in triplicate wells.

While the minigene from SPAS-1 (T) cDNA lead to strong activation of the T cell hybridoma, FIG. 18 shows that the minigene derived from SPAS-1 (N) cDNA only poorly activated the same hybridoma. Taken together, this data shows that only SPAS-1 (T) cDNA was the source of the anti-TRAMP tumor response in mice. Mutations in the coding sequence of SPAS-1 or any other gene have a number of different effects. These effects can include: (1) the generation of new T cell epitopes that might provoke an immune response, and (2) the conferring of oncogenic activity on the gene product. The latter effects could be a result of functional alterations in proteins that regulate, e.g., cell cycle progression and proliferation of the cells, or that play a role in regulating cell death by apoptosis. Changes in function could be either positive or negative and involve acquisition of new activity or loss of normal activity. Example could include loss of ability to inhibit cell cycle progression or promote cell death, or acquisition of activity that would promote cell cycle progression or that would inhibit cell death. It is possible that mutations that confer oncogenic activity can occur at different positions of the gene in different tumors.

EXAMPLE 17

The goal of immunological approaches to cancer therapy is the induction of anti-tumor responses of sufficient strength to eradicate disseminated tumors. However, the application of immunotherapy to prostate cancer has been hampered by the lack of immunologically validated targets for T cell responses. We have applied our efforts in developing a strategy for the identification of novel T cell targets in the Transgenic Adenocarcinoma of Mouse Prostate (TRAMP) model based on the rationale that identified murine targets will have human orthologs with potential relevance for the development of immunotherapy in human prostate cancer. We have generated TRAMP-specific T cells by immunizing mice with a GM-CSF producing TRAMP tumor cell vaccine in the presence of CTLA-4 antibody blockade and used these cells to identify the first T cell-defined TRAMP tumor antigen, which we designated SPAS-1 (for stimulator of prostatic adenocarcinoma specific T cells). This protein is also known as SH3GLB2 (SH3-domain, GRB2-like, endophilin B2). The human homolog gene (SEQ ID NO:33) is described in (Genbank Accession No. AF257319; Pierrat, B. et al., SH3GLB, a new endophilin-related protein family featuring an SH3 domain).

We determined that the immunodominant SPAS-1/SH3GLB2 epitope arose from a point mutation in one allele of the SPAS-1 gene in TRAMP tumor cells and that immunization with dendritic cells (DCs) pulsed with mutant SPAS-1 peptide resulted in protection against TRAMP-C2 tumor challenge. SPAS-1/SH3GLB2 has a human ortholog that is over-expressed in lymph node metastasis of prostate cancer.

Human SPAS-1 protein regions containing candidate HLA-A2-binding peptides were predicted with the computer algorithms SYFPEITHI, BIMAS and nHLApred. Five peptides (P1 to P5) were synthesized which had high binding scores according to all three algorithms: P1: (SEQ ID NO:35) LLADELITV (LV-9); P2: (SEQ ID NO:36) YMADAASEL (YL-9); P3: (SEQ ID NO:37) LLLEGISST (LT-9); P4: (SEQ ID NO:38) FLTPLRNFL (FL-9); P5: (SEQ ID NO:39) ILSASASAL (IL-9).

To confirm HLA-A2 binding, the five synthetic peptides were tested in a conventional T2 binding assay. A) T2 assay: due to their TAP deficiency, T2 cells only contain unstable, empty HLA-A2 molecules that do not remain on the cell surface. An HLA-A2 binding peptide will stabilize HLA-A2 cell surface expression, which can then be detected by flow cytometry. B) Four out of the five predicted peptides bound to HLA-A2 as demonstrated by stabilization of surface HLA-A2 expression. Positive controls: Flu peptide and CEA Cap1 peptide; negative control: DMSO.

In order to determine whether CD8+ T cells specific for human SPAS-1 peptides are present in the periphery of healthy individuals we used an in vitro priming strategy. Briefly, immature Myeloid Dendritic Cells (mDCs) were generated from culturing monocytes isolated from Peripheral Blood Mononuclear Cells (PBMCs) of a healthy HLA-A2+ donor for 5 days in GM-CSF and IL-4. Upon overnight incubation with CD40 ligand, the mDC were induced to mature as shown by up-regulated cell surface expression of CD80, CD83, CD86 and MHC II (HLA-DR). The mature mDCs were loaded with either of the five candidate T cell epitopes from human SPAS-1 P1 (LV-9); P2 (YL-9); P3 (LT-9); P4 (FL-9); P5 (IL-9), and used to stimulate autologous T cells isolated from the same donor. Five days after first stimulation CD8+ T cells were isolated from the culture and allowed to expand in the presence of 10 U/ml IL-2 and 5 ng/ml IL-7 for another 10 days at which point T cell cultures were assessed for their capacity to produce IFN-γ in response to the corresponding peptide, pulsed onto a HLA-A2 expressing cell line such as A221 or THP-1.

Monocyte-derived DC from HLA-A2+ healthy donors were pulsed with each of the five candidate peptides P1 (LV-9); P2 (YL-9); P3 (LT-9); P4 (FL-9); P5 (IL-9) and then incubated separately with autologous PBMC. Following another in vitro restimulation, T cell cultures were assessed for their capacity to produce IFN-γ in response to the corresponding peptide, pulsed onto the HLA-A2 expressing cell line A221. IFN-γ was assessed by ELISA on the cell supernatants in triplicate wells.

Figure 23:
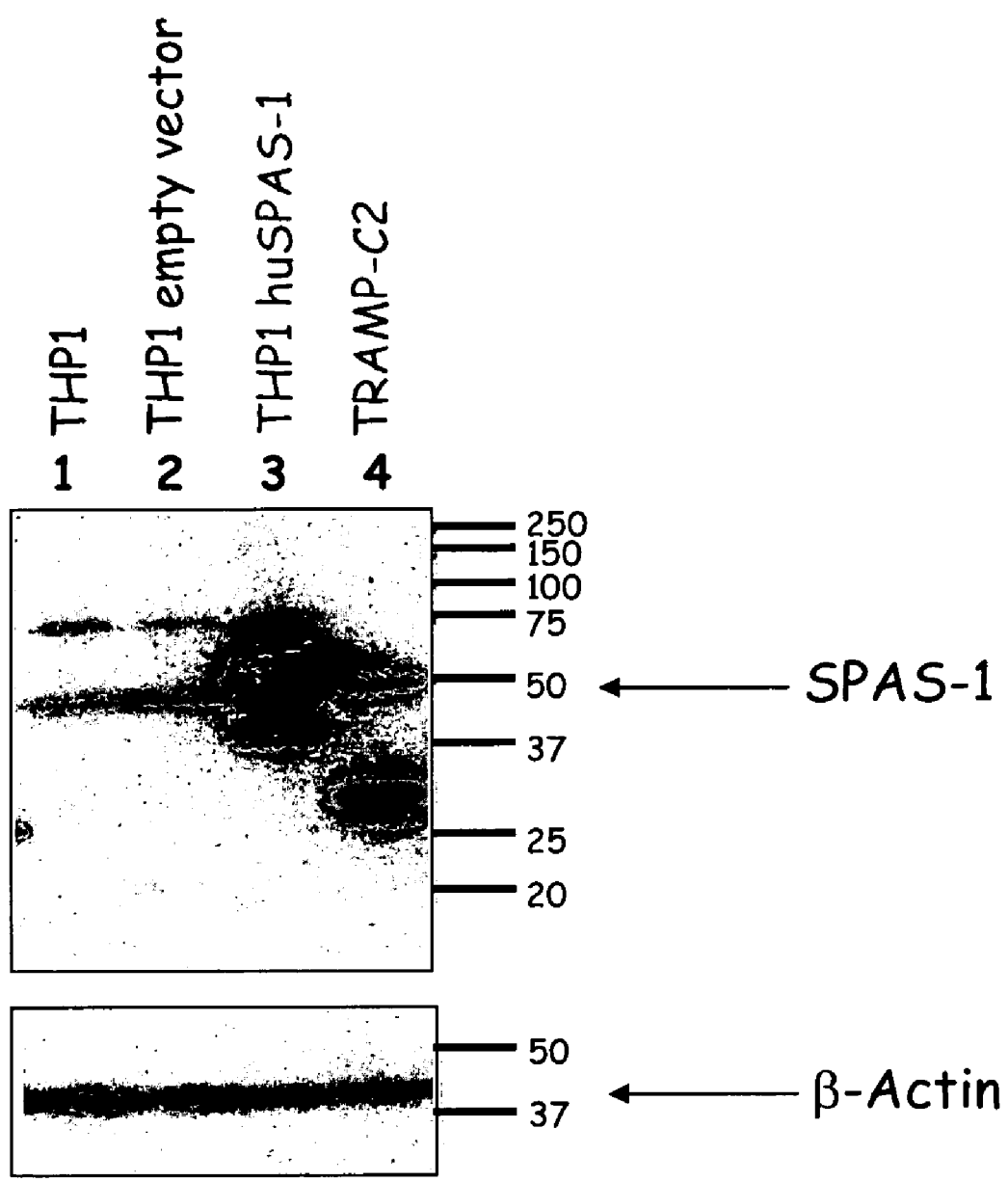
FIG. 23. Overexpression of human SPAS-1 protein in THP-1 cells infected with the pMGlyt2-huSPAS-1 virus was confirmed by Western Blot analysis. Lane 1: lysate from 50,000 untransduced THP-1 cells. Lane 2: lysate from 50,000 THP-1 cells transduced with pMGlyt2 IRES CD8 empty vector. Lane 3: lysate from 50,000 THP-1 cells transduced with pMGlyt2 huSPAS-1 IRES CD8 vector. Lane 4: lysate from 10,000 cells TRAMP-C2 cells as positive control for SPAS-1 expression. A polyclonal Rabbit anti-huSPAS-1 antibody was used for detection of the 45-50 kDa SPAS-1 protein. As control for loading amounts, the same the same membrane was blotted with an anti-β-Actin antibody.
Figure 24:
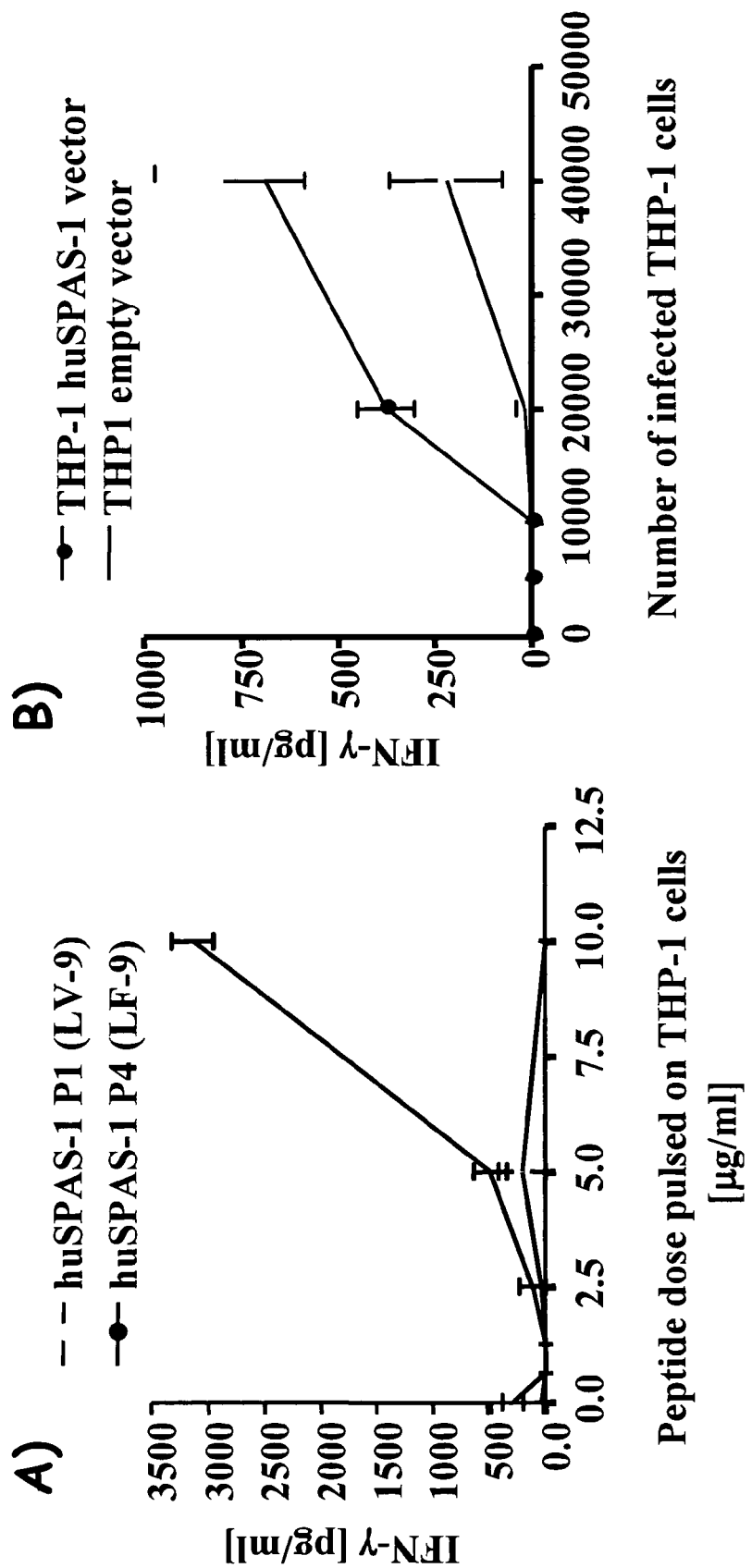
FIG. 24. HuSPAS-1 P4 (FL-9)-specific CD8+ T Cells Recognize Endogenously Processed HuSPAS-1. A) Monocyte-derived DCs from HLA-A2+ healthy donors were pulsed with HuSPAS-1 peptide 4 (FL-9) and then incubated with autologous PBMC. Following another in vitro restimulation, T cell cultures were then assessed for their capacity to produce IFN-γ in response to titrated doses of peptide 4 (FL-9), pulsed onto the HLA-A2 expressing cell line THP-1. IFN-γ was assessed by ELISA on the cell supernatants in triplicate wells. Result: fourteen days after first stimulation these CD8+ T cells specifically produced IFN-γ in response to increasing doses of peptide 4 (FL-9) pulsed onto the HLA-A2 expressing cell line THP-1 but not to increasing doses of irrelevant peptide 1 (LV-9). (100,000 CD8+ T cells/well and 50,000 THP-1 cells/well). B) In order to determine whether these FL-9-specific T cells could also recognize endogenously processed huSPAS-1 peptides, THP-1 cells were stably transduced with either a vector encoding full length human SPAS-1 DNA or with an empty retroviral vector. Responsiveness of the FL-9-reactive CD8+ T cell line was assessed by co-culturing 100,000 CD8+ T cells with titrated numbers of infected THP-1 cells. IFN-γ responses above background were detected only when huSPAS-1 P4-specific T cells were co-cultured in the presence of THP-1 cells overexpressing huSPAS-1 protein, demonstrating that huSPAS-1 peptide 4 (FL-9)-specific CD8+ T cells also recognize endogenously processed huSPAS-1 peptides.

Overexpression of human SPAS-1 protein in THP-1 cells infected with the pMGlyt2-huSPAS-1 virus was confirmed by Western Blot analysis. Shown in FIG. 23, Lane 1: lysate from 50,000 untransduced THP-1 cells. Lane 2: lysate from 50,000 THP-1 cells transduced with pMGlyt2 IRES CD8 empty vector. Lane 3: lysate from 50,000 THP-1 cells transduced with pMGlyt2 huSPAS-1 IRES CD8 vector. Lane 4: lysate from 10,000 cells TRAMP-C2 cells as positive control for SPAS-1 expression. A polyclonal Rabbit anti-huSPAS-1 antibody was used for detection of the 45-50 kDa SPAS-1 protein. As control for loading amounts, the same the same membrane was blotted with an anti-β-Actin antibody.

Monocyte-derived DCs from HLA-A2+ healthy donors were pulsed with HuSPAS-1 peptide 4 (FL-9) and then incubated with autologous PBMC. Following another in vitro restimulation, T cell cultures were then assessed for their capacity to produce IFN-γ in response to titrated doses of peptide 4 (FL-9), pulsed onto the HLA-A2 expressing cell line THP-1. IFN-γ was assessed by ELISA on the cell supernatants in triplicate wells. Result: fourteen days after first stimulation these CD8+ T cells specifically produced IFN-γ in response to increasing doses of peptide 4 (FL-9) pulsed onto the HLA-A2 expressing cell line THP-1 but not to increasing doses of irrelevant peptide 1 (LV-9). (100,000 CD8+ T cells/well and 50,000 THP-1 cells/well). B) In order to determine whether these FL-9-specific T cells could also recognize endogenously processed huSPAS-1 peptides, THP-1 cells were stably transduced with either a vector encoding full length human SPAS-1 DNA or with an empty retroviral vector. Responsiveness of the FL-9-reactive CD8+ T cell line was assessed by co-culturing 100,000 CD8+ T cells with titrated numbers of infected THP-1 cells. IFN-γ responses above background were detected only when huSPAS-1 P4-specific T cells were co-cultured in the presence of THP-1 cells overexpressing huSPAS-1 protein, demonstrating that huSPAS-1 P4 (FL-9)-specific CD8+ T cells also recognize endogenously processed huSPAS-1 peptides.

Detection of circulating SPAS-1/SH3GLB2 reactive T cells. Patients with varying stages of prostate cancer are recruited. Blood from these patients is screened for HLA-A2 expression by antibody staining and flow cytometry. Approximately 50% of the clinic population will be HLA-A2 positive. HLA-A2+ patients from 3 categories defined by extent of disease are evaluated. These three categories are: 1) pre-prostatectomy (localized disease), 2) hormone-naïve recurrent prostate cancer, and 3) HRPC. The hormone-naïve recurrent prostate cancer cohort will include patients with PSA-only as well as metastatic disease.

The null hypothesis for defining a sample size is set at 15% of the subset and only a large proportion with a positive response is of importance. Analysis of 10 samples in each of the 3 subsets allows for testing for a positive outcome in at least 50% of the primary tumor samples compared with a null hypothesis of 15%. This assumes a level of significance of 0.05 for a directional test and power of 0.83. Exploratory analyses characterize the T cell response and investigate whether there is any trend due to grade in the proportion having a positive response.

PBMC are isolated with a Ficoll gradient. The frequency of SPAS-1/SH3GLB2 peptide P4 reactive-T cells is determined by standard IFN-γ ELISPOT. Briefly, PBMC are cultured in 96-well PVDF-based plates (BD Biosciences, San Jose, Calif.) coated with an anti-IFN-γ antibody (BD Biosciences Pharmingen) at $5\times10^5$ cells/well. After 18 hrs of incubation, the cells are washed and the captured IFN-γ is detected with a secondary biotinylated anti-IFN-γ mAb (BD Biosciences Pharmingen). After incubation at RT for 4 hrs, the plates are washed, and goat anti-biotin:1 nm Gold conjugate (GAB1; Ted Pella, Miliville, N.J.) is added for 1 hour at RT. After extensive washing, 30 μL of the silver substrate (Silver Enhancing Kit; Ted Pella) is added into each well and the spot development monitored. Spots are counted using an automated ELISPOT plate reader (AID, Columbia Md.). The cytokine response is expressed as the number of IFN-γ-spot-forming cells (SFCs) per $10^6$ cells. A positive ELISPOT response is defined as >10 background-subtracted spots. Descriptive statistics characterize parameters of interest.

PBMC are also stained with MHC-peptide tetramer (Coulter, San Diego, Calif.) folded with the P4 peptide using established staining techniques. Tetramers for 1) SPAS-1/SH3GLB2 P4 epitope and 2) viral antigens (i.e. CMV, HIV and flu) as controls are used to identify the corresponding antigen-specific CD8 T cells. In addition to quantifying their presence, tetramer+ T cells are co-stained with mAbs against CD3, CD8, CD62L, CD27, CD28, CD56, CD57, CCR7, and NKG2D. A flow cytometry-based assay combining tetramer staining, intracellular cytokine immunofluorescence and CD107a staining will also be performed to determine the proportion of tetramer+ T cells that produce cytokine in response to in vitro stimulation with PMA/ionomycin to determine their capacity to function. A positive tetramer response is defined as >0.5% tetramer+ CD8+ T cells.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications and patent documents cited above are hereby incorporated by reference in their entirety for all purposes to the same extent as if each were so individually denoted.

What is claimed is:

1. A method for determining the presence or absence of a prostate cancer in a patient, comprising the steps of:
    (a) contacting a biological sample obtained from a patient with an antibody or soluble T cell receptor that binds to a SPAS-1 polypeptide as set forth in SEQ ID NO:34;
    (b) detecting in the sample an amount of polypeptide that binds to the antibody or soluble T cell receptor; and
    (c) comparing the amount of polypeptide to a predetermined cut-off value, and therefrom determining the presence or absence of a cancer in the patient, wherein increased binding of said antibody or soluble T cell receptor is indicative of the presence of prostate cancer wherein said predetermined cut-off value is determined from samples without cancer.

2. A method for determining the presence or absence of a prostate cancer in a patient, comprising the steps of:
    contacting a biological sample obtained from a patient with an antibody or soluble T cell receptor that binds to a SPAS-1 polypeptide selected from the group consisting of SEQ ID NO:17; SEQ ID NO:34; SEQ ID NO:35 (LLADELITV)(LV-9); SEQ ID NO:36 (YMADAASEL)(YL-9); SEQ ID NO:37 (LLLEGISST)(LT-9); SEQ ID NO:38 (FLTPLRNFL)(FL-9); and SEQ ID NO:39 (ILSASASAL)(IL-9);
    detecting in the sample an amount of polypeptide that binds to the antibody or soluble T cell receptor; and
    comparing the amount of polypeptide to a predetermined cut-off value is determined obtained from samples without cancer, wherein binding of said antibody or soluble T cell receptor greater than the samples without cancer is indicative of the presence of prostate cancer.

3. A method for determining the presence or absence of a prostate cancer in a patient, comprising the steps of:
    contacting a biological sample obtained from a patient with an antibody or soluble T cell receptor that binds to a SPAS-1 polypeptide as set forth in SEQ ID NO:38 (FLTPLRNFL)(FL-9);
    detecting in the sample an amount of polypeptide that binds to the antibody or soluble T cell receptor; and
    comparing the amount of polypeptide to a predetermined cut-off value is determined obtained from samples without cancer, wherein binding of said antibody or soluble T cell receptor greater than the samples without cancer is indicative of the presence of prostate cancer.

* * * * *